(12) United States Patent
Natsoulis et al.

(10) Patent No.: US 7,588,892 B2
(45) Date of Patent: Sep. 15, 2009

(54) REAGENT SETS AND GENE SIGNATURES FOR RENAL TUBULE INJURY

(75) Inventors: Georges Natsoulis, Kensington, CA (US); Mark Fielden, Moutain View, CA (US); Kurt Jarnagin, San Mateo, CA (US); Kyle Kolaja, San Mateo, CA (US)

(73) Assignee: Entelos, Inc., Foster City, CA (US)

( * ) Notice: Subject to any disclaimer, the term of this patent is extended or adjusted under 35 U.S.C. 154(b) by 371 days.

(21) Appl. No.: 11/184,272

(22) Filed: Jul. 18, 2005

(65) Prior Publication Data

US 2006/0057066 A1    Mar. 16, 2006

Related U.S. Application Data

(60) Provisional application No. 60/589,409, filed on Jul. 19, 2004.

(51) Int. Cl.
C12Q 1/68    (2006.01)
(52) U.S. Cl. .......................................... 435/6
(58) Field of Classification Search ....................... None
See application file for complete search history.

(56) References Cited

U.S. PATENT DOCUMENTS

| | | | |
|---|---|---|---|
| 4,562,157 A | 12/1985 | Lowe et al. |
| 5,143,854 A | 9/1992 | Pirrung et al. |
| 5,474,796 A | 12/1995 | Brennan |
| 5,556,961 A | 9/1996 | Foote et al. |
| 5,569,588 A | 10/1996 | Ashby et al. |
| 5,807,522 A | 9/1998 | Brown et al. |
| 5,930,154 A | 7/1999 | Thalhammer-Reyero |
| 5,968,740 A | 10/1999 | Fodor et al. |
| 6,001,606 A | 12/1999 | Ruben |
| 6,128,608 A | 10/2000 | Barnhill |
| 6,134,344 A | 10/2000 | Burges |
| 6,157,921 A | 12/2000 | Barnhill |
| 6,228,589 B1 | 5/2001 | Brenner |
| 6,291,182 B1 | 9/2001 | Schork et al. |
| 6,372,431 B1 | 4/2002 | Cunningham et al. |
| 6,427,141 B1 | 7/2002 | Barnhill |
| 6,453,241 B1 | 9/2002 | Bassett, Jr. et al. |
| 6,505,125 B1 | 1/2003 | Ho |
| 6,635,423 B2 | 10/2003 | Dooley et al. |
| 6,658,395 B1 | 12/2003 | Barnhill |
| 6,692,916 B2 | 2/2004 | Bevilacqua et al. |
| 6,714,925 B1 | 3/2004 | Barnhill et al. |
| 6,760,715 B1 | 7/2004 | Barnhill et al. |
| 6,789,069 B1 | 9/2004 | Barnhill et al. |
| 6,811,773 B1 | 11/2004 | Gentz |
| 6,816,867 B2 | 11/2004 | Jevons et al. |
| 7,054,755 B2 | 5/2006 | O'Reilly et al. |
| 2002/0012905 A1 | 1/2002 | Snodgrass |
| 2002/0012921 A1 | 1/2002 | Stanton, Jr. |
| 2002/0042681 A1 | 4/2002 | Califano et al. |
| 2002/0095260 A1 | 7/2002 | Huyn |
| 2002/0111742 A1 | 8/2002 | Rocke et al. |
| 2002/0119462 A1 | 8/2002 | Mendrick et al. |
| 2002/0174096 A1 | 11/2002 | O'Reilly et al. |
| 2002/0192671 A1 | 12/2002 | Castle et al. |
| 2003/0093393 A1 | 5/2003 | Mangasarian et al. |
| 2003/0172043 A1 | 9/2003 | Guyon et al. |
| 2003/0180808 A1 | 9/2003 | Natsoulis |
| 2003/0211486 A1 | 11/2003 | Frudakis et al. |
| 2004/0128080 A1 | 7/2004 | Tolley |
| 2004/0234995 A1 | 11/2004 | Musick et al. |
| 2004/0259764 A1 | 12/2004 | Tugendreich et al. |
| 2005/0027460 A1 | 2/2005 | Kelkar et al. |
| 2005/0060102 A1 | 3/2005 | O'Reilly et al. |
| 2005/0130187 A1 | 6/2005 | Shin et al. |
| 2006/0035250 A1 | 2/2006 | Natsoulis |
| 2006/0057066 A1 | 3/2006 | Natsoulis et al. |
| 2007/0021918 A1 | 1/2007 | Natsoulis et al. |
| 2007/0162406 A1 | 7/2007 | Lanckriet |
| 2007/0198653 A1 | 8/2007 | Jarnagin et al. |

FOREIGN PATENT DOCUMENTS

EP    0 935 210 A2    8/1999

(Continued)

OTHER PUBLICATIONS

Rothberg ("The use of animal models in expression pharmacogenomic analyses" Pharmacogenomics J. 2001;1(1):48-58).*

(Continued)

*Primary Examiner*—Kenneth R. Horlick
*Assistant Examiner*—Christopher M. Babic
(74) *Attorney, Agent, or Firm*—Karen E. Flick

(57) ABSTRACT

The invention discloses reagent sets and gene signatures for predicting onset of renal tubule injury in a subject. The invention also provides a necessary set of 186 genes useful for generating signatures of varying size and performance capable of predicting onset of renal tubule injury. The invention also provides methods, apparatuses and reagents useful for predicting future renal tubule injury based on expression levels of genes in the signatures. In one particular embodiment the invention provides a method for predict whether a compound will induce renal tubule injury using gene expression data from sub-acute treatments.

12 Claims, 2 Drawing Sheets

FOREIGN PATENT DOCUMENTS

| WO | WO 96/23078 | 8/1996 |
|---|---|---|
| WO | WO 99/42813 | 8/1999 |
| WO | WO 99/58720 | 11/1999 |
| WO | WO 00/50889 | 8/2000 |
| WO | WO 00/65421 | 11/2000 |
| WO | WO 02/25570 | 3/2002 |
| WO | WO 2005/017807 | 2/2005 |
| WO | PCT/US2005/025890 | 10/2006 |

OTHER PUBLICATIONS

Aardema (Toxicology and genetic toxicology in the new era of "toxicogenomics": impact of "-omics" technologies. Mutat Res. Jan. 29, 2002;499(1):13-25).*

Fielden ((Challenges and limitations of gene expression profiling in mechanistic and predictive toxicology Toxicol Sci. Mar. 2001;60(1):6-10).*

Sorace J et al., "Functional Bioinformatics: The Cellular Response Database", *Frontiers in Bioscience*, vol. 2, (1997), pp. 31-36.

Weinstein J et al., "An Information-Intensive Approach to the Molecular Pharmacology of Cancer", *Science*, vol. 275, (1997), pp. 343-349.

Kim S et al., "Strong Feature Sets from Small Samples", *Journal of Computational Biology*, vol. 9, (2002), pp. 127-146.

Goldfarb D et al., "Robust Convex Quadratically Constrained Programs", *Mathematical Progamming*, vol. 97, (2003), pp. 495-515.

Rifkin and Klautau, "In Defense of One-Vs-All Classification," Journal of Machine Learning Research 5: 101-141 (2004).

Bredensteiner et al., "Multicategory Classification by Support Vector Machines," Computational Optimization and Applications, 12: 53-79 (1999).

El Ghaoui, et al., "Robust classifiers with interval data" *Report # UCB/CSD-03-1279 Computer Science Division (EECS)*, University of California, Berkeley, California (2003).

Brown et al., "Knowledge-based analysis of microarray gene expression data by using support vector machines," Proc Natl Acad Sci U S A 97: 262-267 (2000).

Bhattacharyya C et al., "Simultaneous Classification and Relevant Feature Identification in High-Dimensional Spaces : Application to Molecular Profiling Data", *Signal Processing*, vol. 83, (2003), pp. 729-743.

Golub et al., "Molecular Classification of Cancer: Class Discovery and Class Prediction by Gene Expression Monitoring," Science 286: 531-37 (Oct. 1999).

Natsoulis et al., "Classification of a large microarray data set: Algorithm comparison and analysis of drug signatures," Genome Research 15(5):724-36 (May 2005).

Wolfinger et al., "Assessing Gene Significance from cDNA Microarray Expression Data via Mixed Models," J. Computational Biol. 8(6); 625-37 (2001).

Ganter et al., "Development of a large-scale chemogenomics database to improve drug candidate selection and to understand mechanisms of chemical toxicity and action," *Journal of Biotechnology* 119: 219-244 (2005).

Roter, "Large-scale integrated databases supporting drug discovery," Curr Opin Drug Discov Devel. May 2005;8(3):309-15.

Fielden et al., "A gene expression signature that predicts the future onset of drug-induced renal tubular toxicity," Toxicol Pathol. 2005;33(6):675-83.

Fielden et al., "Preclinical drug safety analysis by chemogenomic profiling in the liver," Am J Pharmacogenomics. 2005;5(3).

Fielden et al., "The state-of-the-art in predictive toxicogenomics," Curr Opin Drug Discov Devel. Jan. 2006;9(1).

Fielden et al.,"The state-of-the-art in predictive toxicogenomics," Curr Opin Drug Discov Devel. Jan. 2006;9(1):84-91.

Tugendreich et al., "NSAID-induced acute phase response is due to increased intestinal permeability and characterized by early and consistent alterations in hepatic gene expression," Toxicol Pathol. 2006;34(2):168-79.

Lee et al., "Drug-induced changes in P450 enzyme expression at the gene expression level: a new dimension to the analysis of drug-drug interactions," Xenobiotica. 2006; 36(10-11):1013-80.

Natsoulis et al., "liver pharmacological and xenobiotic gene response repertoire," Mol Syst Biol. 2008;4:175. Epub Mar. 25, 2008.

Fielden et al., "A gene expression biomarker provides early prediction and mechanistic assessment of hepatic tumor induction by nongenotoxic chemicals," Toxicol Sci. Sep. 2007;99(1):90-100. Epub Jun. 8, 2007.

Yang et al., "Clinicopathological and tissue indicators of para-aminophenol nephrotoxicity in sprague-dawley rats," Toxicol Pathol. 2007;35(4):521-32.

Wang et al., "Validation of putative genomic biomarkers of nephrotoxicity in rats," Toxicology. Apr. 18, 2008;246(2-3).

Fielden et al., "Interlaboratory evaluation of genomic signatures for predicting carcinogenicity in the rat," Toxicol Sci. May 2008;103(1).

Hu et al., "Induction of cyp1a1 is a nonspecific biomarker of aryl hydrocarbon receptor activation: results of large scale screening of pharmaceuticals and toxicants in vivo and in vitro," Mol Pharmacol. Jun. 2007;71(6):1475-86. Epub Feb. 27, 2007.

D'haeseleer et al., Pacific Symposium on Biocomputing, 1999, p. 1-34.

UPGMA Website, www.icp.ucl.ac.be/~opperd/private/upgma.html, published Sep. 1997, p. 1-6.

* cited by examiner

US 7,588,892 B2

REAGENT SETS AND GENE SIGNATURES FOR RENAL TUBULE INJURY

CROSS REFERENCE TO RELATED APPLICATIONS

This application claims priority from U.S. Provisional Application No. 60/589,409, filed Jul. 19, 2004, which is hereby incorporated by reference in its entirety.

FIELD OF THE INVENTION

This invention relates to reagent sets and gene signatures useful for predicting the onset of renal tubule injury (RTI) in a subject. The invention also provides methods, apparatuses and kits useful for predicting occurrence of renal tubule injury based on expression levels of genes in the signatures. In one embodiment the invention provides a method for predicting whether a compound will induce renal tubule injury using gene expression data from sub-acute treatments.

BACKGROUND OF THE INVENTION

Renal tubule injury (also referred to herein as, "tubular nephrosis") is a common drug-induced toxicity that includes degenerative lesions of the renal tubules, such as acute tubular dilation, vacuolation and necrosis. Necrotic lesions of the tubules can arise as a consequence of septic, toxic or ischemic insult, and is a frequent cause of renal failure among hospitalized patients. Recognition is hampered by the lack of accurate markers and the shortcomings and over-reliance of serum markers of impaired glomerular filtration rate (i.e., serum creatinine and blood urea nitrogen) (see e.g., Schrier et al., "Acute renal failure: definitions, diagnosis, pathogenesis, and therapy," J Clin Invest, 114(1):5-14 (2004)). Drugs associated with the development of tubular nephrosis include aminoglycoside antibiotics, antifungals, antineoplastics, immunosuppresants and radiocontrast dyes, among others.

Similarly to the human clinical setting, long-term treatment of rats during preclinical drug development with relatively low doses of aminoglycoside antibiotics, heavy metal toxicants or antineoplastic drugs, for example, leads to the development of degenerative lesions of the renal tubules. However, histopathological or clinical indications of kidney injury are not readily apparent in the early course of treatment, thus necessitating expensive and lengthy studies.

The development of methods to predict the future onset of renal tubule injury (RTI) and gain a greater understanding of the underlying mechanism, would facilitate the development more reliable clinical diagnostics and safer therapeutic drugs. In addition, improved preclinical markers for RTI would dramatically reduce the time, cost, and amount of compound required in order to prioritize and select lead candidates for progression through drug development.

SUMMARY OF THE INVENTION

The present invention provides methods, reagent sets, gene sets, and associated apparatuses and kits, that allow one to determine the early onset of renal tubule injury (or nephrotoxicity) by measuring gene expression levels. In one particular embodiment, the invention provides a RTI "necessary set" of 186 genes mined from a chemogenomic dataset. These genes are information-rich with respect to classifying biological samples for onset of RTI, even at sub-acute doses and time points of 5 days or earlier, where clinical and histopathological evidence of RTI are not manifested. Further, the invention discloses that the necessary set for RTI classification has the functional characteristic of reviving the performance of a fully depleted set of genes (for classifying RTI) by supplementation with random selections of as few as 10% of the genes from the set of 186. In addition, the invention discloses that selections from the necessary set made based on percentage impact of the selected genes may be used to generate high-performing linear classifiers for RTI that include as few as 4 genes. In one embodiment, the invention provides several different linear classifiers (or gene signatures) for RTI. For all of the disclosed embodiments based on the necessary set of 186 genes, the invention also provides reagent sets and kits comprising polynucleotides and/or polypeptides that represent a plurality of genes selected from the necessary set.

In one embodiment, the present invention provides a method for testing whether a compound will induce renal tubule injury in a test subject, the method comprising: administering a dose of a compound to at least one test subject; after a selected time period, obtaining a biological sample from the at least one test subject; measuring the expression levels in the biological sample of at least a plurality of genes selected from those listed in Table 4; determining whether the sample is in the positive class for renal tubule injury using a classifier comprising at least the plurality of genes for which the expression levels are measured. In one embodiment, the method is carried out wherein the test subject is a mammal selected from the group consisting of a human, cat, dog, monkey, mouse, pig, rabbit, and rat. In one preferred embodiment the test subject is a rat. In one embodiment, the biological sample comprises kidney tissue. In one embodiment, the method is carried out wherein the test compound is administered to the subject intravenously (IV), orally (PO, per os), or intraperitoneally (IP). In one embodiment, the method is carried out wherein the dose administered does not cause histological or clinical evidence of renal tubule injury at about 5 days, about 7 days, about 14 days, or even about 21 days. In one embodiment, the method is carried out wherein the expression levels are measured as $\log_{10}$ ratios of compound-treated biological sample to a compound-untreated biological sample. In one embodiment, the method of the invention is carried out wherein the classifier is a linear classifier. In alternative embodiments, the classifier may be a non-linear classifier. In one embodiment, the method is carried out wherein the selected period of time is about 5 days or fewer, 7 days or fewer, 14 days or fewer, or even 21 days or fewer. In one embodiment of the method, the selected period of time is at least about 28 days.

In one embodiment, the method is carried out wherein the classifier comprises the genes and weights corresponding to any one of iterations 1 through 5 in Table 4. In one embodiment, the method of the invention is carried out wherein the classifier for renal tubule injury classifies each of the 64 compounds listed in Table 2 according to its label as nephrotoxic and non-nephrotoxic.

In one embodiment, the method is carried out wherein the linear classifier for renal tubule injury is capable of classifying a true label set with a log odds ratio at least 2 standard deviations greater than its performance classifying a random label set. In preferred embodiments of the method, the linear classifier for renal tubule injury is capable of performing with a training log odds ratio of greater than or equal to 4.35. In another embodiment, the plurality of genes includes at least 4 genes selected from those listed in Table 4, the four genes having at least having at least 2, 4, 8, 16, 32, or 64% of the total impact of all of the genes in Table 4.

The present invention also provides a gene sets, and reagent sets based on those gene sets, that are useful for testing whether renal tubule injury will occur in a test subject. In one embodiment, the invention provides a reagent set comprising a plurality of polynucleotides or polypeptides representing a plurality of genes selected from those listed in Table 4. In one embodiment, the reagent set comprises a plurality of genes includes at least 4 genes selected from those listed in Table 4, the 4 genes having at least 2% of the total impact of all of the genes in Table 4. In another embodiment, the reagent set comprises a plurality of genes includes at least 8 genes selected from those listed in Table 4, the 8 genes having at least 4% of the total impact of all of the genes in Table 4. Other embodiments include reagent sets based on subsets of genes randomly selected from Table 4, wherein the subset includes at least 4 genes having at least 1, 2, 4, 8, 16, 32, or 64% of the total impact. In preferred embodiments, the reagent sets of the invention include represent as few genes as possible from Table 4 while maximizing percentage of total impact. In preferred embodiments, the reagent sets of the invention include fewer than 1000, 500, 400, 300, 200, 100, 50, 20, 10, or even 8, polynucleotides or polypeptides representing the plurality of genes from Table 4. In one embodiment, the reagent sets consist essentially of polynucleotides or polypeptides representing the plurality of genes from Table 4. Further, the invention comprises kits comprising the reagent sets as components. In one embodiment, the reagent set is packaged in a single container consisting essentially of polynucleotides or polypeptides representing the plurality of genes from Table 4.

In one embodiment, the reagent sets of the invention comprise polynucleotides or polypeptides representing genes comprising a random selection of at least 10% of the genes from Table 4, wherein the addition of said randomly selected genes to a fully depleted gene set for the renal tubule injury classification question increases the average logodds ratio of the linear classifiers generated by the depleted set to at least about 4.0. In another embodiment, a random selection of at least 20% of the genes from Table 4, wherein the addition of said randomly selected genes to a fully depleted gene set for the renal tubule injury classification question increases the average logodds ratio of the linear classifiers generated by the depleted set to at least about 4.5.

In one embodiment, the invention provides a reagent set for classifying renal tubule injury comprising a set of polynucleotides or polypeptides representing a plurality of genes selected from Table 4, wherein the addition of a random selection of at least 10% of said plurality of genes to the fully depleted set for the renal tubule injury classification question increases the average logodds ratio of the linear classifiers generated by the depleted set by at least 3-fold. In another embodiment, the reagent set includes at least 20% of said plurality of genes to the fully depleted set for the renal tubule injury classification question increases the average logodds ratio of the linear classifiers generated by the depleted set by at least 2-fold.

In another preferred embodiment the plurality of genes are selected from the variables of a linear classifier capable of classifying renal tubule injury with a training log odds ratio of greater than or equal to 4.35. In one preferred embodiment, the plurality of genes is the set of genes in any one of iterations 1 through 5 in Table 4. In another embodiment, the plurality of genes is the set of genes in any one of Tables 7, 8, 10, and 11. In one embodiment the reagents are polynucleotide probes capable of hybridizing to a plurality of genes selected from those listed in Table 4, and in a preferred embodiment, the polynucleotide probes are labeled.

In another embodiment, the reagents are primers for amplification of the plurality of genes. In one embodiment the reagents are polypeptides encoded by a plurality of genes selected from those listed in Table 4. Preferably the reagents are polypeptides that bind to a plurality proteins encoded by a plurality of genes selected from those listed in Table 4. In one preferred embodiment, the reagent set comprises secreted proteins encoded by genes listed in Table 4.

The present invention also provides an apparatus for predicting whether renal tubule injury will occur in a test subject comprising a reagent set as described above. In preferred embodiments, the apparatus comprises a device with reagents for detecting polynucleotides, wherein the reagents comprise or consist essentially of a reagent set for testing whether renal tubule injury will occur in a test subject as described above.

In one embodiment, the apparatus comprises at least a plurality of polynucleotides or polypeptides representing a plurality of genes selected from those listed in Table 4. In one embodiment the apparatus comprises a plurality of genes includes at least 4 genes selected from those listed in Table 4, the four genes having at least 2% of the total impact of the genes in Table 4. In another preferred embodiment the plurality of genes are variables in a linear classifier capable of classifying renal tubule injury with a training log odds ratio of greater than or equal to 4.35. In one embodiment, the apparatus comprises the plurality of genes listed in any one of iterations 1 through 5 in Table 4. In one preferred embodiment, the apparatus comprises polynucleotide probes capable of hybridizing to a plurality of genes selected from those listed in Table 4. In preferred embodiments, the apparatus comprises a plurality of polynucleotide probes bound to one or more solid surfaces. In one embodiment, the plurality of probes are bound to a single solid surface in an array. Alternatively, the plurality of probes are bound to the solid surface on a plurality of beads. In another preferred embodiment, the apparatus comprises polypeptides encoded by a plurality of genes selected from those listed in Table 4. In one preferred embodiment, the polypeptides are secreted proteins encoded by genes listed in Table 4.

The present invention also provides a method for predicting renal tubule injury in an individual comprising: obtaining a biological sample from the individual after short-term treatment with compound; measuring the expression levels in the biological sample of at least a plurality of genes selected from Table 4; and determining whether the sample is in the positive class for renal tubule injury using a linear classifier comprising at least the plurality of genes for which the expression levels are measured; wherein a sample in the positive class indicates that the individual will have renal tubule injury following sub-chronic treatment with compound. In one preferred embodiment, the method for predicting renal tubule injury is carried out wherein the genes encode secreted proteins. In a preferred embodiment, the individual is a mammal, and preferably a rat. In another preferred embodiment, the biological sample is selected from blood, urine, hair or saliva. In another preferred embodiment of the method, the expression $\log_{10}$ ratio is measured using an array of polynucleotides.

In another embodiment, the invention provides a method for monitoring treatment of an individual for renal tubule injury, or with a compound suspected of causing renal tubule injury, said method comprising: obtaining a biological sample from the individual after short-term treatment with compound; measuring the expression levels in the biological sample of at least a plurality of genes selected from Table 4; and determining whether the sample is in the positive class for renal tubule injury using a linear classifier comprising at least the plurality of genes for which the expression levels are measured; wherein a sample in the positive class indicates that the individual will have renal tubule injury. In a preferred embodiment, the individual is a mammal, and preferably a rat. In another preferred embodiment, the biological sample is selected from blood, urine, hair or saliva. In another preferred embodiment of the method, the expression $\log_{10}$ ratio is measured using an array of polynucleotides.

DETAILED DESCRIPTION OF THE INVENTION

I. Overview

Figure 1:
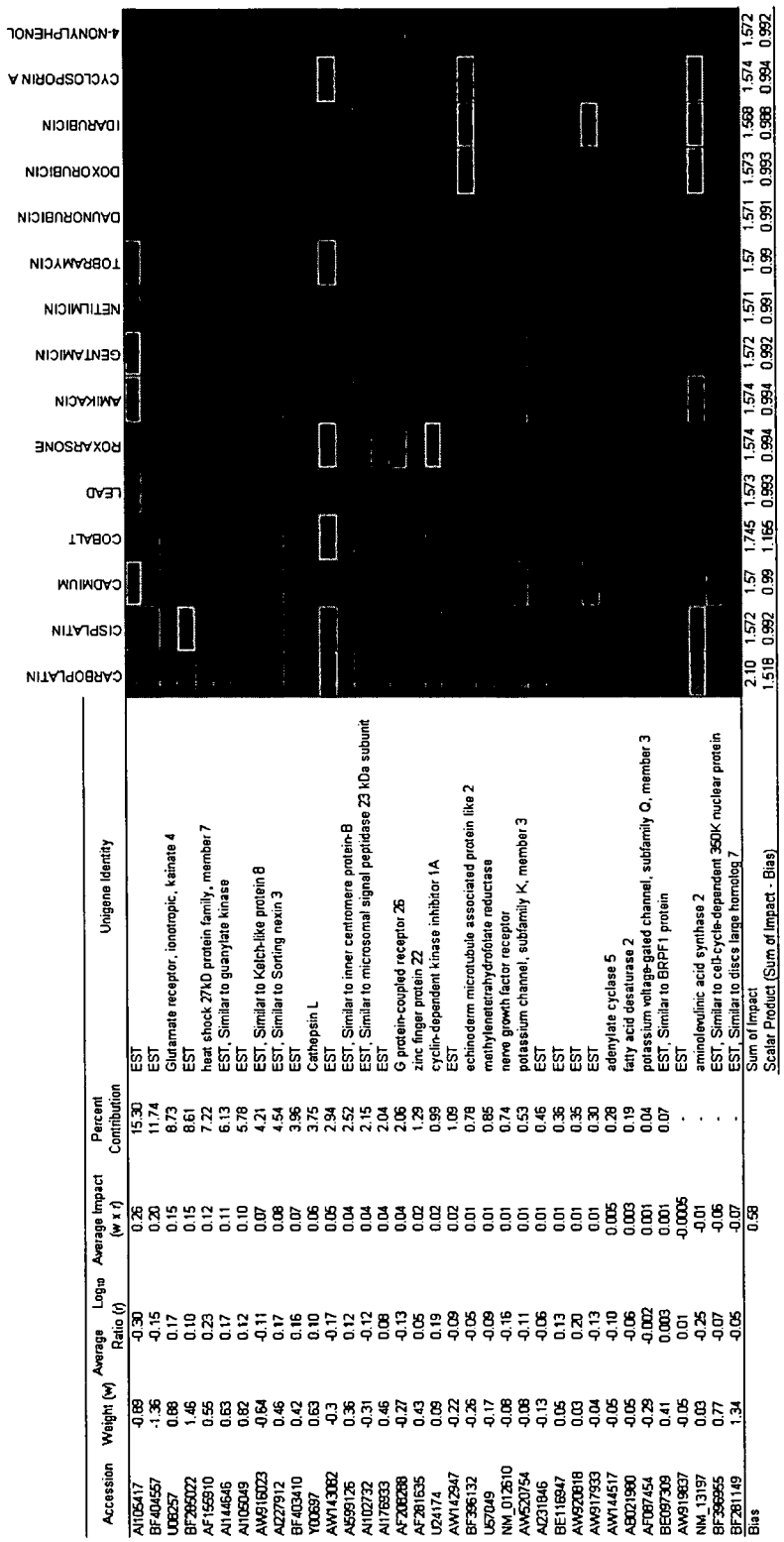
FIG. 1 depicts the 35 genes in the first iteration RTI signature derived according to the method of Example 3, their corresponding weights, and their average expression $\log_{10}$ ratio in the 15 compound training positive class.

The present invention provides methods for predicting whether compound treatments induce future renal tubular injury following sub-chronic or long-term treatment using expression data from sub-acute or short-term treatments. The invention provides necessary and sufficient sets of genes and specific signatures comprising these genes that allow gene expression data to be used to identify the ability of a compound treatment to induce late onset renal tubule injury before the actual histological or clinical indication of the toxicity. Further, the invention provides reagent sets and diagnostic devices comprising the disclosed gene sets and signatures that may be used to deduce compound toxicity using short term studies, and avoiding lengthy and costly long term studies.

II. Definitions

"Multivariate dataset" as used herein, refers to any dataset comprising a plurality of different variables including but not limited to chemogenomic datasets comprising logratios from differential gene expression experiments, such as those carried out on polynucleotide microarrays, or multiple protein binding affinities measured using a protein chip. Other examples of multivariate data include assemblies of data from a plurality of standard toxicological or pharmacological assays (e.g., blood analytes measured using enzymatic assays, antibody based ELISA or other detection techniques).

"Variable" as used herein, refers to any value that may vary. For example, variables may include relative or absolute amounts of biological molecules, such as mRNA or proteins, or other biological metabolites. Variables may also include dosing amounts of test compounds.

"Classifier" as used herein, refers to a function of a set of variables that is capable of answering a classification question. A "classification question" may be of any type susceptible to yielding a yes or no answer (e.g., "Is the unknown a member of the class or does it belong with everything else outside the class?"). "Linear classifiers" refers to classifiers comprising a first order function of a set of variables, for example, a summation of a weighted set of gene expression logratios. A valid classifier is defined as a classifier capable of achieving a performance for its classification task at or above a selected threshold value. For example, a log odds ratio≧4.00 represents a preferred threshold of the present invention. Higher or lower threshold values may be selected depending of the specific classification task.

"Signature" as used herein, refers to a combination of variables, weighting factors, and other constants that provides a unique value or function capable of answering a classification question. A signature may include as few as one variable. Signatures include but are not limited to linear classifiers comprising sums of the product of gene expression logratios by weighting factors and a bias term.

"Weighting factor" (or "weight") as used herein, refers to a value used by an algorithm in combination with a variable in order to adjust the contribution of the variable.

"Impact factor" or "Impact" as used herein in the context of classifiers or signatures refers to the product of the weighting factor by the average value of the variable of interest. For example, where gene expression logratios are the variables, the product of the gene's weighting factor and the gene's measured expression $\log_{10}$ ratio yields the gene's impact. The sum of the impacts of all of the variables (e.g., genes) in a set yields the "total impact" for that set.

"Scalar product" (or "Signature score") as used herein refers to the sum of impacts for all genes in a signature less the bias for that signature. A positive scalar product for a sample indicates that it is positive for (i.e., a member of) the classification that is determined by the classifier or signature.

"Sufficient set" as used herein is a set of variables (e.g., genes, weights, bias factors) whose cross-validated performance for answering a specific classification question is greater than an arbitrary threshold (e.g., a log odds ratio≧4.0).

"Necessary set" as used herein is a set of variables whose removal from the full set of all variables results in a depleted set whose performance for answering a specific classification question does not rise above an arbitrarily defined minimum level (e.g., log odds ratio≧4.00).

"Log odds ratio" or "LOR" is used herein to summarize the performance of classifiers or signatures. LOR is defined generally as the natural log of the ratio of the odds of predicting a subject to be positive when it is positive, versus the odds of predicting a subject to be positive when it is negative. LOR is estimated herein using a set of training or test cross-validation partitions according to the following equation, $$LOR = \ln \frac{\left(\sum_{i=1}^{c} TP_i + 0.5\right) * \left(\sum_{i=1}^{c} TN_i + 0.5\right)}{\left(\sum_{i=1}^{c} FP_i + 0.5\right) * \left(\sum_{i=1}^{c} FN_i + 0.5\right)}$$

where c (typically c=40 as described herein) equals the number of partitions, and $TP_i$, $TN_i$, $FP_i$, and $FN_i$ represent the number of true positive, true negative, false positive, and false negative occurrences in the test cases of the $i^{th}$ partition, respectively.

"Array" as used herein, refers to a set of different biological molecules (e.g., polynucleotides, peptides, carbohydrates, etc.). An array may be immobilized in or on one or more solid substrates (e.g., glass slides, beads, or gels) or may be a collection of different molecules in solution (e.g., a set of PCR primers). An array may include a plurality of biological polymers of a single class (e.g., polynucleotides) or a mixture of different classes of biopolymers (e.g., an array including both proteins and nucleic acids immobilized on a single substrate).

"Array data" as used herein refers to any set of constants and/or variables that may be observed, measured or otherwise derived from an experiment using an array, including but not limited to: fluorescence (or other signaling moiety) intensity ratios, binding affinities, hybridization stringency, temperature, buffer concentrations.

"Proteomic data" as used herein refers to any set of constants and/or variables that may be observed, measured or otherwise derived from an experiment involving a plurality of mRNA translation products (e.g., proteins, peptides, etc) and/or small molecular weight metabolites or exhaled gases associated with these translation products.

III. General Methods of the Invention

The present invention provides a method to derive multiple non-overlapping gene signatures for renal tubule injury. These non-overlapping signatures use different genes and thus each may be used independently in a predictive assay to confirm that an individual will suffer renal tubule injury. Furthermore, this method for identifying non-overlapping gene signatures also provides the list of all genes "necessary" to create a signature that performs above a certain minimal threshold level for a specific predicting renal tubule injury. This necessary set of genes also may be used to derive additional signatures with varying numbers of genes and levels of performance for particular applications (e.g., diagnostic assays and devices).

Classifiers comprising genes as variables and accompanying weighting factors may be used to classify large datasets compiled from DNA microarray experiments. Of particular preference are sparse linear classifiers. Sparse as used here means that the vast majority of the genes measured in the expression experiment have zero weight in the final linear classifier. Sparsity ensures that the sufficient and necessary gene lists produced by the methodology described herein are as short as possible. These short weighted gene lists (i.e., a gene signature) are capable of assigning an unknown compound treatment to one of two classes.

The sparsity and linearity of the classifiers are important features. The linearity of the classifier facilitates the interpretation of the signature—the contribution of each gene to the classifier corresponds to the product of its weight and the value (i.e., $\log_{10}$ ratio) from the micro array experiment. The property of sparsity ensures that the classifier uses only a few genes, which also helps in the interpretation. More importantly, the sparsity of the classifier may be reduced to a practical diagnostic apparatus or device comprising a relatively small set of reagents representing genes.

A. Gene Expression Related Datasets a. Various Useful Data Types

The present invention may be used with a wide range of gene expression related data types to generate necessary and sufficient sets of genes useful for renal tubule injury signatures. In a preferred embodiment, the present invention utilizes data generated by high-throughput biological assays such as DNA microarray experiments, or proteomic assays. The datasets are not limited to gene expression related data but also may include any sort of molecular characterization information including, e.g., spectroscopic data (e.g., UV-Vis, NMR, IR, mass spectrometry, etc.), structural data (e.g., three-dimensional coordinates) and functional data (e.g., activity assays, binding assays). The gene sets and signatures produced by using the present invention may be applied in a multitude of analytical contexts, including the development and manufacture of detection devices (i.e., diagnostics).

b. Construction of a Gene Expression Dataset

The present invention may be used to identify necessary and sufficient sets of responsive genes within a gene expression dataset that are useful for predicting renal tubule injury. In a preferred embodiment, a chemogenomic dataset is used.

For example, the data may correspond to treatments of organisms (e.g., cells, worms, frogs, mice, rats, primates, or humans etc.) with chemical compounds at varying dosages and times followed by gene expression profiling of the organism's transcriptome (e.g., measuring mRNA levels) or proteome (e.g., measuring protein levels). In the case of multicellular organisms (e.g., mammals) the expression profiling may be carried out on various tissues of interest (e.g., liver, kidney, marrow, spleen, heart, brain, intestine). Typically, valid sufficient classifiers or signatures may be generated that answer questions relevant to classifying treatments in a single tissue type. The present specification describes examples of necessary and sufficient gene signatures useful for classifying chemogenomic data in liver tissue. The methods of the present invention may also be used however, to generate signatures in any tissue type. In some embodiments, classifiers or signatures may be useful in more than one tissue type. Indeed, a large chemogenomic dataset, like that exemplified in the present invention may reveal gene signatures in one tissue type (e.g., liver) that also classify pathologies in other tissues (e.g., intestine).

In addition to the expression profile data, the present invention may be useful with chemogenomic datasets including additional data types such as data from classic biochemistry assays carried out on the organisms and/or tissues of interest. Other data included in a large multivariate dataset may include histopathology, pharmacology assays, and structural data for the chemical compounds of interest.

One example of a chemogenomic multivariate dataset particularly useful with the present invention is a dataset based on DNA array expression profiling data as described in U.S. patent publication 2002/0174096 A1, published Nov. 21, 2002 (titled "Interactive Correlation of Compound Information and Genomic Information"), which is hereby incorporated by reference for all purposes. Microarrays are well known in the art and consist of a substrate to which probes that correspond in sequence to genes or gene products (e.g., cDNAs, mRNAs, cRNAs, polypeptides, and fragments thereof), can be specifically hybridized or bound at a known position. The microarray is an array (i.e., a matrix) in which each position represents a discrete binding site for a gene or gene product (e.g., a DNA or protein), and in which binding sites are present for many or all of the genes in an organism's genome.

As disclosed above, a treatment may include but is not limited to the exposure of a biological sample or organism (e.g., a rat) to a drug candidate (or other chemical compound), the introduction of an exogenous gene into a biological sample, the deletion of a gene from the biological sample, or changes in the culture conditions of the biological sample. Responsive to a treatment, a gene corresponding to a microarray site may, to varying degrees, be (a) up-regulated, in which more mRNA corresponding to that gene may be present, (b) down-regulated, in which less mRNA corresponding to that gene may be present, or (c) unchanged. The amount of up-regulation or down-regulation for a particular matrix location is made capable of machine measurement using known methods (e.g., fluorescence intensity measurement). For example, a two-color fluorescence detection scheme is disclosed in U.S. Pat. Nos. 5,474,796 and 5,807,522, both of which are hereby incorporated by reference herein. Single color schemes are also well known in the art, wherein the amount of up- or down-regulation is determined in silico by calculating the ratio of the intensities from the test array divided by those from a control.

After treatment and appropriate processing of the microarray, the photon emissions are scanned into numerical form, and an image of the entire microarray is stored in the form of an image representation such as a color JPEG or TIFF format. The presence and degree of up-regulation or down-regulation of the gene at each microarray site represents, for the perturbation imposed on that site, the relevant output data for that experimental run or scan.

The methods for reducing datasets disclosed herein are broadly applicable to other gene and protein expression data. For example, in addition to microarray data, biological response data including gene expression level data generated from serial analysis of gene expression (SAGE, supra) (Velculescu et al., 1995, Science, 270:484) and related technologies are within the scope of the multivariate data suitable for analysis according to the method of the invention. Other methods of generating biological response signals suitable for the preferred embodiments include, but are not limited to: traditional Northern and Southern blot analysis; antibody studies; chemiluminescence studies based on reporter genes such as luciferase or green fluorescent protein; Lynx; READS (GeneLogic); and methods similar to those disclosed in U.S. Pat. No. 5,569,588 to Ashby et. al., "Methods for drug screening," the contents of which are hereby incorporated by reference into the present disclosure.

In another preferred embodiment, the large multivariate dataset may include genotyping (e.g., single-nucleotide polymorphism) data. The present invention may be used to generate necessary and sufficient sets of variables capable of classifying genotype information. These signatures would include specific high-impact SNPs that could be used in a genetic diagnostic or pharmacogenomic assay.

The method of generating classifiers from a multivariate dataset according to the present invention may be aided by the use of relational database systems (e.g., in a computing system) for storing and retrieving large amounts of data. The advent of high-speed wide area networks and the internet, together with the client/server based model of relational database management systems, is particularly well-suited for meaningfully analyzing large amounts of multivariate data given the appropriate hardware and software computing tools. Computerized analysis tools are particularly useful in experimental environments involving biological response signals (e.g., absolute or relative gene expression levels). Generally, multivariate data may be obtained and/or gathered using typical biological response signals. Responses to biological or environmental stimuli may be measured and analyzed in a large-scale fashion through computer-based scanning of the machine-readable signals, e.g., photons or electrical signals, into numerical matrices, and through the storage of the numerical data into relational databases. For example a large chemogenomic dataset may be constructed as described in U.S. patent publication 2005/0060102, published Mar. 17, 2005, which is hereby incorporated by reference for all purposes.

B. Generating Valid Gene Signatures from a Chemogenomic Dataset a. Mining a Large Chemogenomic Dataset Generally classifiers or signatures are generated (i.e., mined) from a large multivariate dataset by first labeling the full dataset according to known classifications and then applying an algorithm to the full dataset that produces a linear classifier for each particular classification question. Each signature so generated is then cross-validated using a standard split sample procedure.

The initial questions used to classify (i.e., the classification questions) a large multivariate dataset may be of any type susceptible to yielding a yes or no answer. The general form of such questions is: "Is the unknown a member of the class or does it belong with everything else outside the class?" For example, in the area of chemogenomic datasets, classification questions may include "mode-of-action" questions such as "All treatments with drugs belonging to a particular structural class versus the rest of the treatments" or pathology questions such as "All treatments resulting in a measurable pathology versus all other treatments." In the specific case of chemogenomic datasets based on gene expression, it is preferred that the classification questions are further categorized based on the tissue source of the gene expression data. Similarly, it may be helpful to subdivide other types of large data sets so that specific classification questions are limited to particular subsets of data (e.g., data obtained at a certain time or dose of test compound). Typically, the significance of subdividing data within large datasets become apparent upon initial attempts to classify the complete dataset. A principal component analysis of the complete data set may be used to identify the subdivisions in a large dataset (see e.g., U.S. 2003/0180808 A1, published Sep. 25, 2003, which is hereby incorporated by reference herein.) Methods of using classifiers to identify information rich genes in large chemogenomic datasets is also described in U.S. Ser. No. 11/114,998, filed Apr. 25, 2005, which is hereby incorporated by reference herein for all purposes.

Labels are assigned to each individual (e.g., each compound treatment) in the dataset according to a rigorous rule-based system. The +1 label indicates that a treatment falls in the class of interest, while a −1 label indicates that the variable is outside the class. Thus, with respect to the 64 compound treatments shown in Table 2 (see Example 2 below) used in generating an RTI signature, the "nephrotoxic" treatments were labeled +1, whereas the "non-nephrotoxic" were labeled −1. Information used in assigning labels to the various individuals to classify may include annotations from the literature related to the dataset (e.g., known information regarding the compounds used in the treatment), or experimental measurements on the exact same animals (e.g., results of clinical chemistry or histopathology assays performed on the same animal). A more detailed description of the general method for using classification questions to mine a chemogenomic dataset for signatures is described in U.S. Ser. No. 11/149,612, filed Jun. 10, 2005, and PCT/US2005/020695, filed Jun. 10, 2005, each of which is hereby incorporated in its entirety by reference herein.

b. Algorithms for Generating Valid Gene Signatures

Dataset classification may be carried out manually, that is by evaluating the dataset by eye and classifying the data accordingly. However, because the dataset may involve tens of thousands (or more) individual variables, more typically, querying the full dataset with a classification question is carried out in a computer employing any of the well-known data classification algorithms.

In preferred embodiments, algorithms are used to query the full dataset that generate linear classifiers. In particularly preferred embodiments the algorithm is selected from the group consisting of: SPLP, SPLR and SPMPM. These algorithms are based respectively on Support Vector Machines (SVM), Logistic Regression (LR) and Minimax Probability Machine (MPM). They have been described in detail elsewhere (See e.g., El Ghaoui et al., op. cit; Brown, M. P., W. N. Grundy, D. Lin, N. Cristianini, C. W. Sugnet, T. S. Furey, M. Ares, Jr., and D. Haussler, "Knowledge-based analysis of microarray gene expression data by using support vector machines," Proc Natl Acad Sci USA 97: 262-267 (2000)).

Generally, the sparse classification methods SPLP, SPLR, SPMPM are linear classification algorithms in that they determine the optimal hyperplane separating a positive and a negative class. This hyperplane, H can be characterized by a vectorial parameter, w (the weight vector) and a scalar parameter, b (the bias): H={x|w$^T$x+b=0}.

For all proposed algorithms, determining the optimal hyperplane reduces to optimizing the error on the provided training data points, computed according to some loss function (e.g., the "Hinge loss," i.e., the loss function used in 1-norm SVMs; the "LR loss;" or the "MPM loss" augmented with a 1-norm regularization on the signature, w. Regularization helps to provide a sparse, short signature. Moreover, this 1-norm penalty on the signature will be weighted by the average standard error per gene. That is, genes that have been measured with more uncertainty will be less likely to get a high weight in the signature. Consequently, the proposed algorithms lead to sparse signatures, and take into account the average standard error information.

Mathematically, the algorithms can be described by the cost functions (shown below for SPLP, SPLR and SPMPM) that they actually minimize to determine the parameters w and b.

SPLP $$\min_{w,b} \sum_i e_i + \rho \sum_i \sigma_i |w_i| \quad \text{s.t.} \quad y_i(w^T x_i + b) \geq 1 - e_i$$

$$e_i \geq 0, \quad i = 1, \ldots, N$$

The first term minimizes the training set error, while the second term is the 1-norm penalty on the signature w, weighted by the average standard error information per gene given by sigma. The training set error is computed according to the so-called Hinge loss, as defined in the constraints. This loss function penalizes every data point that is closer than "1" to the separating hyperplane H, or is on the wrong side of H. Notice how the hyperparameter rho allows trade-off between training set error and sparsity of the signature w.

SPLR $$\min_{w,b} \sum_i \log(1 + \exp(-y_i(w^T x_i + b))) + \rho \sum_i \sigma_i |w_i|$$

The first term expresses the negative log likelihood of the data (a smaller value indicating a better fit of the data), as usual in logistic regression, and the second term will give rise to a short signature, with rho determining the trade-off between both.

SPMPM $$\min_w \sqrt{w^T \hat{\Gamma}_+ w} + \sqrt{w^T \hat{\Gamma}_- w} + \rho \sum_i \sigma_i |w_i| \quad \text{s.t.} \quad w^T(\hat{x}_+ - \hat{x}_-) = 1$$

Here, the first two terms, together with the constraint are related to the misclassification error, while the third term will induce sparsity, as before. The symbols with a hat are empirical estimates of the covariances and means of the positive and the negative class. Given those estimates, the misclassification error is controlled by determining w and b such that even for the worst-case distributions for the positive and negative class (which we do not exactly know here) with those means and covariances, the classifier will still perform well. More details on how this exactly relates to the previous cost function can be found in e.g., El Ghaoui, L., G. R. G. Lanckriet, and G. Natsoulis, 2003, "Robust classifiers with interval data" Report # UCB/CSD-03-1279. Computer Science Division (EECS), University of California, Berkeley, Calif.

As mentioned above, classification algorithms capable of producing linear classifiers are preferred for use with the present invention. In the context of chemogenomic datasets, linear classifiers may be used to generate one or more valid signatures capable of answering a classification question comprising a series of genes and associated weighting factors. Linear classification algorithms are particularly useful with DNA array or proteomic datasets because they provide simplified signatures useful for answering a wide variety of questions related to biological function and pharmacological/toxicological effects associated with genes or proteins. These signatures are particularly useful because they are easily incorporated into wide variety of DNA- or protein-based diagnostic assays (e.g., DNA microarrays).

However, some classes of non-linear classifiers, so called kernel methods, may also be used to develop short gene lists, weights and algorithms that may be used in diagnostic device development; while the preferred embodiment described here uses linear classification methods, it specifically contemplates that non-linear methods may also be suitable.

Classifications may also be carried using principle component analysis and/or discrimination metric algorithms well-known in the art (see e.g., U.S. 2003/0180808 A1, published Sep. 25, 2003, which is hereby incorporated by reference herein).

Additional statistical techniques, or algorithms, are known in the art for generating classifiers. Some algorithms produce linear classifiers, which are convenient in many diagnostic applications because they may be represented as a weighted list of variables. In other cases non-linear classifier functions of the initial variables may be used. Other types of classifiers include decision trees and neural networks. Neural networks are universal approximators (Hornik, K., M. Stinchcombe, and H. White. 1989. "Multilayer feedforward networks are universal approximators," Neural Networks 2: 359-366); they can approximate any measurable function arbitrarily well, and they can readily be used to model classification functions as well. They perform well on several biological problems, e.g., protein structure prediction, protein classification, and cancer classification using gene expression data (see, e.g., Bishop, C. M. 1996. Neural Networks for Pattern Recognition. Oxford University Press; Khan, J., J. S. Wei, M. Ringner, L. H. Saal, M. Ladanyi, F. Westermann, F. Berthold, M. Schwab, C. R. Antonescu, C. Peterson, and P. S. Meltzer. 2001. Classification and diagnostic prediction of cancers using gene expression profiling and artificial neural networks. Nat Med 7: 673-679; Wu, C. H., M. Berry, S. Shivakumar, and J. McLarty. 1995. Neural networks for full-scale protein sequence classification: sequence encoding with singular value decomposition. Machine Learning 21: 177-193).

c. Cross-Validation of Gene Signatures

Cross-validation of a gene signature's performance is an important step for determining whether the signature is sufficient. Cross-validation may be carried out by first randomly splitting the full dataset (e.g., a 60/40 split). A training signature is derived from the training set composed of 60% of the samples and used to classify both the training set and the remaining 40% of the data, referred to herein as the test set. In addition, a complete signature is derived using all the data. The performance of these signatures can be measured in terms of log odds ratio (LOR) or the error rate (ER) defined as:

$LOR = \ln(((TP+0.5)*(TN+0.5))/((FP+0.5)*(FN+0.5)))$ and $ER = (FP+FN)/N;$ where TP, TN, FP, FN, and N are true positives, true negatives, false positives, false negatives, and total number of samples to classify, respectively, summed across all the cross validation trials. The performance measures are used to characterize the complete signature, the average of the training or the average of the test signatures.

The SVM algorithms described above are capable of generating a plurality of gene signatures with varying degrees of performance for the classification task. In order to identify that signatures that are to be considered "valid," a threshold performance is selected for the particular classification question. In one preferred embodiment, the classifier threshold performance is set as log odds ratio greater than or equal to 4.00 (i.e., $LOR \geq 4.00$). However, higher or lower thresholds may be used depending on the particular dataset and the desired properties of the signatures that are obtained. Of course many queries of a chemogenomic dataset with a classification question will not generate a valid gene signature.

Two or more valid gene signatures may be generated that are redundant or synonymous for a variety of reasons. Different classification questions (i.e., class definitions) may result in identical classes and therefore identical signatures. For instance, the following two class definitions define the exact same treatments in the database: (1) all treatments with molecules structurally related to statins; and (2) all treatments with molecules having an $IC_{50} < 1$ µM for inhibition of the enzyme HMG CoA reductase.

In addition, when a large dataset is queried with the same classification question using different algorithms (or even the same algorithm under slightly different conditions) different, valid signatures may be obtained. These different signatures may or may not comprise overlapping sets of variables; however, they each can accurately identify members of the class of interest.

For example, as illustrated in Table 1, two equally performing gene signatures (LOR=~7.0) for the fibrate class of compounds may be generated by querying a chemogenomic dataset with two different algorithms: SPLP and SPLR. Genes are designated by their accession number and a brief description. The weights associated with each gene are also indicated. Each signature was trained on the exact same 60% of the multivariate dataset and then cross validated on the exact same remaining 40% of the dataset. Both signatures were shown to exhibit the exact same level of performance as classifiers: two errors on the cross validation data set. The SPLP derived signature consists of 20 genes. The SPLR derived signature consists of eight genes. Only three of the genes from the SPLP signature are present in the eight gene SPLR signature.

TABLE 1

Two Gene Signatures for the Fibrate Class of Drugs

| | Accession | Weight | Unigene name |
|---|---|---|---|
| RLPC | K03249 | 1.1572 | enoyl-Co A, hydratase/3-hydroxyacyl Co A dehydrogenase |
| | AW916833 | 1.0876 | hypothetical protein RMT-7 |
| | BF387347 | 0.4769 | ESTs |
| | BF282712 | 0.4634 | ESTs |
| | AF034577 | 0.3684 | pyruvate dehydrogenate kinase 4 |
| | NM_019292 | 0.3107 | carbonic anhydrase 3 |
| | AI179988 | 0.2735 | ectodermal-neural cortex (with BTB-like domain) |
| | AI715955 | 0.211 | Stac protein (SRC homology 3 and cysteine-rich domain protein) |
| | BE110695 | 0.2026 | activating transcription factor 1 |
| | J03752 | 0.0953 | microsomal glutathione S-transferase 1 |
| | D86580 | 0.0731 | nuclear receptor subfamily 0, group B, member 2 |
| | BF550426 | 0.0391 | KDEL (Lys-Asp-Glu-Leu) endoplasmic reticulum protein retention receptor 2 |
| | AA818999 | 0.0296 | muscleblind-like 2 |
| | NM_019125 | 0.0167 | probasin |
| | AF150082 | −0.0141 | translocase of inner mitochondrial membrane 8 (yeast) homolog A |
| | BE118425 | −0.0781 | Arsenical pump-driving ATPase |
| | NM_017136 | −0.126 | squalene epoxidase |
| | AI171367 | −0.3222 | HSPC154 protein |
| | NM_019369 | −0.637 | inter alpha-trypsin inhibitor, heavy chain 4 |
| | AI137259 | −0.7962 | ESTs |
| SPLR | NM_017340 | 5.3688 | acyl-coA oxidase |
| | BF282712 | 4.1052 | ESTs |
| | NM_012489 | 3.8462 | acetyl-Co A acyltransferase 1 (peroxisomal 3-oxoacyl-Co A thiolase) |
| | BF387347 | 1.767 | ESTs |
| | K03249 | 1.7524 | enoyl-Co A, hydratase/3-hydroxyacyl Co A dehydrogenase |
| | NM_016986 | 0.0622 | acetyl-co A dehydrogenase, medium chain |
| | AB026291 | −0.7456 | acetoacetyl-CoA synthetase |
| | AI454943 | −1.6738 | likely ortholog of mouse porcupine homolog |

It is interesting to note that only three genes are common between these two signatures, (K03249, BF282712, and BF387347) and even those are associated with different weights. While many of the genes may be different, some commonalities may nevertheless be discerned. For example, one of the negatively weighted genes in the SPLP derived signature is NM_017136 encoding squalene epoxidase, a well-known cholesterol biosynthesis gene. Squalene epoxidase is not present in the SPLR derived signature but acetoacteylCoA synthetase, another cholesterol biosynthesis gene is present and is also negatively weighted.

Additional variant signatures may be produced for the same classification task. For example, the average signature length (number of genes) produced by SPLP and SPLR, as well as the other algorithms, may be varied by use of the parameter p (see e.g., El Ghaoui, L., G. R. G. Lanckriet, and G. Natsoulis, 2003, "Robust classifiers with interval data" *Report # UCB/CSD*-03-1279. Computer Science Division (EECS), University of California, Berkeley, Calif.; and PCT publication WO 2005/017807 A2, published Feb. 24, 2005, each of which is hereby incorporated by reference herein). Varying ρ can produce signatures of different length with comparable test performance (Natsoulis et al., "Classification of a large microarray data set: Algorithm comparison and analysis of drug signatures," *Gen. Res.* 15:724-736 (2005)). Those signatures are obviously different and often have no common genes between them (i.e., they do not overlap in terms of genes used).

C. "Stripping" Signatures from a Dataset to Generate the "Necessary" Set

Each individual classifier or signature is capable of classifying a dataset into one of two categories or classes defined by the classification question. Typically, an individual signature with the highest test log odds ratio will be considered as the best classifier for a given task. However, often the second, third (or lower) ranking signatures, in terms of performance, may be useful for confirming the classification of compound treatment, especially where the unknown compound yields a borderline answer based on the best classifier. Furthermore, the additional signatures may identify alternative sources of informational rich data associated with the specific classification question. For example, a slightly lower ranking gene signature from a chemogenomic dataset may include those genes associated with a secondary metabolic pathway affected by the compound treatment. Consequently, for purposes of fully characterizing a class and answering difficult classification questions, it is useful to define the entire set of variables that may be used to produce the plurality of different classifiers capable of answering a given classification question. This set of variables is referred to herein as a "necessary set." Conversely, the remaining variables from the full dataset are those that collectively cannot be used to produce a valid classifier, and therefore are referred to herein as the "depleted set."

The general method for identifying a necessary set of variables useful for a classification question involved what is referred to herein as a classifier "stripping" algorithm. The stripping algorithm comprises the following steps: (1) querying the full dataset with a classification question so as to generate a first linear classifier capable of performing with a log odds ratio greater than or equal to 4.0 comprising a first set of variables; (2) removing the variables of the first linear classifier from the full dataset thereby generating a partially depleted dataset; (3) re-querying the partially depleted dataset with the same classification question so as to generate a second linear classifier and cross-validating this second classifier to determine whether it performs with a log odds ratio greater than or equal to 4. If it does not, the process stops and the dataset is fully depleted for variables capable of generating a classifier with an average log odds ratio greater than or equal to 4.0. If the second classifier is validated as performing with a log odds ratio greater than or equal to 4.0, then its variables are stripped from the full dataset and the partially depleted set if re-queried with the classification question. These cycles of stripping and re-querying are repeated until the performance of any remaining set of variables drops below an arbitrarily set LOR. The threshold at which the iterative process is stopped may be arbitrarily adjusted by the user depending on the desired outcome. For example, a user may choose a threshold of LOR=0. This is the value expected by chance alone. Consequently, after repeated stripping until LOR=0 there is no classification information remaining in the depleted set. Of course, selecting a lower value for the threshold will result in a larger necessary set.

Although a preferred cut-off for stripping classifiers is LOR=4.0, this threshold is arbitrary. Other embodiments within the scope of the invention may utilize higher or lower stripping cutoffs e.g., depending on the size or type of dataset, or the classification question being asked. In addition other metrics could be used to assess the performance (e.g., specificity, sensitivity, and others). Also the stripping algorithm removes all variables from a signature if it meets the cutoff. Other procedures may be used within the scope of the invention wherein only the highest weighted or ranking variables are stripped. Such an approach based on variable impact would likely result in a classifier "surviving" more cycles and defining a smaller necessary set.

Other procedures may be used within the scope of the invention wherein only the highest weighted or ranking variables are stripped. Such an approach based on variable impact would likely result in a classifier "surviving" more cycles and defining a smaller necessary set.

In another alternative approach, the genes from signatures may be stripped from the dataset until it is unable to generate a signature capable of classifying the "true label set" with an LOR that is statistically different from its classification of the "random label set." The "true label set" refers to a training set of compound treatment data that is correctly labeled (e.g., +1 class, −1 class) for the particular classification question. The "random label set" refers to the same set of compound treatment data where the class labels have been randomly assigned. Attempts to use a signature to classify a random label set will result in an average LOR of approximately zero and some standard deviation (SD). These values may be compared to the average LOR and SD for the classifying the true label set, where the SD is calculated based on LOR results across the 20 or 40 splits. The difference in classifying true and random label sets with valid signatures should be significantly greater than random. In such an alternative approach, the selected performance threshold for a signature is a p-value rather than a LOR cutoff.

The resulting fully-depleted set of variables that remains after a classifier is fully stripped from the full dataset cannot generate a classifier for the specific classification question (with the desired level of performance). Consequently, the set of all of the variables in the classifiers that were stripped from the full set are defined as "necessary" for generating a valid classifier.

The stripping method utilizes a classification algorithm at its core. The examples presented here use SPLP for this task. Other algorithms, provided that they are sparse with respect to genes could be employed. SPLR and SPMPM are two alternatives for this functionality (see e.g., El Ghaoui, L., G. R. G. Lanckriet, and G. Natsoulis, 2003, "Robust classifiers with interval data" *Report # UCB/CSD*-03-1279. Computer Science Division (EECS), University of California, Berkeley, Calif., and PCT publication WO 2005/017807 A2, published Feb. 24, 2005, which is hereby incorporated by reference herein).

In one embodiment, the stripping algorithm may be used on a chemogenomics dataset comprising DNA microarray data. The resulting necessary set of genes comprises a subset of highly informative genes for a particular classification question. Consequently, these genes may be incorporated in diagnostic devices (e.g., polynucleotide arrays) where that particular classification (e.g., renal tubule injury) is of interest. In other exemplary embodiments, the stripping method may be used with datasets from proteomic experiments.

D. Mining the Renal Tubule Injury Necessary Set for Signatures

Besides identifying the "necessary" set of genes for a particular signature (i.e., classifier), another important use of the stripping algorithm is the identification of multiple, non-overlapping sufficient sets of genes useful for answering a particular classification question. These non-overlapping sufficient sets are a direct product of the above-described general method of stripping valid classifiers. Where the application of the method results in a second validated classifier with the desired level of performance, that second classifier by definition does not include any genes in common with the first classifier. Typically, the earlier stripped non-overlapping gene signature yields higher performance with fewer genes. In other words, the earliest identified sufficient set usually comprises the highest impact, most information-rich genes with respect to the particular classification question. The valid classifiers that appear during later iterations of the stripping algorithm typically contain a larger number of genes. However, these later appearing classifiers may provide valuable information regarding normally unrecognized relationships between genes in the dataset. For example, in the case of non-overlapping gene signatures identified by stripping in a chemogenomics dataset, the later appearing signatures may include families of genes not previously recognized as involved in the particular metabolic pathway that is being affected by a particular compound treatment. Thus, functional analysis of a gene signature stripping procedure may identify new metabolic targets associated with a compound treatment.

The necessary set high impact genes generated by the stripping method itself represents a subset of genes that may be mined for further signatures. Hence, the complete set of genes in a necessary set for predicting renal tubule injury may used to randomly generate random subsets of genes of varying size that are capable of generating additional predictive signatures. One preferred method of selecting such subsets is based on percentage of total impact. Thus, subsets of genes are selected whose summed impact factors are a selected percentage of the total impact (i.e., the sum of the impacts of all genes in the necessary set). These percentage impact subsets may be used to generate new signatures for predicting renal tubule injury. For example, a random subset from the necessary set of 9 genes with 4% of the total impact may be used with one of the SVM algorithms to generate a new linear classifier of 8 genes, weighting factors and a bias term that may be used as a signature for renal tubule injury. Thus, the necessary set for a particular classification represents a greatly reduced dataset that can generate new signatures with varying properties such as shorter (or longer) gene lengths and higher (or lower) LOR performance values.

E. Functional Characterization of the Renal Tubule Injury Necessary Set

The stripping method described herein produces a necessary set of genes representing for answering the RTI classification question. The RTI necessary set of genes also may be characterized in functional terms based on the ability of the information rich genes in the set to supplement (i.e., "revive") the ability of a fully "depleted" set of genes to generate valid RTI signatures. Thus, the necessary set for the RTI classification question corresponds to that set of genes from which any random selection when added to a depleted set (i.e., depleted for RTI classification question) restores the ability of that set to produce RTI signatures with an average LOR (avg. LOR) above a threshold level. The general method for functionally characterizing a necessary set in terms of its ability to revive its depleted set is described in U.S. Ser. No. 11/149,612, filed Jun. 10, 2005, and PCT/US2005/020695, filed Jun. 10, 2005, each of which is hereby incorporated in its entirety by reference herein.

Preferably, the threshold performance used is an avg. LOR greater than or equal to 4.00. Other values for performance, however, may be set. For example, avg. LOR may vary from about 1.0 to as high as 8.0. In preferred embodiments, the avg. LOR threshold may be 3.0 to as high as 7.0 including all integer and half-integer values in that range. The necessary set may then be defined in terms of percentage of randomly selected genes from the necessary set that restore the performance of a depleted set above a certain threshold. Typically, the avg. LOR of the depleted set is ~1.20, although as mentioned above, datasets may be depleted more or less depending on the threshold set, and depleted sets with avg. LOR as low as 0.0 may be used. Generally, the depleted set will exhibit an avg. LOR between about 0.5 and 1.5.

The third parameter establishing the functional characteristics of the RTI necessary set of genes for answering the RTI classification question is the percentage of randomly selected genes from that set that result in reviving the threshold performance of the depleted set. Typically, where the threshold avg. LOR is at least 4.00 and the depleted set performs with an avg. LOR of ~1.20, typically 16-36% of randomly selected genes from the necessary set are required to restore the average performance of the depleted set to the threshold value. In preferred embodiments, the random supplementation may be achieved using 16, 18, 20, 22, 24, 26, 28, 30, 32, 34 or 36% of the necessary set.

Alternatively, as described above, the necessary set may be characterized based on its ability to randomly generate signatures capable of classifying a true label set with an average performance above those signatures ability to classify a random label set. In preferred embodiments, signatures generated from a random selection of at least 10% of the genes in the necessary set may perform at least 1 standard deviation, and preferably at least 2 standard deviations, better for classifying the true versus the random label set. In other embodiments, the random selection may be of at least 15%, 20%, 25%, 30%, 40%, 50%, and even higher percentages of genes from the set.

F. Using Signatures and the Necessary Set to Generate Diagnostic Assays and Devices for Predicting Renal Tubule Injury A diagnostic usually consists in performing one or more assays and in assigning a sample to one or more categories based on the results of the assay(s). Desirable attributes of a diagnostic assays include high sensitivity and specificity measured in terms of low false negative and false positive rates and overall accuracy. Because diagnostic assays are often used to assign large number of samples to given categories, the issues of cost per assay and throughput (number of assays per unit time or per worker hour) are of paramount importance.

Typically the development of a diagnostic assay involves the following steps: (1) define the end point to diagnose, e.g., cholestasis, a pathology of the liver (2) identify one or more markers whose alteration correlates with the end point, e.g., elevation of bilirubin in the bloodstream as an indication of cholestasis; and (3) develop a specific, accurate, high-throughput and cost-effective assay for that marker. In order to increase throughput and decrease costs several diagnostics are often combined in a panel of assays, especially when the detection methodologies are compatible. For example several ELISA-based assays, each using different antibodies to ascertain different end points may be combined in a single panel and commercialized as a single kit. Even in this case, however, each of the ELISA-based assays had to be developed individually often requiring the generation of specific reagents.

The present invention provides signatures and methods for identifying additional signatures comprising as few as 4 genes that are useful for determining a therapeutic or toxicological end-point for renal tubule injury. These signatures (and the genes from which they are composed) may also be used in the design of improved diagnostic devices that answer the same questions as a large microarray but using a much smaller fraction of data. Generally, the reduction of information in a large chemogenomic dataset to a simple signature enables much simpler devices compatible with low cost high throughput multi-analyte measurement.

As described herein, a large chemogenomic dataset may be mined for a plurality of informative genes useful for answering classification questions. The size of the classifiers or signatures so generated may be varied according to experimental needs. In addition, multiple non-overlapping classifiers may be generated where independent experimental measures are required to confirm a classification. Generally, the sufficient classifiers result in a substantial reduction of data that needs to be measured to classify a sample. Consequently, the signatures and methods of the present invention provide the ability to produce cheaper, higher throughput, diagnostic measurement methods or strategies. In particular, the invention provides diagnostic reagent sets useful in diagnostic assays and the associated diagnostic devices and kits. As used herein, diagnostic assays includes assays that may be used for patient prognosis and therapeutic monitoring.

Diagnostic reagent sets may include reagents representing the subset of genes found in the necessary set of 186 consisting of less than 50%, 40%, 30%, 20%, 10%, or even less than 5% of the total genes. In one preferred embodiment, the diagnostic reagent set is a plurality of polynucleotides or polypeptides representing specific genes in a sufficient or necessary set of the invention. Such biopolymer reagent sets are immediately applicable in any of the diagnostic assay methods (and the associate kits) well known for polynucleotides and polypeptides (e.g., DNA arrays, RT-PCR, immunoassays or other receptor based assays for polypeptides or proteins). For example, by selecting only those genes found in a smaller yet "sufficient" gene signature, a faster, simpler and cheaper DNA array may be fabricated for that signature's specific classification task. Thus, a very simple diagnostic array may be designed that answers 3 or 4 specific classification questions and includes only 60-80 polynucleotides representing the approximately 20 genes in each of the signatures. Of course, depending on the level of accuracy required the LOR threshold for selecting a sufficient gene signature may be varied. A DNA array may be designed with many more genes per signature if the LOR threshold is set at e.g., 7.00 for a given classification question. The present invention includes diagnostic devices based on gene signatures exhibiting levels of performance varying from less than LOR=3.00 up to LOR=10.00 and greater.

The diagnostic reagent sets of the invention may be provided in kits, wherein the kits may or may not comprise additional reagents or components necessary for the particular diagnostic application in which the reagent set is to be employed. Thus, for a polynucleotide array applications, the diagnostic reagent sets may be provided in a kit which further comprises one or more of the additional requisite reagents for amplifying and/or labeling a microarray probe or target (e.g., polymerases, labeled nucleotides, and the like).

A variety of array formats (for either polynucleotides and/or polypeptides) are well-known in the art and may be used with the methods and subsets produced by the present invention. In one preferred embodiment, photolithographic or micromirror methods may be used to spatially direct light-induced chemical modifications of spacer units or functional groups resulting in attachment at specific localized regions on the surface of the substrate. Light-directed methods of controlling reactivity and immobilizing chemical compounds on solid substrates are well-known in the art and described in U.S. Pat. Nos. 4,562,157, 5,143,854, 5,556,961, 5,968,740, and 6,153,744, and PCT publication WO 99/42813, each of which is hereby incorporated by reference herein.

Alternatively, a plurality of molecules may be attached to a single substrate by precise deposition of chemical reagents. For example, methods for achieving high spatial resolution in depositing small volumes of a liquid reagent on a solid substrate are disclosed in U.S. Pat. Nos. 5,474,796 and 5,807,522, both of which are hereby incorporated by reference herein.

It should also be noted that in many cases a single diagnostic device may not satisfy all needs. However, even for an initial exploratory investigation (e.g., classifying drug-treated rats) DNA arrays with sufficient gene sets of varying size (number of genes), each adapted to a specific follow-up technology, can be created. In addition, in the case of drug-treated rats, different arrays may be defined for each tissue.

Alternatively, a single substrate may be produced with several different small arrays of genes in different areas on the surface of the substrate. Each of these different arrays may represent a sufficient set of genes for the same classification question but with a different optimal gene signature for each different tissue. Thus, a single array could be used for particular diagnostic question regardless of the tissue source of the sample (or even if the sample was from a mixture of tissue sources, e.g., in a forensic sample).

In addition, it may be desirable to investigate classification questions of a different nature in the same tissue using several arrays featuring different non-overlapping gene signatures for a particular classification question.

As described above, the methodology described here is not limited to chemogenomic datasets and DNA microarray data. The invention may be applied to other types of datasets to produce necessary and sufficient sets of variables useful for classifiers. For example, proteomics assay techniques, where protein levels are measured or protein interaction techniques such as yeast 2-hybrid or mass spectrometry also result in large, highly multivariate dataset, which could be classified in the same way described here. The result of all the classification tasks could be submitted to the same methods of signature generation and/or classifier stripping in order to define specific sets of proteins useful as signatures for specific classification questions.

In addition, the invention is useful for many traditional lower throughput diagnostic applications. Indeed the invention teaches methods for generating valid, high-performance classifiers consisting of 5% or less of the total variables in a dataset. This data reduction is critical to providing a useful analytical device. For example, a large chemogenomic dataset may be reduced to a signature comprising less than 5% of the genes in the full dataset. Further reductions of these genes may be made by identifying only those genes whose product is a secreted protein. These secreted proteins may be identified based on known annotation information regarding the genes in the subset. Because the secreted proteins are identified in the sufficient set useful as a signature for a particular classification question, they are most useful in protein based diagnostic assays related to that classification. For example, an antibody-based blood serum assay may be produced using the subset of the secreted proteins found in the sufficient signature set. Hence, the present invention may be used to generate improved protein-based diagnostic assays from DNA array information.

The general method of the invention as described above is exemplified below. The following examples are offered as illustrations of specific embodiments and are not intended to limit the inventions disclosed throughout the whole of the specification.

EXAMPLES

Example 1

Construction of Chemogenomic Reference Database (DrugMatrix™)

This example illustrates the construction of a large multivariate chemogenomic dataset based on DNA microarray analysis of rat tissues from over 580 different in vivo compound treatments. This dataset was used to generate RTI signatures comprising genes and weights which subsequently were used to generate a necessary set of highly responsive genes that may be incorporated into high throughput diagnostic devices as described in Examples 2-7.

The detailed description of the construction of this chemogenomic dataset is described in Examples 1 and 2 of Published U.S. Pat. Appl. No. 2005/0060102 A1, published Mar. 17, 2005, which is hereby incorporated by reference for all purposes. Briefly, in vivo short-term repeat dose rat studies were conducted on over 580 test compounds, including marketed and withdrawn drugs, environmental and industrial toxicants, and standard biochemical reagents. Rats (three per group) were dosed daily at either a low or high dose. The low dose was an efficacious dose estimated from the literature and the high dose was an empirically-determined maximum tolerated dose, defined as the dose that causes a 50% decrease in body weight gain relative to controls during the course of the 5 day range finding study. Animals were necropsied on days 0.25, 1, 3, and 5 or 7. Up to 13 tissues (e.g., liver, kidney, heart, bone marrow, blood, spleen, brain, intestine, glandular and nonglandular stomach, lung, muscle, and gonads) were collected for histopathological evaluation and microarray expression profiling on the Amersham CodeLink™ RU1 platform. In addition, a clinical pathology panel consisting of 37 clinical chemistry and hematology parameters was generated from blood samples collected on days 3 and 5.

In order to assure that all of the dataset is of high quality a number of quality metrics and tests are employed. Failure on any test results in rejection of the array and exclusion from the data set. The first tests measure global array parameters: (1) average normalized signal to background, (2) median signal to threshold, (3) fraction of elements with below background signals, and (4) number of empty spots. The second battery of tests examines the array visually for unevenness and agreement of the signals to a tissue specific reference standard formed from a number of historical untreated animal control arrays (correlation coefficient>0.8). Arrays that pass all of these checks are further assessed using principle component analysis versus a dataset containing seven different tissue types; arrays not closely clustering with their appropriate tissue cloud are discarded.

Data collected from the scanner is processed by the Dewarping/Detrending™ normalization technique, which uses a non-linear centralization normalization procedure (see, Zien, A., T. Aigner, R. Zimmer, and T. Lengauer. 2001. Centralization: A new method for the normalization of gene expression data. *Bioinformatics*) adapted specifically for the CodeLink microarray platform. The procedure utilizes detrending and dewarping algorithms to adjust for non-biological trends and non-linear patterns in signal response, leading to significant improvements in array data quality.

$Log_{10}$-ratios are computed for each gene as the difference of the averaged logs of the experimental signals from (usually) three drug-treated animals and the averaged logs of the control signals from (usually) 20 mock vehicle-treated animals. To assign a significance level to each gene expression change, the standard error for the measured change between the experiments and controls is computed. An empirical Bayesian estimate of standard deviation for each measurement is used in calculating the standard error, which is a weighted average of the measurement standard deviation for each experimental condition and a global estimate of measurement standard deviation for each gene determined over thousands of arrays (Carlin, B. P. and T. A. Louis. 2000. "*Bayes and empirical Bayes methods for data analysis*," Chapman & Hall/CRC, Boca Raton; Gelman, A. 1995. "*Bayesian data analysis*," Chapman & Hall/CRC, Boca Raton). The standard error is used in a t-test to compute a p-value for the significance of each gene expression change. The coefficient of variation (CV) is defined as the ratio of the standard error to the average $Log_{10}$-ratio, as defined above.

Example 2

Preparation of a Chemogenomic Dataset for Late-Onset Renal Tubule Injury

This example describes methods used to prepare a chemogenomic dataset (i.e., a positive training set) for use deriving a signature for renal tubule injury (i.e., late-onset nephrotoxicity).

Overview 28-day repeat dose studies were conducted on known nephrotoxicants. Doses were chosen that would not cause histological or clinical evidence of renal tubular injury after 5 days of dosing, but would cause histological evidence of tubular injury after 28 days of dosing. Animals were assigned to groups such that mean body weights were within 10% of the mean vehicle control group. Test compounds were administered either orally (10 ml of corn oil/kg body weight) or by intra-peritoneal injection (5 ml of saline/kg body weight). Animals were dosed once daily starting on day 0, and necropsied 24 hrs after the last dose following an overnight fast on day 5 (n=5) and day 28 (n=10). An equivalent number of time- and vehicle-matched control rats were treated concurrently. Likewise, a large set of short-term (day 5/7) treatments that would not cause renal tubular injury (i.e., negative control data) after sub-chronic dosing conditions were selected from the chemogenomic reference database in-vivo studies described in Example 1 (above), to complete the training set. This assertion of the absence of nephrotoxicity for these compounds was based on thorough evaluation of human clinical studies curated in Physicians Desk Reference (PDR) as well as peer-reviewed published literature. Lastly, these treatments did not cause histological evidence of renal tubular injury on day 5/7. Appropriate time and vehicle-matched controls for these negative treatments were also derived from the reference database in vivo studies described in Example 1.

Compound Selection and Dosing

To derive a signature predictive of renal tubular injury, it is necessary to first define both nephrotoxic and non-nephrotoxic treatments from short-term studies devoid of tissue injury that can be used to model the early transcriptional effects that will be predictive of late-onset toxicity. To empirically confirm the late-onset nephrotoxicity of the positive treatments prior to inclusion in the training set, 28-day repeat dose studies were conducted on 15 known nephrotoxicants in adult male Sprague-Dawley rats according to the in vivo methods described in Example 1.

In addition, 49 short-term (day 5/7) compound treatments that would not cause renal tubular injury after sub-chronic dosing conditions were selected from chemogenomic reference database (DrugMatrix™) to complete the training set. This assertion of the absence of nephrotoxicity for these compounds was based on thorough evaluation of human clinical studies curated in Physicians Desk Reference (PDR) as well as peer-reviewed published literature. These treatments were experimentally confirmed not to cause histological evidence of renal tubular injury at the time of expression analysis.

Doses were chosen that would not cause histological or clinical evidence of renal tubular injury after 5 days of dosing, but would cause histological evidence of tubular injury after 28 days of dosing. This time course of injury was significant to deriving a predictive signature since the presence of injury on day 5 would bias the signature towards a gene expression pattern that are indicative of the presence of a lesion, rather than identifying gene expression events that will predict the future occurrence of the lesion.

The compounds and their doses are listed in Table 2.

TABLE 2

64 in vivo compound treatments used in the training set.

| Compound | Dose (mg/kg/d) | Time (d) | Vehicle | Route | Class |
|---|---|---|---|---|---|
| 4-NONYLPHENOL | 200 | 5 | Corn oil | PO | Nephrotoxic |
| AMIKACIN | 160 | 5 | Saline | IP | Nephrotoxic |
| CADMIUM CHLORIDE | 2 | 5 | Saline | IP | Nephrotoxic |
| CARBOPLATIN | 5 | 5 | Saline | IP | Nephrotoxic |
| CISPLATIN | 0.5 | 5 | Saline | IP | Nephrotoxic |
| COBALT (II) CHLORIDE | 10 | 5 | Saline | IP | Nephrotoxic |
| CYCLOSPORIN A | 70 | 5 | Corn oil | PO | Nephrotoxic |
| DAUNORUBICIN | 4 | 5 | Saline | IV | Nephrotoxic |
| DOXORUBICIN | 4 | 5 | Saline | IV | Nephrotoxic |
| GENTAMICIN | 40 | 5 | Saline | IP | Nephrotoxic |
| IDARUBICIN | 4 | 5 | Saline | IV | Nephrotoxic |
| LEAD (II) ACETATE | 2 | 5 | Saline | IP | Nephrotoxic |
| NETILMICIN | 40 | 5 | Saline | IP | Nephrotoxic |
| ROXARSONE | 11 | 5 | Corn oil | PO | Nephrotoxic |
| TOBRAMYCIN | 40 | 5 | Saline | IP | Nephrotoxic |
| 6-METHOXY-2-NAPHTHYLACETIC ACID | 360 | 5 | Saline | PO | Non-nephrotoxic |
| ACARBOSE | 2000 | 5 | Water | PO | Non-nephrotoxic |
| AMPRENAVIR | 600 | 5 | CMC | PO | Non-nephrotoxic |
| ANTIPYRINE | 1500 | 5 | CMC | PO | Non-nephrotoxic |
| ASPIRIN | 375 | 5 | Corn oil | PO | Non-nephrotoxic |
| ATORVASTATIN | 300 | 5 | Corn oil | PO | Non-nephrotoxic |
| AZATHIOPRINE | 54 | 5 | Water | PO | Non-nephrotoxic |
| BENAZEPRIL | 1750 | 5 | CMC | PO | Non-nephrotoxic |
| BETAHISTINE | 1500 | 5 | Water | PO | Non-nephrotoxic |
| BISPHENOL A | 610 | 5 | Corn oil | PO | Non-nephrotoxic |
| BITHIONOL | 333 | 5 | Corn oil | PO | Non-nephrotoxic |
| CANDESARTAN | 1300 | 5 | CMC | PO | Non-nephrotoxic |
| CAPTOPRIL | 1750 | 5 | Water | PO | Non-nephrotoxic |
| CELECOXIB | 263 | 5 | Corn oil | PO | Non-nephrotoxic |
| CLINDAMYCIN | 161 | 5 | Saline | IV | Non-nephrotoxic |
| CLOFIBRATE | 500 | 7 | Corn oil | PO | Non-nephrotoxic |
| CROMOLYN | 1500 | 5 | Water | PO | Non-nephrotoxic |
| DEXIBUPROFEN | 239 | 5 | CMC | PO | Non-nephrotoxic |
| ENROFLOXACIN | 2000 | 5 | CMC | PO | Non-nephrotoxic |
| ETHANOL | 6000 | 7 | Saline | PO | Non-nephrotoxic |
| EUCALYPTOL | 930 | 5 | Corn oil | PO | Non-nephrotoxic |
| FENOFIBRATE | 215 | 5 | Corn oil | PO | Non-nephrotoxic |
| FLUVASTATIN | 94 | 5 | Corn oil | PO | Non-nephrotoxic |
| GADOPENTETATE DIMEGLUMINE | 125 | 5 | Saline | IV | Non-nephrotoxic |
| GEMFIBROZIL | 700 | 7 | Corn oil | PO | Non-nephrotoxic |
| GLICLAZIDE | 1500 | 5 | CMC | PO | Non-nephrotoxic |
| GLYCINE | 2000 | 5 | CMC | PO | Non-nephrotoxic |
| INDINAVIR | 1000 | 5 | CMC | PO | Non-nephrotoxic |
| KETOPROFEN | 20.4 | 5 | Corn oil | PO | Non-nephrotoxic |
| LEFLUNOMIDE | 60 | 5 | Corn oil | PO | Non-nephrotoxic |
| LINCOMYCIN | 1200 | 5 | CMC | PO | Non-nephrotoxic |
| LISINOPRIL | 2000 | 5 | CMC | PO | Non-nephrotoxic |
| LOVASTATIN | 1500 | 5 | Corn oil | PO | Non-nephrotoxic |
| N,N-DIMETHYLFORMAMIDE | 1400 | 5 | Saline | PO | Non-nephrotoxic |
| N-NITROSODIETHYLAMINE | 34 | 5 | Saline | PO | Non-nephrotoxic |
| RAMIPRIL | 1500 | 5 | CMC | PO | Non-nephrotoxic |
| RAPAMYCIN | 60 | 5 | CMC | PO | Non-nephrotoxic |
| RIFABUTIN | 1500 | 5 | CMC | PO | Non-nephrotoxic |
| RIFAPENTINE | 75 | 5 | Corn oil | PO | Non-nephrotoxic |
| SULFADIMETHOXINE | 1100 | 5 | CMC | PO | Non-nephrotoxic |

TABLE 2-continued 64 in vivo compound treatments used in the training set.

| Compound | Dose (mg/kg/d) | Time (d) | Vehicle | Route | Class |
|---|---|---|---|---|---|
| SULFAMETHOXAZOLE | 1000 | 5 | Water | PO | Non-nephrotoxic |
| SULFINPYRAZONE | 269 | 5 | CMC | PO | Non-nephrotoxic |
| TENIDAP | 75 | 5 | Corn oil | PO | Non-nephrotoxic |
| THIAMPHENICOL | 1500 | 5 | Water | PO | Non-nephrotoxic |
| TRANSPLATIN | 0.5 | 5 | Saline | IP | Non-nephrotoxic |
| VALACYCLOVIR | 88 | 5 | CMC | PO | Non-nephrotoxic |
| VALPROIC ACID | 850 | 5 | Water | PO | Non-nephrotoxic |
| ZILEUTON | 450 | 5 | Corn oil | PO | Non-nephrotoxic |
| ZOMEPIRAC | 11 | 5 | Saline | PO | Non-nephrotoxic |

In Vivo Studies

Male Sprague-Dawley (Crl:CD®(SD)(IGS)BR) rats (Charles River Laboratories, Portage, Mich.), weight matched, 7 to 8 weeks of age, were housed individually in hanging, stainless steel, wire-bottom cages in a temperature (66-77° F.), light (12-hour dark/light cycle) and humidity (30-70%) controlled room. Water and Certified Rodent Diet #5002 (PMI Feeds, Inc, City, ST) were available ad libitum throughout the 5 day acclimatization period and during the 28 day treatment period. Housing and treatment of the animals were in accordance with regulations outlined in the USDA Animal Welfare Act (9 CFR Parts 1, 2 and 3).

Clinical and Post-mortem Evaluation

All animals were monitored daily for clinical observations approximately 1 hr after dosing. For both the reference database studies (described in Example 1) and the sub-chronic study presented herein, gross necropsy observations and organ weights (liver, kidneys, heart, testes) were recorded for all animals following termination. Paired organs were weighed together. Body weights were recorded pre-test and daily thereafter for reference database (i.e., DrugMatrix™) studies, and on days 0, 3, 5, 7, 14 and 28 for the sub-chronic studies. Terminal body weights were measured at necropsy and used to calculate relative organ weights and percent body weight gain relative to day 0.

Clinical Pathology

Blood samples were collected at necropsy from the orbital sinus or abdominal aorta under $CO_2/O_2$ anesthesia prior to terminal necropsy by exsanguinations and pneumothorax. A panel of clinical chemistry and hematology parameters were analyzed on a Hitachi-911 and a Baker 9000 instrument, respectively.

Histopathology

The right kidney was preserved in 10% buffered formalin for tissue fixation and subsequently embedded in paraffin, sectioned and stained with hematoxylin and eosin. Sections (5 µm thick) were examined under light microscope by Board Certified Pathologists for histopathological lesions. The left kidney was snap frozen in liquid nitrogen for subsequent RNA extraction.

Statistical Analysis of Animal Data

Treatment group means for body and organ weights, and clinical chemistry and hematology measurements were compared to the time-matched vehicle control group by Student's T-test. Significance was declared at $p<0.05$.

Microarray Expression Profiling

Gene expression profiling, data processing and quality control were performed as previously described in Example 1. Briefly, kidney samples from 3 rats were chosen at random from each treatment and control group on day 5 for expression profile analysis on the Amersham CodeLink™ RU1 Bioarray (Amersham Biosciences, Piscataway, N.J.). Log transformed signal data for all probes were array-wise normalized used Array Qualifier (Novation Biosciences, Palo Alto, Calif.), a proprietary non-linear centralization normalization procedure adapted for the CodeLink RU1 microarray platform. Expression logratios of base 10 are computed as the difference between the logs of the averaged normalized experimental signals and the averaged normalized time-matched vehicle control signals for each gene.

Results

A few treated animals showed histopathological evidence of early chronic renal nephropathy on day 5, including minimal to mild regeneration of tubular epithelium, interstitial inflammation, pelvic dilation, focal thickening of basement membrane and focal infarcts. Cisplatin induced a high incidence of mild tubular basophilia (4 of 5 rats), while both cisplatin and carboplatin induced a high incidence of karyomegaly (3 and 5 rats, respectively). Mild tubular dilation and proteinaceous casts were also observed in one lead acetate-treated rat. Although considered early signs of tubular injury, these mild and infrequent observations are unlikely to bias the signature since the large majority of the animals treated with the 15 nephrotoxicants were unaffected on day 5. Furthermore, the incidence and severity of findings indicative of tubular injury were markedly increased after 4 weeks of treatment relative to the day 5 time point.

After 4 weeks of dosing, all 15 nephrotoxicants showed evidence of degenerative changes of the renal tubules or early signs of tubular toxicity. Histological findings included tubular necrosis, dilation, vacuolation, basophilia, mineralization and cysts. These lesions were also accompanied by a higher incidence and increased severity of epithelial regeneration and interstitial inflammation, as well as granular and proteinaceous casts. A high incidence of karyomegaly was also noted for cisplatin, carboplatin, lead and cobalt. Consist with the tubular injury was the concurrent observation of hypercholesterolemia and hypoalbuminemia for a number of the nephrotoxic treatments. Although weaker than most other nephrotoxicants, 4-nonylphenol and roxarsone induced clear evidence of tubular injury on day 28. For example, proteinaceous casts, tubular cysts and mineralization were only observed in one roxarsone or 4-nonylphenol treated rat on day 28, yet these treatments did induce a much higher incidence and severity of tubular regeneration (4-6 rats) and interstitial inflammation (6 rats) suggestive of future tubular injury. Since the nephrotoxicity of 4-nonylphenol and roxarsone have previously been described (see, Chapin et al., "The effects of 4-nonylphenol in rats: a multigeneration reproduction study," Toxicological Science 52(1): 80-91 (1999);

Latendresse et al., "Polycystic kidney disease induced in F(1) Sprague-Dawley rats fed para-nonylphenol in a soy-free, casein-containing diet," Toxicological Science 62(1): 140-7 (2001); Abdo et al., "Toxic responses in F344 rats and B6C3F1 mice given roxarsone in their diets for up to 13 weeks." Toxicology Letters 45(1): 55-66), and early signs of injury are apparent in the current study, these treatments were included in the positive class.

Example 3

Derivation of a Predictive Renal Tubule Injury Signature

Overview

The support vector machine algorithm was trained to classify experimentally confirmed nephrotoxicants from non-nephrotoxicants using the data acquired in Examples 1 and 2 above. A linear classifier (i.e., gene signature) was derived using kidney expression profiles from rats treated with 15 nephrotoxicants that induce renal tubular injury after 4 weeks of daily dosing, and 49 non-nephrotoxicants known not to induce renal tubular injury under subchronic dosing conditions.

Gene Signature Derivation

To derive the gene signature, a three-step process of data reduction, signature generation and cross-validation of the predictive signature was used. A total of 7478 gene probes from the total of 10,000 on the CodeLink™ RU1 microarray were pre-selected based on having less than 5% missing values (e.g., invalid measurement or below signal threshold) in either the positive or negative class of the training set. Pre-selection of these genes increases the quality of the starting dataset but is not necessary in order to generate valid signatures according to the methods disclosed herein. These pre-selected genes are listed in Table 3.

TABLE 3

7478 genes used to derive RTI signatures

| Accession # | Accession # | Accession # | Accession # | Accession # |
|---|---|---|---|---|
| NM_012939 | NM_012657 | NM_12848 | U67914 | AW915240 |
| BF415939 | J02635 | U66707 | NM_017354 | BF283413 |
| L18948 | AA997397 | AI236696 | D87351 | NM_019310 |
| NM_017250 | NM_012551 | BE109861 | AF285078 | AI233888 |
| AF150082 | M22899 | X05884 | BF405086 | NM_012879 |
| AI511090 | AF139809 | U94708 | U61729 | AI105410 |
| AA859352 | AI717121 | AF014503 | BE105137 | AA850034 |
| NM_017270 | D17310 | J02643 | NM_017259 | AA891826 |
| M63282 | NM_019308 | AF058786 | BE113157 | AI176677 |
| M35992 | X78997 | BE109018 | AI574903 | NM_012963 |
| AB009636 | AF055477 | NM_012803 | L17127 | BF420018 |
| X59132 | NM_013052 | AW916301 | AW914342 | BF283381 |
| NM_012824 | NM_019242 | BE113155 | AB012721 | U57097 |
| NM_012777 | U75924 | AF160798 | BF403552 | BF416240 |
| U24174 | M96674 | U27518 | U80076 | NM_012565 |
| NM_013105 | BE105381 | AF159103 | U59245 | AB005900 |
| AF057564 | NM_019322 | D00753 | AI598399 | AF111268 |
| BE109667 | AF034577 | AF290213 | M94454 | BE113285 |
| AF208288 | Z17239 | AI010583 | NM_021693 | BE113397 |
| NM_013068 | AI029460 | AJ237852 | AI176739 | BF388223 |
| NM_012682 | M11814 | AI410548 | U48596 | BE098827 |
| NM_019233 | NM_013175 | NM_013062 | AI412099 | M58587 |
| NM_013197 | NM_019150 | U56863 | U46118 | U10188 |
| AF151367 | AW913878 | BF282409 | AF027331 | AI144646 |
| BF555121 | AI171219 | U25137 | NM_012829 | M15327 |
| AI169311 | BF405468 | D38101 | X15741 | NM_017117 |
| NM_012738 | NM_019348 | AI407163 | U44091 | X94186 |
| NM_012786 | AW920818 | AW916143 | AB017820 | AF009329 |
| BF522317 | BF399598 | NM_012698 | AF121670 | BF284899 |
| AI180253 | NM_019128 | AI575641 | NM_013060 | BF285687 |
| J02657 | AI412261 | BF400833 | NM_013005 | AF214647 |
| NM_012764 | X06827 | J03863 | NM_012606 | AI172259 |
| AB040031 | AF199333 | Y13400 | NM_013094 | NM_020538 |
| AA818643 | M74716 | NM_012639 | AI233903 | AA892299 |
| D38381 | NM_017014 | AI236611 | BE115621 | AW921456 |
| X83231 | K03501 | AF120275 | L27843 | AW917933 |
| AB043981 | AA818120 | NM_019286 | L29259 | BF281701 |
| NM_017288 | NM_019332 | AI009597 | Y18567 | U75402 |
| U22520 | X63369 | AW915049 | BF287903 | AW915454 |
| BE113181 | AI412259 | NM_012567 | NM_021836 | BF567847 |
| AB013732 | AI011505 | AB000215 | AI111796 | BF395192 |
| D50671 | NM_012878 | AF254802 | AW917212 | AF105368 |
| AF202887 | NM_019298 | AW141051 | AI010950 | BF283340 |
| BE114586 | AB025431 | BF403190 | NM_012771 | AF247450 |
| AJ011607 | M62832 | NM_017123 | NM_017011 | NM_013008 |
| NM_019126 | AA849028 | AF227439 | X81395 | U39943 |
| D38494 | AA858817 | BE107840 | NM_012794 | AW528830 |
| M18847 | AI175530 | M26199 | NM_017289 | X56846 |
| U04317 | U16253 | AB036792 | AF144756 | BF551250 |
| AJ276893 | AW917537 | AW143005 | M34052 | NM_021680 |
| AI233740 | AB042598 | NM_012498 | AF086607 | X06889 |
| BE100918 | M81681 | BF283270 | AF112256 | L19031 |
| AF053312 | AI172112 | BF387347 | BE112719 | NM_013086 |
| AF044264 | AF306458 | AA891470 | NM_012735 | U08290 |
| NM_012633 | U24441 | NM_012881 | AI227829 | AJ242926 |
| AB032419 | U09838 | AA925167 | AA901342 | AI412418 |
| NM_012810 | AF060173 | NM_019295 | X76723 | AJ011035 |
| J03734 | NM_012603 | AI234119 | AF093567 | M33936 |
| X01976 | AW143537 | BE109691 | AI237640 | BE109016 |
| BF289266 | AI007992 | J02752 | L06821 | NM_020084 |
| D89731 | AI008376 | NM_012806 | X14788 | AI408348 |
| M91563 | AI012611 | BF405917 | AW918179 | M37828 |
| NM_012654 | NM_013217 | AI228222 | AI716265 | U15098 |
| NM_012870 | U49066 | AI010917 | BF551328 | AI144797 |
| AA819103 | AF015304 | NM_012533 | BF554744 | AI176553 |
| NM_012757 | AI101595 | BF401614 | D49977 | U65656 |
| AF063103 | AI137819 | D90109 | NM_019329 | NM_019339 |
| AF312687 | AW252871 | BF542912 | U31866 | BE108896 |
| BE111688 | NM_012580 | U45965 | AI412108 | AF249673 |
| NM_012720 | AI176730 | AI172281 | BF285185 | AI171162 |
| AI103158 | AI603128 | AW917780 | BF556736 | AW523849 |
| X68640 | U15425 | AW917985 | NM_012627 | BF400832 |
| AA998157 | Z17223 | M15882 | AF295535 | AA849743 |
| AW251703 | AA946230 | BF284124 | NM_012825 | AW143179 |
| NM_012584 | BF286009 | AW915415 | AI169596 | NM_012842 |
| BE099881 | U55995 | AW523614 | AJ131563 | U07971 |
| AA848355 | X87107 | AI407487 | M16235 | AW251791 |
| AF158186 | AF068268 | M84416 | NM_017237 | NM_019204 |
| Y00065 | U20796 | AI180421 | AW915996 | U12309 |
| AF133037 | U41663 | AW142880 | BF283556 | BE095878 |
| AW920606 | AW434178 | BE113060 | BF413176 | BF282961 |
| NM_017195 | AB022883 | AI101117 | U41453 | NM_021691 |
| AI171656 | NM_017019 | BF282796 | BF402407 | NM_012708 |
| AI598316 | NM_017208 | BF413152 | AF086630 | BF405035 |
| AF109643 | BF393825 | X89603 | AI407719 | AA955213 |
| AI411981 | AA800341 | X68878 | NM_012938 | M10161 |
| NM_019230 | AA946485 | AI412460 | BF398155 | NM_017275 |
| NM_017331 | AI144771 | NM_012833 | AA817877 | U07560 |
| AI071251 | AI555029 | AA945100 | AI172302 | BE109271 |
| AW143506 | AI407201 | BF281697 | BF562755 | NM_021746 |
| AI408713 | AI411941 | AA850910 | AF029107 | M19651 |
| U26686 | AF154114 | U21871 | AW862653 | AF007212 |
| AW915739 | NM_021869 | NM_012564 | NM_012779 | AF015953 |
| NM_017097 | AA892549 | AF089825 | J02627 | AW915613 |
| AW144649 | NM_012618 | AI171800 | X97477 | BE119628 |
| J03886 | AW917460 | BF396132 | AF038591 | BF285565 |
| AF184983 | U67082 | AI176814 | M94064 | NM_012908 |
| BF414043 | X84039 | NM_013064 | AI535126 | AI170799 |
| D83231 | NM_012597 | AW527509 | AI059223 | AW144399 |
| AI227912 | AA819832 | AW914004 | AI234024 | U12623 |
| AI408286 | AI111954 | NM_017115 | AI599016 | AF009133 |
| AA964744 | AI716469 | AW523875 | NM_017113 | AI103572 |
| BF288765 | BE105618 | AW919125 | AW917133 | Z78279 |
| AA817759 | L19656 | M35297 | AA851926 | BF391604 |
| BF557871 | U97146 | U44845 | AW919210 | D16237 |

TABLE 3-continued

7478 genes used to derive RTI signatures

| Accession # | Accession # | Accession # | Accession # | Accession # |
|---|---|---|---|---|
| AW920017 | AA893596 | X83399 | AI556458 | AA892049 |
| NM_013029 | AJ001713 | NM_021763 | AA925375 | BE109730 |
| AF107723 | AI180010 | AI008409 | BE106971 | BE117330 |
| AW142962 | NM_017215 | D50664 | AF179679 | NM_012621 |
| BF525022 | AI178784 | NM_017122 | BE109520 | AW520812 |
| AI409934 | BE112216 | AI172222 | BF396293 | AA800587 |
| NM_019344 | D13555 | BF389915 | Y17606 | AF193014 |
| L05435 | NM_020087 | AI549393 | U35371 | BF282980 |
| NM_017279 | AA800292 | Z30584 | U32679 | AA858900 |
| NM_012614 | BF399627 | AF102854 | AW526005 | AW915775 |
| AF277452 | AW142290 | AI177015 | D88586 | AI104278 |
| AI102884 | BF283610 | AW862656 | NM_012964 | BE111666 |
| AW919995 | X91234 | BF523561 | BF407456 | X03369 |
| L46791 | AI137339 | L15453 | NM_017027 | AA946394 |
| AF104362 | BE108873 | AA850740 | AA850541 | L19341 |
| BF415024 | BE113252 | AI179990 | BF564217 | NM_021747 |
| J03583 | AI716560 | AW918006 | AA858862 | AW917544 |
| M26744 | NM_013139 | AF172446 | AW142828 | U05675 |
| NM_013126 | AW915606 | AI102047 | NM_017335 | AI102771 |
| J03093 | AW918169 | AW918050 | NM_013106 | BF409724 |
| NM_012588 | AJ302650 | L14323 | U30290 | X13016 |
| Y00090 | U66470 | NM_017180 | AI010251 | BF403184 |
| AI228970 | J03026 | AW918529 | AI012235 | AB000489 |
| NM_019326 | AI136740 | AW921215 | AW143771 | AF136584 |
| AI454612 | NM_017167 | BF285985 | BF549490 | AI407141 |
| BE107069 | AI716512 | AF148324 | AF009330 | AW434228 |
| AF157016 | NM_013413 | BF282282 | AW525762 | BE106791 |
| AI411412 | BE107234 | AI576621 | AW919683 | BF396602 |
| AI556066 | BF550033 | X53427 | BE117335 | BE524971 |
| AW916833 | BF563113 | AW144705 | U22893 | AI170400 |
| X14159 | NM_012851 | AJ132008 | BE120016 | AI411304 |
| AF198442 | AA894092 | AJ133104 | AA892250 | BE103975 |
| AW913932 | BF283631 | AW143091 | AF055286 | NM_021595 |
| BE111710 | M63122 | BF556210 | AW529723 | BF558694 |
| NM_017074 | AA894210 | BF562701 | AW913917 | D87336 |
| U33500 | AI411995 | U81186 | NM_013089 | M15797 |
| AI045288 | AW913986 | AI232183 | U66471 | AW918776 |
| AI101323 | AW919092 | BF411166 | AA955786 | AI409218 |
| AI548591 | BF284803 | M27223 | AI012434 | AA891839 |
| AA817798 | AA965057 | AW917546 | AI575699 | AF237778 |
| AI230339 | AF016297 | NM_012835 | NM_021587 | AI178875 |
| BE108282 | BF284475 | BF394332 | AF118651 | AW523888 |
| AA848499 | NM_013057 | NM_013176 | AI385364 | U61373 |
| AA892366 | AW915287 | X77797 | AI579216 | AB043892 |
| AI406538 | BE113142 | AA893184 | NM_017271 | AF045564 |
| U17967 | AI168968 | AF155196 | BE100748 | AI011757 |
| AI408557 | AA875301 | AF171936 | BE106832 | NM_017090 |
| AI235942 | AA964535 | NM_012998 | U62667 | NM_017359 |
| BE109661 | AW921399 | U40064 | AF082535 | X85183 |
| NM_012750 | X91892 | AI764464 | BE121120 | AF013241 |
| AW251848 | AW914178 | BF285034 | U23407 | AI007919 |
| NM_012676 | AA850480 | NM_012561 | AI409065 | AI111579 |
| X65747 | AI175457 | AI012250 | M77479 | AW531805 |
| AI406941 | AI410352 | AI408580 | X04644 | AW921168 |
| AI236771 | BE120339 | AW144039 | BE116867 | D85035 |
| AF077354 | BF286916 | AA800782 | AW917160 | AW918417 |
| NM_017261 | BF566488 | AB020520 | BF566679 | BE109531 |
| AF155910 | AF036959 | AI102591 | AF010293 | BF551331 |
| J03627 | AF041374 | D14015 | D12769 | NM_017330 |
| L36459 | AI137683 | NM_012489 | M69138 | BE095859 |
| AB009686 | AI412889 | NM_012493 | NM_017327 | BE113367 |
| BE113132 | AJ131848 | AW915453 | AA818759 | AB118340 |
| NM_012940 | AJ224120 | AA944169 | AJ222971 | M90661 |
| NM_019358 | NM_012687 | AF013144 | AW252812 | AB033771 |
| AI008390 | U09228 | AF169636 | BE116233 | AF111181 |
| BE120346 | AF001417 | AI071412 | BF406291 | AI237075 |
| X12355 | AF286595 | AI411400 | D10699 | AI454923 |
| AW919284 | AA800719 | BF389519 | BF284190 | AI502229 |
| D85760 | AI172189 | BF411148 | BF409783 | AB003587 |
| NM_012668 | BF555498 | M13646 | Z14030 | AA800260 |
| AI044740 | NM_017089 | AB012139 | AI237403 | AB011528 |
| AW528864 | NM_019239 | AW251324 | NM_019192 | AW914789 |
| AA799428 | AW524733 | AB000776 | X04310 | J00705 |
| Y18965 | AI409871 | M80550 | AF014827 | U44750 |
| M17412 | BF288073 | NM_012625 | AA943824 | AI179459 |
| AF248548 | NM_017310 | BF557923 | AF186469 | BF412037 |
| AI235546 | U39546 | AA851370 | AW144673 | D13963 |
| L25527 | U61266 | AW916826 | BF290076 | M60388 |
| NM_019904 | AI171646 | NM_013226 | NM_021868 | NM_013134 |
| AI101924 | NM_013043 | AI176515 | U74586 | X05883 |
| BF549650 | AB023432 | BF417292 | L35921 | AA891690 |
| AB039663 | AW524724 | D86383 | AF133731 | AF251305 |
| AI234852 | BF412073 | AI176773 | AA997881 | AF163569 |
| AW921038 | BF405050 | AW914097 | AW916609 | AI599801 |
| NM_012701 | AA859796 | AA799676 | BF282415 | BF413513 |
| Z34264 | BE349698 | AF087697 | D13121 | M55636 |
| AW918222 | BF284692 | BE116886 | U44129 | NM_012667 |
| AW919395 | X99723 | AB027143 | AF021343 | NM_019240 |
| AB027155 | AI230728 | AI007666 | BE097240 | AW916836 |
| AI406747 | AI236770 | AI406697 | AI179988 | AI103918 |
| AW915643 | AI406948 | NM_012522 | D90404 | AW531368 |
| AW917481 | BF404362 | M83209 | NM_017047 | BE113242 |
| BE349770 | M95058 | AI176842 | U47280 | BF285921 |
| BF550231 | AA818471 | L04527 | AI412625 | NM_017340 |
| U63740 | AI176476 | NM_019168 | AI411021 | X70871 |
| X55995 | AI406342 | X53724 | BF416285 | AI101396 |
| AF327513 | AF247451 | AW525211 | AI172196 | AI113104 |
| AI177140 | BF553139 | AA866351 | BE116946 | BF281931 |
| AB001075 | NM_016998 | AF041838 | BF398367 | U14907 |
| BF556958 | AW920082 | AF297118 | NM_012999 | AW253265 |
| U93880 | AW535233 | AI406968 | BE108670 | M31363 |
| AI171653 | BE099774 | BF404452 | BF287788 | U30789 |
| BF399489 | L05175 | NM_017185 | BF404478 | AF038388 |
| AW918022 | NM_017029 | AF182714 | AW141130 | AW526289 |
| BF398845 | AF214733 | BF393972 | NM_019306 | BE101472 |
| M55601 | X89968 | BF398716 | AI009609 | BF285109 |
| NM_012505 | AW918674 | NM_012530 | AW523642 | BF400636 |
| NM_013200 | NM_013036 | U68725 | AW901337 | BE117156 |
| AA799503 | NM_019375 | X78606 | AI145991 | BE120810 |
| AF072935 | AW144670 | D88666 | BE113179 | NM_013074 |
| BF398063 | BF282712 | BE107169 | BF398114 | AI072384 |
| AI235674 | BE107427 | AW916745 | M38060 | D16817 |
| L13600 | NM_012942 | D13927 | U89608 | NM_012679 |
| AA892778 | NM_019258 | NM_017135 | AA848820 | NM_017193 |
| AW535307 | BF283056 | AA945724 | AF080106 | AF199504 |
| NM_019289 | NM_017211 | AW143008 | AW434109 | AI102073 |
| AI176591 | X70223 | BE105967 | BE119862 | AI105049 |
| M26125 | AA850347 | BF551345 | NM_016987 | AW253907 |
| X73371 | AI176836 | BF554752 | NM_017292 | BF400042 |
| NM_017222 | AW142823 | U06755 | AW918564 | BF542426 |
| NM_021664 | NM_012845 | U10303 | NM_012959 | U56936 |
| U26033 | Y09945 | AI410546 | AI179101 | AA900654 |
| AB007689 | AW918231 | L11002 | AW920764 | AI009727 |
| AF021854 | NM_019309 | AI169317 | U64451 | AA900261 |
| AI101181 | AB011365 | AW915558 | AJ293617 | X66539 |
| AI102732 | AF021348 | X03015 | L19927 | C06844 |
| BF395781 | AF192366 | AA891535 | X99470 | AI070270 |
| BF563517 | AW527151 | AA892500 | AA819481 | AW520754 |
| AA818353 | BE098709 | AW524433 | AI172146 | AW918029 |
| AI176497 | BF557244 | AW916447 | AW915254 | NM_019369 |
| AI227885 | BF567710 | BE107464 | AW920478 | X95507 |
| AW254369 | NM_012501 | BE108230 | BF550822 | AF022085 |
| D25233 | U89514 | NM_012838 | U39571 | BF284809 |
| L14617 | U91539 | NM_019370 | U75920 | M34643 |
| NM_012532 | AA892798 | AI169655 | AA893172 | X76168 |
| NM_019283 | AI234149 | BE106663 | AF314540 | AI170766 |
| AB024398 | AI171288 | BE109059 | NM_019243 | BF282972 |
| AF151373 | AI716500 | NM_012715 | BF548454 | BF389876 |
| AI717736 | AW528865 | U73525 | J05266 | BF406752 |
| BE113224 | BF288208 | AA850319 | AA800222 | NM_012549 |
| BF420610 | NM_012884 | AA892852 | AB011533 | NM_016995 |
| AF230645 | AI232272 | AI229630 | AI103924 | U95368 |
| AI178171 | AW144339 | AI716086 | AW529808 | X60370 |
| AI716250 | AW533508 | BE106513 | AW916093 | X74815 |
| AW434520 | AW917427 | BF401626 | BF282239 | AA800184 |
| NM_019186 | AY004290 | BF404514 | BF420074 | AF306457 |
| U23377 | BE101480 | BF415760 | L29232 | AW144456 |
| AA848451 | BE107465 | BF420628 | NM_017144 | BE101108 |
| AF067727 | BF549703 | BF556874 | NM_019214 | BF411134 |
| AA998660 | AF189019 | NM_019143 | NM_020096 | Z11690 |

TABLE 3-continued 7478 genes used to derive RTI signatures

| Accession # | Accession # | Accession # | Accession # | Accession # |
|---|---|---|---|---|
| BE113620 | BE108837 | AW141939 | X58465 | AF025670 |
| AA818392 | AI010272 | AW434239 | U42627 | AW921149 |
| AI071243 | L22079 | AI030179 | AA925353 | AA944556 |
| AI177050 | AA894335 | BE110739 | AF059258 | AI010281 |
| AW435011 | AF036548 | NM_012553 | NM_021682 | AI011455 |
| AW918443 | AF157498 | NM_012689 | AA799526 | BF282149 |
| BE106598 | AI105080 | AA818796 | AW251115 | BF403319 |
| BF411113 | AF320509 | AI237118 | AW915925 | BF416794 |
| AA965219 | AI012574 | AI639168 | AI177397 | D10926 |
| AI555002 | AW532606 | BF282476 | BE120725 | AI104478 |
| BE098212 | AW915048 | BF283760 | BF564940 | AW144344 |
| AF076183 | BE108327 | BF398053 | AB002801 | AW534329 |
| BF558592 | BF282370 | BF410020 | AI009657 | U59486 |
| U17565 | NM_017065 | NM_020097 | M65148 | AA799993 |
| BF415786 | NM_017276 | AW917098 | NM_019216 | AI406660 |
| NM_017147 | AI169829 | AA021585 | AA892770 | AI704771 |
| U24175 | AW253947 | AA957047 | AI556534 | AW144347 |
| NM_019291 | BF409296 | AF188608 | AW914277 | AW913888 |
| AF182949 | AI227945 | AI169105 | BF284137 | J05499 |
| AW141292 | NM_012678 | AW918717 | BF563117 | AB035201 |
| BF394166 | NM_021688 | NM_012920 | AA848821 | AI168941 |
| BF410183 | U42975 | AF063102 | AA943576 | AI411510 |
| AB016425 | AF011789 | AF149118 | AI409040 | AA899704 |
| BF525016 | AI170249 | AI011501 | AI598976 | AA945761 |
| D88250 | AW529672 | AI235960 | U60282 | AI406809 |
| U52102 | BF283390 | AW916210 | AA945869 | AA874859 |
| AI412423 | BF561659 | AW917663 | AW918611 | AI102026 |
| BE095842 | AB035306 | BE115280 | AF190458 | AI176993 |
| AW914408 | AW921109 | BF413244 | NM_019153 | L78306 |
| BE103689 | NM_012880 | U15408 | AA946474 | U10357 |
| AA819268 | NM_021846 | AA955579 | AF007818 | AA799664 |
| AW913998 | BE104266 | NM_021775 | AW143818 | NM_019333 |
| X69716 | BE116564 | S57864 | U85512 | U69279 |
| AF118816 | BF562675 | AA955206 | X07365 | X60789 |
| AI234012 | NM_013003 | AW532179 | AW525184 | BF284889 |
| BE108973 | AI599126 | NM_019620 | D12516 | BF398564 |
| BF550769 | U98973 | AI172057 | AA800029 | NM_013012 |
| NM_019262 | BE109665 | AW252815 | AI179538 | NM_017034 |
| NM_019282 | BF556327 | BF285046 | AI227894 | X82152 |
| U92010 | D83036 | AA848826 | BE116816 | AI232098 |
| AF003835 | AI178527 | AI175098 | NM_012739 | X59037 |
| AI111802 | AA943995 | U58466 | X59037 | AF097887 |
| AI230699 | AI406464 | AB036421 | AF043642 | AI235923 |
| D12678 | AI412304 | AI104545 | AI231761 | BF405417 |
| AA848311 | AI599520 | BF404935 | BF559190 | D13962 |
| AF286534 | BF397840 | AB017260 | AF259981 | L13445 |
| AF011790 | AA801208 | AB021980 | BF396614 | NM_019205 |
| AI234142 | AA849975 | AI012231 | D88035 | AF046886 |
| AI236084 | AI045904 | BE120595 | NM_012972 | AI598942 |
| NM_013004 | AI411580 | AW533822 | AA799476 | BE102426 |
| AW917823 | M55049 | BE106398 | AA891746 | BE328941 |
| BF406312 | X78461 | AA817812 | AI170114 | BF563262 |
| NM_012661 | BF403410 | BE106693 | AI407982 | NM_019203 |
| NM_012967 | NM_012563 | L09656 | AW914850 | X68199 |
| AA866419 | AI413060 | BE108277 | BF550847 | AF021935 |
| BE119802 | BF408325 | AA944061 | X66366 | BF403098 |
| AI104484 | X06338 | AA945771 | AI710683 | AI011610 |
| AI144644 | AA892325 | AB024930 | AW916287 | NM_012841 |
| AI411971 | AF207605 | AI010965 | NM_012558 | NM_020072 |
| AW435041 | AF263368 | AW143130 | AI235047 | AF095576 |
| BF556879 | AW916182 | AW523899 | BF396316 | AW918640 |
| NM_012693 | BF419280 | BE111805 | BF418597 | BF419482 |
| AB017696 | BF556833 | BF282313 | AA963234 | U96921 |
| BF282034 | NM_019293 | M17086 | AF071003 | AA818184 |
| D85100 | BE101619 | AI010948 | AF182717 | AI168986 |
| AF100960 | AW144663 | AW251681 | AI574743 | AW915209 |
| AJ011811 | BF412296 | D70816 | AI599339 | BF286131 |
| BF418869 | BF416115 | NM_017038 | AW914966 | NM_019199 |
| NM_017235 | X69834 | AA944518 | AW915217 | U16655 |
| AA946430 | AI235784 | AI411149 | AW917653 | AW919239 |
| AI104125 | AW534151 | BF558676 | BE113656 | BE109746 |
| AI144863 | AW919320 | Y14933 | BF284918 | BF558086 |
| AI409756 | BE104321 | AA850509 | NM_012499 | L23204 |
| AW140637 | AB002111 | AI232565 | NM_013145 | BE098326 |
| AW918085 | Y18208 | AI407560 | BE107259 | BF398684 |

TABLE 3-continued 7478 genes used to derive RTI signatures

| Accession # | Accession # | Accession # | Accession # | Accession # |
|---|---|---|---|---|
| BF283003 | BF420720 | AI501497 | BF283261 | AI072493 |
| BF408444 | NM_017204 | AW251416 | BF400209 | AF099093 |
| BF418630 | AA850896 | AW914809 | BF404557 | AI412054 |
| NM_017337 | AI171098 | BF287191 | M95768 | BF282646 |
| NM_021842 | AI179021 | BF414010 | X06564 | BF396955 |
| BE110514 | AW917461 | BF566546 | BE097587 | BF419234 |
| AF184921 | NM_012923 | L22191 | BG153269 | BF556836 |
| AI176970 | AI412936 | L36884 | AA891742 | AI045635 |
| BE115041 | BE098743 | L43592 | AF030423 | AW144346 |
| AA817769 | U94709 | NM_017143 | AF181259 | AW917390 |
| AA955926 | AF223677 | U06436 | AI410906 | AW920271 |
| AB012933 | AW529756 | AA850333 | AJ242649 | BF281754 |
| AI172465 | M35106 | AI169058 | AW441131 | J03190 |
| NM_012666 | NM_012869 | AI237622 | D12498 | AB020757 |
| NM_013167 | AW143834 | NM_017322 | J05132 | AI009371 |
| AB011529 | AW535377 | NM_017332 | U48249 | AI231799 |
| AW531919 | BE109179 | U69702 | AW918418 | BF396682 |
| AI228528 | M37394 | U77697 | BF281400 | BF417187 |
| AI171994 | U13396 | AF004218 | D16308 | M63574 |
| AI231808 | U17901 | AF058787 | AW917550 | AA799741 |
| AI412662 | AI409316 | D31873 | BF400606 | AA799751 |
| AW524460 | AW917557 | AF043345 | BF547620 | AF106860 |
| AW917674 | BE113545 | U05014 | BF563077 | BF281149 |
| BF287209 | BF405134 | AA891447 | M61726 | AB019791 |
| NM_019257 | AA819488 | AI412169 | NM_017212 | AW142328 |
| AB033830 | D88450 | U55816 | AA800476 | BF396180 |
| AI409182 | AA866477 | X55969 | AI231210 | BF399385 |
| BF289240 | AI102735 | AA848951 | AI235446 | D00403 |
| BF396295 | AI227769 | AI071288 | AW531735 | NM_017040 |
| BF412673 | BE106459 | AW530415 | BE111795 | AA850725 |
| NM_017217 | BE113152 | AW915057 | BE349699 | AB041998 |
| NM_021856 | BF283382 | BE107033 | BF284919 | AW144170 |
| AF111160 | D25224 | BF283353 | BF396319 | AW920501 |
| AI104292 | AA850987 | BF404908 | AF087696 | BE108882 |
| AI603127 | BF400611 | BF407675 | AI009647 | BF389244 |
| X07320 | D28754 | L07315 | X74832 | BF408285 |
| BE113369 | M80601 | NM_017131 | AF002281 | NM_019386 |
| BE120386 | NM_012524 | AI406369 | AI013919 | Y17048 |
| BF399607 | X17037 | AF106659 | AJ295748 | AA944314 |
| BF409977 | AW526352 | AF277900 | AW144385 | AI172618 |
| NM_017325 | AI044316 | AI172003 | AW252087 | AI180353 |
| U60096 | AW915106 | AI411352 | AW920527 | AI235467 |
| AF273025 | AW914808 | AW921986 | BE111888 | AI407999 |
| AI411225 | BF283797 | BE107674 | AA875143 | AI547463 |
| BE107250 | BF403853 | BF285066 | AF202265 | NM_013137 |
| AW915650 | BF555793 | D49955 | AI231444 | U37058 |
| BF285467 | NM_012816 | NM_012497 | BF555116 | AF157026 |
| BF398403 | U60835 | AI233257 | D87839 | AI009074 |
| M29853 | AI169629 | NM_017075 | AW142811 | AW526039 |
| NM_012725 | AW140903 | NM_021740 | AW915601 | BE109164 |
| X51991 | AW916321 | BF413765 | BF288273 | NM_012514 |
| X57970 | D50568 | BF550866 | NM_012721 | AI175871 |
| X92069 | NM_012903 | BF555899 | AA892791 | AI411930 |
| AA892522 | AI228236 | M21208 | AA899304 | AI602125 |
| AF160978 | AW143256 | AF036537 | AI176505 | BF522885 |
| AI711516 | BE107147 | AI600221 | AI410099 | BF288063 |
| BE119676 | AF030091 | AW915518 | AI709768 | BF565795 |
| AA996836 | BF287099 | AW917510 | BE111762 | NM_012862 |
| NM_017124 | BF550883 | BE097210 | BF282458 | AA800455 |
| AB052170 | BF551283 | BF388763 | BF524872 | AF228917 |
| AI598407 | D49836 | BF550217 | NM_013001 | AI171736 |
| AJ132846 | M18467 | M55045 | U61157 | AW915404 |
| AW141993 | NM_013091 | NM_012704 | AF030253 | AW917389 |
| L19118 | AA891734 | U73458 | M83676 | BE114160 |
| NM_013148 | AI145328 | BF557672 | AF163477 | BF283798 |
| NM_019155 | AI171655 | X57228 | AI175555 | BF567631 |
| AI105101 | AW917475 | BF291167 | BF416236 | L02530 |
| AI599133 | U50185 | AI599349 | U20195 | AF080468 |
| BE107503 | NM_017068 | AW520770 | U31668 | AI176944 |
| BF419138 | NM_017260 | BF555127 | AA850037 | AI179372 |
| AJ003065 | BF290834 | AI412627 | U67884 | AW918208 |
| AW143887 | BF412769 | AI555466 | AW914944 | BE109208 |
| AW916474 | BF555129 | AJ011608 | AW916786 | BE113233 |
| AW917766 | BF557296 | NM_017181 | NM_012828 | BE118580 |
| NM_013071 | D13126 | AB004329 | AA900400 | BF396948 |

TABLE 3-continued

7478 genes used to derive RTI signatures

| Accession # | Accession # | Accession # | Accession # | Accession # |
|---|---|---|---|---|
| NM_017345 | M17527 | AF205438 | AF306394 | BF549525 |
| X71068 | U17604 | AI407017 | AW533663 | NM_019363 |
| AI411997 | AA819306 | AW143149 | AW915554 | AF239674 |
| AA800507 | AF005099 | AW918238 | AW917516 | AW915161 |
| AA875261 | AW918548 | BF386716 | BE110577 | BE105872 |
| AI231776 | X74549 | U53855 | BF281848 | NM_012819 |
| AI599077 | AA850490 | X57523 | D86711 | NM_019237 |
| AW526320 | AW251878 | AF044201 | J03819 | AI406821 |
| BE116976 | AW531902 | AW914119 | NM_017077 | AF084576 |
| BE117878 | BF392577 | AI102739 | AW142947 | AI060205 |
| U18771 | AI044865 | AW920722 | AW434045 | AI179609 |
| AF065161 | AI059079 | NM_013070 | AI232337 | AI408442 |
| AF150091 | AI454134 | AA800062 | AJ277747 | AW915550 |
| AI231716 | AI454913 | AA818952 | AW918255 | BE113312 |
| BE113635 | AW919929 | AI012608 | AW919873 | BF387255 |
| BF546202 | D16479 | AI137286 | BF286478 | BF394261 |
| U04738 | NM_012545 | AI234678 | BF388422 | AA964824 |
| AI012120 | NM_012555 | AI406707 | NM_012562 | AF184883 |
| AI178229 | Y00480 | AI411501 | NM_019211 | AI231792 |
| AW253043 | AF068202 | AW915713 | U42209 | AW521352 |
| AA818438 | AI406502 | BE105713 | AI412190 | AW917064 |
| AI103634 | AW253742 | BE107247 | AI716642 | AW918585 |
| AW918605 | AW919881 | U19967 | BF555161 | BE101088 |
| BE115947 | U62326 | U35775 | NM_012527 | U72353 |
| BE116569 | X57764 | AF037071 | NM_021584 | NM_020106 |
| BE118450 | BE112952 | AI009599 | AB021645 | X71071 |
| BF389910 | NM_013153 | AI172198 | AI169116 | AA955396 |
| BF397834 | AA874924 | AI227748 | AW919190 | AI176056 |
| NM_012503 | AA943817 | AW143395 | BE098463 | AW916119 |
| NM_012936 | AI175978 | BE113449 | NM_012590 | AA998964 |
| NM_019305 | AI177748 | BF396079 | NM_019364 | AB012759 |
| X97376 | AI178923 | M17069 | U11038 | AI179901 |
| BE106816 | NM_012974 | U01914 | AA850505 | AI407827 |
| BE118122 | NM_013215 | X52498 | AA892818 | AI716077 |
| BF403852 | U09583 | AF315378 | AI177408 | BE098955 |
| D63648 | AI233769 | BF284065 | AI227612 | BF388440 |
| NM_021859 | AI385171 | AI007922 | AI412150 | NM_277903 |
| AA944006 | AI409259 | AI013500 | AW523647 | AI058960 |
| AB017702 | BE108949 | AI170394 | AW917504 | AI409077 |
| BE100018 | BE103916 | AI556941 | BE095865 | AW141921 |
| BF415061 | AI227890 | AW141985 | BE103444 | BF285451 |
| NM_021703 | AW142560 | BF409042 | M18028 | BF389856 |
| AA944542 | BF420172 | U06864 | NM_012733 | BF393807 |
| AF001896 | BF557300 | U08136 | X83579 | D16348 |
| AI010954 | BF559836 | U50707 | AA997412 | NM_017316 |
| AI012498 | BF567496 | AF245172 | AF151982 | U10279 |
| AI176695 | D25290 | AF272892 | AI137817 | AF290194 |
| AI180420 | M88709 | AI103040 | AI411605 | AI170797 |
| AI406310 | U32314 | AI227907 | AW143854 | AI179993 |
| AW531361 | X16359 | AI412317 | AW507078 | AI713159 |
| AW916592 | AA801139 | BF404556 | AW525122 | AW917818 |
| BE112933 | AI407016 | NM_013049 | AW916054 | J00741 |
| AW251204 | AW915084 | BF288129 | AW528898 | AF020618 |
| BE095833 | AW916127 | BF403009 | AW915175 | AF059311 |
| BE110525 | BF404842 | BF555971 | BF287814 | AF090867 |
| BF400666 | BF418582 | NM_019273 | U61261 | AI172386 |
| NM_012763 | L37380 | X02904 | AB009463 | BF284171 |
| U67080 | AA943742 | AA800273 | AB032164 | NM_017220 |
| AF059530 | AI168952 | AI102064 | AF031483 | AA925490 |
| AI009650 | AI556408 | AI171802 | D29969 | AW142307 |
| AI555351 | D50559 | AI230430 | M34083 | AW435429 |
| AI711114 | AW945320 | AW917132 | AA848470 | AB012233 |
| AW918076 | AF247452 | BE108178 | AF058791 | AI175440 |
| BF284878 | AI070113 | BE108857 | AI176665 | AI409380 |
| BF399083 | AW915174 | BF397872 | AI178491 | AW520758 |
| BF419406 | BE111769 | BF543356 | AI232898 | AW524559 |
| NM_013115 | BE116370 | BF543478 | AI233288 | AW534383 |
| NM_021744 | BF407344 | NM_012655 | AW532652 | AW915350 |
| AB043870 | BF554877 | NM_019279 | AW915437 | BE113217 |
| AI598442 | BF556614 | U16858 | U06099 | BE116973 |
| AW253880 | U29174 | AA851728 | U83112 | BF282030 |
| AW917588 | X85184 | AI137188 | AA965063 | BF284994 |
| BE112998 | BF566580 | AI177431 | AB009999 | AI009603 |
| U41853 | AI176632 | AI555341 | AF023657 | AI011034 |
| AA817841 | AI178935 | AI600037 | AF135059 | AI011713 |

| Accession # | Accession # | Accession # | Accession # | Accession # |
|---|---|---|---|---|
| AA849966 | AI406531 | AW526346 | AW144034 | AI171480 |
| AF220760 | AW144006 | BE108174 | AW251238 | AI232365 |
| AI102512 | NM_017141 | BE111925 | AW254429 | AI408347 |
| AI231088 | X04240 | BF282876 | AW915944 | AI716103 |
| AI598315 | AB023634 | BF557821 | BF401313 | BE111634 |
| AI713206 | AI175008 | D31838 | J05122 | BE112615 |
| AW144044 | AI237657 | L27081 | NM_019135 | BF393611 |
| BE117902 | AI717113 | NM_019167 | U12187 | BF408081 |
| BF282238 | AW252879 | AA849738 | X03475 | NM_012601 |
| BF410755 | AW532489 | AI235219 | AA849719 | NM_017342 |
| M22323 | AW916092 | BE107395 | AF268030 | NM_021764 |
| M81784 | BF564219 | BE108776 | AI009594 | U75689 |
| Z48444 | NM_013065 | BF282217 | AW143233 | X60822 |
| AA799832 | U49057 | BF550270 | AW143233 | AF063939 |
| AF096835 | AA800483 | AA859010 | AW144502 | AI179974 |
| AI008701 | AB042407 | AI600035 | AW251339 | BF398016 |
| AI176212 | AI170313 | AI716255 | AW435110 | BF525193 |
| AI176625 | AW252251 | BE102621 | AW916721 | D10665 |
| AI180275 | AW917256 | BF284716 | BF544951 | AB014089 |
| AI412673 | AW919062 | BF397805 | NM_017005 | AI175820 |
| BE113146 | BF389884 | BF400811 | U77933 | AI237593 |
| BF403136 | BF396282 | L18889 | AA998160 | AI409747 |
| NM_021589 | NM_012671 | NM_013132 | AI176825 | AW253010 |
| AI059349 | AA800010 | U68168 | AI229849 | BF283898 |
| AA942765 | AA891944 | AF053317 | AW918000 | BF284303 |
| AI137297 | AF000577 | AI169878 | BE120513 | BF555924 |
| AI169001 | AF017393 | AI178796 | BF419158 | NM_012795 |
| AW252664 | AF065147 | BE107485 | NM_017269 | NM_013135 |
| BF397998 | AI100769 | AA943552 | NM_017365 | U40603 |
| AF021923 | AI170067 | AA943564 | NM_019219 | U43175 |
| AI230762 | AI170405 | AF017437 | NM_021771 | AJ000696 |
| AW141128 | AI236618 | AI172175 | U30381 | BF548957 |
| AW534159 | AW918017 | AW142913 | AA892370 | BF549697 |
| AW915055 | BE096387 | AW143093 | AB022014 | L38615 |
| AF226993 | BF413396 | AI408960 | BF392344 | BE126739 |
| BE112913 | D00252 | AW142588 | BF404539 | BF288138 |
| D88364 | AA799400 | BE113966 | AF000423 | BF396678 |
| NM_013114 | AA848776 | BE117883 | AI010267 | BF558506 |
| NM_019255 | AI176611 | AF075382 | AI101199 | BE111625 |
| U38253 | BE116768 | AF087454 | AI231787 | BF558467 |
| U49055 | M77736 | AI715048 | AI715452 | NM_017152 |
| AA998662 | AA850728 | AI407222 | AJ002940 | BF419635 |
| AI104846 | AI178761 | AI599104 | AW525049 | D21799 |
| BF406522 | AW916628 | AW141280 | AW919666 | AI069912 |
| BF413631 | BE098366 | BF419602 | BE107334 | AW914758 |
| D38072 | BF281544 | L02896 | NM_012636 | AW914939 |
| U75916 | BF523059 | NM_017262 | NM_019284 | BF284700 |
| AI227843 | D16302 | AI406693 | AA997435 | BF404603 |
| AI411425 | NM_021660 | NM_021762 | AI236090 | BF555890 |
| AW531148 | AI230918 | AA955175 | AI575940 | M64301 |
| BE115635 | BE110626 | AW915491 | BE349755 | Y00102 |
| AI232321 | AF169409 | K03250 | BF281802 | AA858509 |
| AI236624 | AW535358 | AA891859 | U56732 | AI105215 |
| NM_012984 | BE100202 | AF106657 | AF292116 | AI237580 |
| AI009623 | BF282629 | AI105272 | AW918457 | AJ293697 |
| AI010235 | BF556943 | AI170757 | BF408873 | BF565344 |
| AI179979 | BF563933 | AI233199 | BF409812 | NM_012581 |
| AI599143 | NM_019362 | AI409501 | AA800241 | AI170786 |
| AJ245707 | U55765 | AI410700 | AF050159 | AI231438 |
| AJ306292 | AI103327 | AI598467 | AF313411 | BF408022 |
| AW917197 | AW144790 | NM_017199 | AI317840 | AI598462 |
| BE108865 | U09793 | AI412209 | BF281384 | |
| BF545951 | BF395678 | AA851327 | AW919129 | AI112622 |
| BF556845 | M11563 | AA945202 | M20406 | AI172033 |
| AA944161 | NM_017194 | AA945634 | NM_021857 | AI175383 |
| AF021936 | NM_017267 | AB000491 | AF131294 | AI409049 |
| AF087674 | NM_017344 | AI102065 | AI234849 | AW533060 |
| AI232370 | U71293 | AI232205 | BF415080 | AW919094 |
| AI579023 | AI716115 | AW916594 | X58375 | AW920600 |
| AW141186 | AW141000 | AW921320 | AI102037 | BE101138 |
| AW916805 | BE109756 | BE114154 | AW251849 | BE107520 |
| BF291161 | BF284075 | AI411071 | AW527217 | NM_012674 |
| D14908 | AI716289 | AW142171 | NM_017066 | AA801218 |
| AI176016 | AA956784 | AW434007 | AF007549 | AF037199 |
| BE109747 | AF058714 | AW915587 | AI008386 | AI145784 |

TABLE 3-continued

7478 genes used to derive RTI signatures

| Accession # | Accession # | Accession # | Accession # | Accession # |
|---|---|---|---|---|
| BF282271 | AF090113 | BE109596 | AI104546 | AI177867 |
| D78482 | AF127390 | NM_017189 | AI176039 | BF283802 |
| AA893708 | BE113175 | AA899898 | AI235512 | BF396424 |
| AB001982 | BE113372 | AI410203 | AI407464 | BF405032 |
| AI716516 | BF288088 | AI705687 | AI549323 | BF416249 |
| BF401593 | NM_013223 | AW535229 | AW143285 | AI172159 |
| BF413556 | U40819 | AW915543 | AW916783 | AI409738 |
| NM_012916 | AA800025 | BF284679 | AW917522 | AW915402 |
| AA946011 | AA850358 | BE285207 | NM_012685 | L07073 |
| AI170668 | AI011497 | BF392605 | NM_012728 | U34985 |
| AI230723 | AI070137 | BF398046 | X53003 | AI556488 |
| AI598405 | AW532074 | AI008125 | AF098301 | BF115058 |
| AW143111 | NM_017186 | AI172184 | AF199411 | BF283742 |
| AW434242 | NM_021759 | BF550875 | AI231432 | AI103682 |
| AW920179 | U50194 | AF009603 | AI236772 | AW534533 |
| BF406407 | AA866426 | AI009591 | AI408517 | AW535909 |
| BE098266 | BF396082 | U77038 | BE108249 | AA894259 |
| D90166 | M35052 | U95727 | BE109637 | AF022952 |
| U07201 | M84009 | AA943100 | BE113111 | AI408852 |
| AA891834 | NM_017178 | AF022729 | BF398605 | AJ005113 |
| AA997458 | NM_019379 | AI137488 | NM_012836 | BE109161 |
| AI044229 | NM_021576 | AI145359 | NM_013216 | BF549710 |
| AI175551 | AF267197 | AI172450 | BF389352 | NM_012839 |
| AW921797 | AF276940 | AI175031 | AI071698 | NM_021653 |
| BF412792 | AI454081 | AI234810 | AI175474 | AI172465 |
| D13127 | AW141938 | AI408705 | AW917280 | AW536019 |
| D89514 | AW918816 | BE099401 | BF551315 | BE099732 |
| U55192 | BE103359 | BE120608 | AB016532 | D12770 |
| AI045819 | BE118465 | BF550426 | AI230220 | AW143273 |
| AW144075 | NM_017159 | BF561727 | AW915159 | AW523874 |
| AA945706 | NM_017311 | BF567649 | BE108853 | NM_019180 |
| AA945734 | AI103954 | NM_013103 | AA891830 | AA874838 |
| AF106945 | AA819871 | AI103456 | AI411897 | AF228049 |
| AF142629 | AF083418 | BF284887 | BE110722 | AI412591 |
| AF176784 | AW918470 | BF409560 | BE112999 | AW434329 |
| AI102248 | BF551138 | AI235238 | D26179 | AW914982 |
| BE095605 | AA800701 | BE109510 | L06238 | AW917734 |
| BE121438 | AF052042 | BF525029 | NM_017050 | BE111098 |
| BE329061 | AI013104 | AI172460 | U03708 | BF386111 |
| BF550271 | AI407821 | AI233875 | AW915834 | BF397542 |
| L31840 | AI598402 | AW916561 | BF284693 | BF549671 |
| X64411 | AI599376 | BE108405 | AA944036 | AI172191 |
| AA998893 | BF285247 | BF282009 | AI102429 | AI232217 |
| AI101490 | BF285980 | BF555349 | AI171775 | AW528823 |
| AW915318 | U68726 | BF556162 | AI406506 | BF565628 |
| AW915609 | X78604 | BF562149 | AW531891 | AI235353 |
| BF407740 | X90710 | NM_017241 | BE107157 | AJ300162 |
| D00680 | AI179119 | U26397 | BF404868 | AW918833 |
| AF010131 | AI411742 | AA900983 | D12771 | AW918775 |
| X79860 | AW142808 | AI965117 | AI893610 | D90102 |
| AA943981 | AA817907 | AI171654 | AB038387 | U87305 |
| AW916468 | AI179443 | AI177089 | AI170859 | AA892330 |
| NM_017101 | AB019693 | AI408686 | AI234035 | AI407409 |
| AA943600 | AI578861 | M97754 | BE105286 | AW144331 |
| AF314960 | NM_017213 | NM_017006 | BE111776 | AW915847 |
| AI008988 | U78889 | BE107747 | BF281438 | BF557668 |
| AI233241 | AA891790 | AB006461 | BF404419 | AA848342 |
| AW143117 | AA925922 | AI234008 | L36388 | AA942695 |
| BE101096 | BF408391 | AA944483 | X86789 | AA955630 |
| BE108272 | BF525153 | AF322224 | AA849782 | AF020045 |
| L34821 | AI407903 | AI763565 | AA874906 | AI137298 |
| AI177887 | AW914881 | AW916701 | AI169368 | AI179370 |
| AI231206 | BF409759 | BE103152 | BF283736 | AI410438 |
| BE108849 | AA859585 | BE108583 | NM_017021 | AI230134 |
| BF389882 | AF109393 | NM_017099 | AI138061 | AI410822 |
| BF550292 | AI009274 | AA817863 | AI412244 | BE099629 |
| AI010241 | AI013361 | AB030644 | AW915966 | AA801434 |
| BF558976 | AI013475 | AB042887 | BE105397 | AA819679 |
| AW915795 | AW525285 | AI103943 | BF417391 | AF084241 |
| AA894080 | BE103518 | AI170377 | U18942 | AW155444 |
| BE097615 | BE114137 | AI179991 | U75973 | AW918431 |
| BE108899 | BF289044 | AW435010 | X62952 | BE098309 |
| BE113057 | J05030 | AW526079 | AA848834 | BF407209 |
| BF407452 | AF036344 | BF419074 | AF327562 | AI178489 |
| BF550795 | AI137471 | BF552916 | AJ238717 | AW434972 |

| Accession # | Accession # | Accession # | Accession # | Accession # |
|---|---|---|---|---|
| BF555867 | AI145625 | M64711 | AW918775 | AA848526 |
| D13871 | AI172211 | AA800210 | BE104931 | AF063447 |
| NM_019220 | AW919132 | AA850498 | BE119692 | AF218575 |
| U72994 | BE112948 | AA893230 | BF283247 | AI170251 |
| AI170827 | BF283612 | AF115282 | BF555980 | AI235480 |
| BE113005 | BF284840 | AI169619 | BF564461 | AW144226 |
| BE117511 | BF414261 | AW531530 | NM_013058 | AW251666 |
| BF389478 | BF522056 | AW919429 | U48246 | AI013913 |
| BF412016 | D13061 | BE102505 | AI013699 | AI137301 |
| U57362 | U46034 | BF419925 | AI409741 | AJ001184 |
| AI012356 | AA799661 | M76591 | AW142955 | AW917946 |
| AI169243 | AA875055 | NM_013063 | BE096047 | BE112415 |
| BF281787 | AA943094 | AF072124 | BE101311 | AF245040 |
| BF287768 | AF037350 | AI177645 | BE109604 | AI136871 |
| BF396114 | AF244349 | AW918369 | BF289328 | AI177706 |
| U68544 | AI180400 | BE120038 | BF393085 | AI180454 |
| AA800232 | AI603627 | BF284819 | BF551339 | AI231601 |
| AI104857 | BE095490 | BF406693 | L37293 | BE108326 |
| AI105461 | BE109529 | NM_012578 | AI010342 | BE115880 |
| AI230228 | BE113119 | NM_017353 | AA851945 | BF394214 |
| AI412612 | NM_020089 | AI101475 | AA943868 | BF399328 |
| AW140530 | AW140531 | AI176781 | AA963282 | L10072 |
| BF555370 | AI176792 | AI411194 | AJ293948 | NM_012592 |
| AI170769 | AI236760 | AI705731 | AW143480 | NM_012793 |
| AI171280 | AI598324 | AW141990 | AW915268 | AB042599 |
| AI179677 | BE107173 | AW253902 | BE107438 | AF156981 |
| AI410505 | L46865 | AW524571 | BF556273 | AI176323 |
| BF403332 | NM_012987 | BF113371 | BF559875 | AI317817 |
| AW142852 | NM_017175 | BF285393 | M23984 | AI599641 |
| BF286955 | AA817895 | L26450 | NM_012997 | AW920443 |
| NM_012515 | AA859508 | M34384 | AA892298 | BE097245 |
| AI013928 | AI010432 | NM_020306 | AI029960 | BE109513 |
| AI176626 | AI169228 | U15211 | AI409930 | AA801206 |
| AI233205 | AW534781 | AA850551 | AI716131 | AF231010 |
| AW142713 | BF390657 | AF051895 | AW526697 | AI413033 |
| AW142877 | NM_017207 | AI406290 | BE100193 | AW143939 |
| AW915294 | AF090347 | AI412323 | BE108131 | AW531093 |
| BF392695 | AF030377 | U65007 | BE113228 | BF282636 |
| BF397773 | AI102519 | X66842 | BF567904 | U48247 |
| M32061 | AI177143 | AB026288 | M81766 | AA849715 |
| X62528 | AI232354 | AI717447 | Y08981 | AF020046 |
| AA849497 | AW522044 | AW142440 | AW144637 | AI412580 |
| AB026291 | AW917726 | AW527204 | AI009167 | AI600237 |
| AI317813 | BE106275 | AW915676 | AI408865 | AW915560 |
| AI407483 | BF282212 | BE109266 | AI575703 | AW918480 |
| AI535483 | BF401710 | BF390003 | AW141463 | BE111685 |
| AW433595 | J02997 | AI103914 | AW143992 | BF281285 |
| BE108976 | AA848338 | AI170783 | AW918108 | BF396317 |
| M59742 | AI454466 | AI713210 | BE105452 | BF548520 |
| NM_012613 | AI555844 | BE098845 | U19485 | D50580 |
| BE113624 | BE098873 | BE102816 | AA946490 | U34841 |
| BF406637 | BF395080 | BF283510 | AB040807 | Y17319 |
| U92803 | BF414124 | BF391673 | AF039033 | AW918273 |
| AA850785 | BF546361 | X56541 | AF092207 | BE121325 |
| AB020759 | AW144002 | AA800172 | AI072958 | NM_012980 |
| NM_019187 | AA893237 | AW917796 | AI411999 | BF396534 |
| NM_020976 | AF277902 | BE107459 | BE109075 | BF404409 |
| X96488 | AI145039 | BF399791 | AW399614 | J03753 |
| AF272662 | AW143197 | L31884 | M29295 | NM_013006 |
| AW144391 | AW918637 | AI012263 | NM_012665 | AA817867 |
| BE099953 | BF284879 | AI233726 | Z83868 | AA819812 |
| BF282288 | BF565705 | AI408104 | AI101393 | AI169599 |
| BF282645 | U11685 | AI555237 | AI547421 | AI227919 |
| BF413969 | U13253 | BF285079 | AW143757 | AW919050 |
| AA874952 | AB017793 | BF417363 | AW525128 | NM_013076 |
| AW915060 | AI230988 | M84488 | BE108832 | U09229 |
| BE104111 | AI385140 | NM_021997 | BF403323 | AA945103 |
| BF283001 | AI407991 | AA858786 | BF407165 | AB018546 |
| BF284914 | AW434026 | AA894084 | BF555033 | AF182946 |
| L32591 | BE100014 | AW918999 | M58716 | AI180031 |
| AI010234 | BE109057 | D90036 | NM_017188 | AI407985 |
| AI233766 | BE119961 | NM_021684 | AB047002 | AI410886 |
| AI716240 | BF397933 | AA800597 | AI232269 | AW915104 |
| AW254017 | AF034214 | AA892281 | AW918541 | BF407878 |
| AW919336 | AF190798 | AI169225 | BF523077 | BF414947 |

TABLE 3-continued

7478 genes used to derive RTI signatures

| Accession # | Accession # | Accession # | Accession # | Accession # |
|---|---|---|---|---|
| BF415023 | AI010660 | AI234095 | L11319 | D10655 |
| J05029 | AI170570 | AI411077 | M23601 | M92042 |
| NM_019385 | AW526160 | AI639139 | NM_017305 | NM_017231 |
| AA799515 | AW531675 | AW433942 | AI411520 | NM_019335 |
| AA925559 | BE111118 | AA892483 | BE108919 | NM_020073 |
| AI011736 | BE118222 | AI104485 | BF558507 | NM_021847 |
| AI102877 | BF555119 | AI407945 | NM_013090 | BE109039 |
| AI176623 | NM_017025 | AI409108 | Z83035 | AA850736 |
| BE098468 | AA892339 | BE095970 | AB002466 | AI407932 |
| BF550402 | AB002406 | BE101099 | AI230056 | AJ005425 |
| NM_021770 | AF203906 | BE107434 | AI410833 | AW143263 |
| AA819398 | AI010233 | D32207 | AI555566 | AW917908 |
| AA946128 | AI175028 | NM_013034 | AI598648 | BE106888 |
| AF151377 | AI406667 | X89963 | AI716218 | BE111752 |
| AI177663 | AI407482 | AI231190 | BE101448 | BF282437 |
| AI412090 | AJ242554 | AI412736 | BE102671 | BF290638 |
| AI412292 | AW434419 | AW433944 | BE118605 | AF016049 |
| BE102889 | AW521367 | AW917545 | BF555974 | AA892897 |
| BF408844 | BF283772 | BF283384 | AA817722 | AB015433 |
| BF564899 | BF388772 | BF420549 | AI233194 | AA834830 |
| NM_012634 | BF400697 | AA944568 | AI408375 | AW141787 |
| AA924526 | BF550302 | AI072892 | BE109600 | AW143141 |
| AA944278 | NM_017225 | AI105210 | BF567692 | BF548116 |
| AF094821 | AB026057 | AI236773 | NM_013147 | NM_012571 |
| AW144383 | AI172214 | AI406363 | AF085693 | AI175536 |
| NM_017251 | AI235950 | AI408954 | AI171807 | BF554895 |
| U53475 | AI409024 | AI412011 | AI598414 | AA892364 |
| AA850801 | AW253750 | AW915292 | AW915580 | AB020022 |
| AF012714 | AW535136 | AW915499 | BF550554 | AI175499 |
| AF146738 | AW917211 | BE113053 | D63665 | AF177478 |
| BE103926 | NM_017356 | BF282223 | AW254190 | AF323615 |
| BE109586 | AF061266 | AI169291 | BF555084 | AI071688 |
| BF396467 | AI012352 | BF399098 | NM_021754 | AI006295 |
| NM_019381 | AI060043 | AA946357 | AI009029 | AW915256 |
| U72660 | AI412018 | AI008952 | AI227700 | AI178647 |
| U83897 | AI600031 | AI103937 | AI409145 | AF072509 |
| AA851296 | AW433866 | AI227742 | AW525288 | AI172156 |
| AI176848 | AF139830 | BF547641 | NM_013190 | AW527880 |
| AI407459 | AF205604 | U93197 | NM_021750 | BE113354 |
| AI411005 | AW252550 | AA924945 | AI175586 | BF407799 |
| AW142370 | AW916799 | AF000942 | AI411060 | U07181 |
| AW252152 | BE111887 | AW535349 | AJ001529 | AB020504 |
| AW916013 | AI102290 | BF558075 | BF282544 | BF283685 |
| AW916792 | AI233162 | AI411332 | BF408448 | BF405110 |
| BF387153 | AA799789 | BF285720 | AA851230 | BF388153 |
| NM_019341 | AI011711 | BF557889 | AA944380 | AI172274 |
| BE111801 | AI102236 | AA944526 | AI176442 | AF159626 |
| AA892271 | AI411240 | AB049189 | AI237621 | BE115860 |
| AI008961 | AA799301 | AI101322 | AI409180 | NM_013028 |
| AW918092 | AI236816 | AI102495 | AI410943 | AW140640 |
| BF282185 | AI409186 | AJ277881 | AI411979 | BF393884 |
| BF395777 | AI012573 | BF409313 | BE108923 | NM_013185 |
| BF398045 | AI172116 | AA818820 | BF386302 | NM_017024 |
| BF420629 | AI236323 | AI102873 | D30035 | AW916148 |
| BF557739 | BF283075 | AI179142 | NM_012586 | BE113380 |
| J03637 | M69056 | AI230778 | X56228 | BF285301 |
| Y12009 | AI105441 | BF285078 | AF003944 | D90035 |
| AI175375 | AI407500 | NM_012659 | AI013474 | AF220455 |
| AI230185 | AI170752 | U18650 | AI101500 | AI104326 |
| AW251213 | AI172417 | AI013775 | BF284242 | AW140537 |
| M81639 | AI412239 | AI411964 | U58857 | M94548 |
| AA945090 | D85580 | BE109603 | AI029291 | AA924352 |
| BE111755 | J03933 | BE114159 | AI170751 | AW916619 |
| BF419380 | L27513 | M86870 | BE112253 | AW917712 |
| AI409032 | NM_012911 | AB005549 | NM_021848 | BE108877 |
| AW144517 | AF281018 | AI231193 | AI071187 | BF284713 |
| AW525342 | AI013788 | AI385277 | BF405880 | AA799636 |
| AW914215 | BF399587 | AI409841 | BF548241 | AI407904 |
| BE103434 | M81687 | AW915241 | M93271 | AW254590 |
| BF389721 | AI413058 | BF398378 | NM_019222 | AW917661 |
| BF397663 | AF069525 | J05214 | U82623 | BE104941 |
| BF411381 | AI060118 | NM_012818 | AI410415 | BF393950 |
| NM_012846 | AI407064 | AF01909 | AW142953 | X87885 |
| NM_017216 | BF558513 | AI104376 | AW434978 | AI169383 |
| AW435310 | AA875011 | AI228233 | BE100035 | AI412413 |
| AW917572 | AA891774 | AI639162 | BE108780 | NM_012528 |
| BE108192 | AA892554 | AW917587 | NM_021760 | AI412230 |
| U76997 | AI715257 | BE100208 | AA849752 | AW525071 |
| AA892567 | BE113288 | BE108905 | AB003042 | AF061947 |
| AA999042 | BF551361 | NM_019280 | AI236861 | BF389157 |
| AI232065 | AA892346 | NM_019622 | BE099603 | AI008969 |
| AI599031 | AI234858 | AA944162 | BF400873 | AW142549 |
| AW915803 | AI602172 | AI137972 | BF551369 | BE098806 |
| AW916305 | AW915466 | AW528847 | BF563786 | BF396191 |
| BE100201 | BF417386 | AW920802 | J00696 | M64300 |
| BE105305 | BF551118 | L35767 | NM_012966 | NM_017187 |
| D17447 | D14013 | AW143336 | AI236376 | AW915800 |
| L02121 | NM_012947 | AW144084 | AI407946 | BF282620 |
| M20133 | AA998435 | AW252169 | AW144223 | BF401275 |
| M34253 | AF080568 | AW528454 | BF283130 | AW917258 |
| AW919017 | AI045590 | AW915763 | L19658 | AI233133 |
| AA875129 | AI070591 | BF419241 | AA801116 | AI408930 |
| AA900046 | AW915160 | BF557396 | AI011704 | AW918153 |
| AA946441 | BF285089 | M58340 | AW144504 | BE109152 |
| BF288288 | BE109201 | AI170384 | AB010467 | BF416533 |
| BF562779 | BE109644 | AI410837 | AI102685 | NM_017246 |
| U54632 | BF281325 | AA894189 | AI177409 | AA946356 |
| AW915140 | BF523098 | AF119667 | AI229166 | AB017711 |
| BE109575 | D30795 | AF228307 | AW918105 | AI178752 |
| AA899489 | L09653 | AI234719 | BE113010 | AI599125 |
| AI111840 | NM_017105 | AI410917 | BF281834 | AW144760 |
| AI412967 | BE103894 | AJ001044 | BF386665 | BE108884 |
| AI575671 | AA799981 | BE107298 | BF394140 | BF284699 |
| BE100155 | AA943811 | AW916684 | X13549 | AA956764 |
| NM_013055 | AF077195 | BF389719 | U82626 | AI112512 |
| NM_019246 | AI236778 | BE108876 | AA943793 | BE107281 |
| AI231333 | AW143201 | AI411399 | AI105167 | AI176713 |
| AW523114 | AW254246 | BE118972 | AW144315 | AI178763 |
| AW523679 | AW916618 | H35082 | AI236054 | AJ299016 |
| BF284300 | X04959 | L34049 | BF389493 | BF406240 |
| U06713 | AA800199 | AW143157 | BF400662 | AF184920 |
| AI105154 | AA819716 | AW533321 | AI230729 | AI072236 |
| BE109143 | AA946074 | BF412594 | BE115551 | AW917568 |
| BF567763 | BF396729 | BF567585 | AI012951 | BE112921 |
| NM_019208 | U39044 | AW142367 | AW917662 | M73714 |
| U04933 | AI104251 | BE121429 | BE113247 | AI102744 |
| BE096021 | AI231564 | BF407916 | BE099563 | AI232494 |
| BE113323 | AI231789 | M86235 | BF548170 | AI233702 |
| BE121314 | AW253339 | AI009759 | AA849756 | BF284127 |
| BF407511 | AW524478 | AI407545 | AI229596 | BF405996 |
| NM_017079 | BE110652 | AW918385 | AF158379 | BF522695 |
| NM_017174 | BE117114 | BE101157 | AI170263 | AI412601 |
| AA849031 | BF404464 | AA799507 | AI234844 | BF412389 |
| AA859343 | BF563403 | AA818132 | AI639157 | BF414438 |
| AA943765 | D50564 | AI102046 | AW915774 | AA799576 |
| AI175728 | NM_017033 | AI171975 | AI232784 | AF296131 |
| AI228548 | AI101900 | AI172271 | AW916344 | AI385216 |
| AI230073 | AI413051 | AI230110 | BF408552 | BE110949 |
| AW433847 | AW917849 | BE102814 | AI233916 | BF284939 |
| AW915824 | BE100016 | BE118552 | AI409258 | BF555949 |
| BE098021 | BF404932 | BF404472 | BE098359 | BF564549 |
| U79661 | BF416377 | NM_013221 | BF418913 | L20900 |
| AI175762 | U23443 | NM_012573 | J04112 | Z16415 |
| AW918595 | AI408984 | AA944463 | AA945604 | AI229684 |
| BF281282 | AI411771 | BF281215 | AB017544 | AI406527 |
| X78949 | AF065387 | AA894318 | AI170948 | AI409951 |
| AA963096 | AI176933 | AI009656 | AW143214 | BE098713 |
| AA998971 | BE101089 | AI010721 | BF283454 | M31788 |
| U84038 | M22631 | AI012456 | BF523555 | U14533 |
| AI071470 | NM_012609 | AI137208 | U70825 | AI178912 |
| AI172579 | AF192757 | AI176483 | AW144499 | BF555429 |
| AI717053 | AI170933 | NM_013042 | AI010430 | AI598321 |
| AW918732 | AW529588 | AA818571 | AI706767 | BE111696 |
| BF283743 | AW530272 | AA943149 | AW915737 | L20822 |
| AI144583 | AW918408 | AI169160 | AW918850 | U08141 |
| BE102535 | BF283302 | AI411217 | BF283053 | AA800519 |
| AA849729 | L20821 | BF282194 | AA799614 | AF016047 |
| NM_017200 | U04319 | BF401587 | AB032899 | AI233267 |
| AW913858 | BF410753 | NM_021594 | AI406853 | AW527592 |
| AI012474 | AF286006 | AA891221 | AW527606 | AI071703 |

TABLE 3-continued

7478 genes used to derive RTI signatures

| Accession # | Accession # | Accession # | Accession # | Accession # |
|---|---|---|---|---|
| AI412614 | AW252511 | BF556691 | BE112252 | AI145019 |
| AI412626 | AA892319 | M97380 | BE101101 | AW915155 |
| AJ130946 | AF065438 | U40628 | AA799666 | BE108840 |
| BF558459 | AI102139 | AW914919 | AA944403 | H35178 |
| X16481 | AI236798 | BE107373 | AI704799 | M11942 |
| AI410901 | AW916666 | NM_017274 | BF398009 | M73808 |
| AW915787 | BE113034 | AB008161 | D85435 | Y12708 |
| BE108235 | BF284695 | BF288270 | AI233765 | AB017638 |
| BE108381 | U36786 | BF397445 | AA800539 | AI169242 |
| BF549121 | AF036760 | BF416387 | AA892044 | AI233232 |
| BF559056 | AI177061 | NM_013111 | AA942808 | AI237681 |
| AF051155 | NM_019372 | NM_019123 | AA946508 | AI143114 |
| AI412014 | AA892300 | AF121893 | AW915559 | AW913929 |
| BE107155 | AF032872 | Y15748 | BF282349 | BE113268 |
| BE109130 | AI103962 | AA800044 | BF398332 | NM_017048 |
| Y08172 | AI176002 | AW144441 | AW143568 | AA957492 |
| AI598359 | AW916151 | BF414262 | AW916347 | AF094609 |
| NM_017151 | BE111638 | AA848367 | BF408957 | AI009654 |
| AW528874 | AB031014 | AI178206 | AW915669 | AI013906 |
| BF550453 | AA892294 | AI229655 | AA800699 | AI171617 |
| AA893193 | AI177845 | AI406371 | AI011749 | AW531909 |
| AF181992 | AI411497 | BE117002 | AI104431 | BF393126 |
| AW144745 | AW253895 | BF282296 | AI170825 | X13058 |
| AW252105 | AW915264 | AW433959 | AI575445 | Y17326 |
| AW526756 | AW916138 | AF029310 | AW251630 | AI801094 |
| BF399124 | AB020879 | AI103375 | BF287135 | AI169140 |
| U87627 | AI171276 | AI176541 | BF420680 | AI232722 |
| AI104348 | AI712840 | AI227815 | BF548086 | AI236270 |
| AI231785 | AJ000347 | AI411985 | AA942949 | AW915791 |
| AI411141 | AJ292524 | AW142847 | BF388434 | U41803 |
| BE110537 | AW142931 | BE113048 | AA892829 | AA893241 |
| M11185 | AW144646 | AI179335 | AB002151 | AI228540 |
| AF029690 | BF403923 | AA801136 | AI170414 | AI317827 |
| AI010722 | BF420067 | AA817945 | AI233729 | AI575026 |
| AW252820 | NM_019275 | AA850525 | AI236101 | BE104107 |
| AW914860 | BE107208 | AA850909 | AI412255 | BF282890 |
| BF405883 | AI103616 | AA891818 | BE101485 | BF287032 |
| L16532 | AW144313 | AI104296 | BE110671 | BF398047 |
| AI012438 | AW529753 | AI231812 | BF283122 | BF419646 |
| BE329046 | AW915952 | AW252855 | BF414192 | NM_017348 |
| AI136513 | AW918376 | BE103222 | NM_017013 | AB024333 |
| AI169330 | BF404589 | BF288776 | AI102745 | AI105205 |
| AI171772 | BF410846 | BF394038 | NM_021676 | AW918593 |
| AI407001 | BF419489 | BF397229 | AA799550 | BE100453 |
| AI548694 | BF567996 | BF558902 | AB008538 | BE102815 |
| AW920624 | X62322 | NM_012804 | AF334379 | BE103430 |
| BE115875 | AI044638 | NM_016988 | AI235934 | BF282594 |
| BF564158 | AI598988 | AI176331 | AI408244 | BF397523 |
| AA800290 | BE112781 | AI013800 | AI704755 | BF408216 |
| AW434213 | BF393577 | AI412560 | BF282119 | BF558463 |
| AI231846 | BF414252 | AW914984 | BF392959 | NM_017112 |
| AI408197 | BF558120 | AW919694 | BF409371 | AA849991 |
| AW525033 | Y17325 | BE113234 | NM_013166 | AA892496 |
| BF284076 | AI105265 | BE113330 | X87106 | AA894233 |
| M36074 | AI112074 | BF398543 | AI013041 | AI010295 |
| U60063 | BE099063 | M57299 | AI172285 | AI011448 |
| AI169278 | BE101628 | NM_016986 | AI411057 | AI229529 |
| AA801230 | BF549638 | NM_017153 | AW524453 | BE105699 |
| BF413204 | AW915928 | BF550580 | AI172029 | BE118683 |
| M94040 | U21662 | U25808 | AI180458 | AI598320 |
| NM_012669 | AA893505 | AA924151 | BE102485 | BF281741 |
| Y12517 | AI058276 | AB003400 | BF550566 | BF285339 |
| AA819729 | AI172267 | AI227672 | BF556846 | BF549027 |
| AF054826 | AI177016 | AI406500 | NM_013033 | X15958 |
| AI180337 | AI233728 | AW253963 | AF030358 | AA818203 |
| AI234533 | AI406932 | AW914642 | AI176121 | AW916939 |
| BE105565 | AI412180 | AW918527 | AI598881 | BE113338 |
| BF564263 | AW143212 | BE101505 | AW143543 | BF408856 |
| NM_012866 | BE108162 | BF282984 | AW915481 | BF548630 |
| NM_019152 | BE111673 | BF399447 | C06665 | BF557793 |
| AA944438 | AI060197 | U44979 | NM_017201 | BF568009 |
| AB011531 | AI230388 | AA942726 | NM_017281 | M29472 |
| AF110025 | AI408502 | AA944828 | Z83044 | U75928 |
| AI145630 | BE108850 | AI169053 | AI058938 | AI009818 |
| AI176996 | BE329450 | AI171242 | AI137569 | AI317880 |

| Accession # | Accession # | Accession # | Accession # | Accession # |
|---|---|---|---|---|
| AW141869 | BF398626 | AW915015 | AW527421 | AI412086 |
| M54926 | AA819234 | BE110412 | NM_012776 | AW917096 |
| AI169607 | AI103467 | BE113269 | AI177863 | BF285334 |
| AI169746 | AI177412 | U78977 | AI406964 | BF288060 |
| AW915955 | AI229902 | AA848503 | AI411212 | BF290997 |
| BF282899 | AW915152 | AF244895 | AI556246 | BF407158 |
| BF400575 | AW916942 | AW435017 | U62940 | BF420447 |
| U64030 | AW917815 | BE108968 | AA800570 | BF556463 |
| AF259504 | AW919586 | BF405135 | AA946434 | AA998047 |
| AI171230 | BF291214 | AA850872 | AI407954 | AI231781 |
| AI229647 | AA943831 | AA944332 | AI170671 | AI236726 |
| AI235502 | AF034582 | AI600085 | AI409070 | AJ003004 |
| AW523709 | AF077000 | AI600108 | BE113315 | AW531275 |
| BE108860 | AI412298 | AW433865 | AA818128 | AW918257 |
| BF419854 | L12384 | AW913942 | AB028626 | BE108494 |
| L25331 | AI102688 | AW916661 | AW915815 | BE111850 |
| AA818113 | AI232248 | AW921139 | BE101212 | BE113375 |
| AF056034 | BE103304 | BE101171 | BF559919 | BE120015 |
| AI407095 | BE109671 | BE106523 | AA875045 | NM_017264 |
| AW915655 | BE112899 | BE107223 | AI137420 | AA926279 |
| BF387477 | NM_017361 | BF522863 | AW251313 | AA946382 |
| BF549379 | AA849734 | BF563261 | AW915638 | AB008571 |
| BF555532 | AA924717 | AI406651 | AW917594 | AI013657 |
| L37085 | AI232347 | BE096104 | BF524281 | AI176468 |
| AA817752 | AJ004912 | BE101124 | BF556698 | AW520324 |
| AA858600 | BE095620 | BE109118 | AI233262 | BF283406 |
| AI169490 | BF398121 | BF280414 | AI233718 | BF418890 |
| AI575402 | BF417396 | BF396629 | AI598371 | BF420754 |
| AW143173 | NM_017015 | BF403937 | AW141873 | BE106191 |
| AW529960 | X94351 | NM_013222 | BE095971 | D21800 |
| BE095474 | AA893217 | NM_019259 | BE109900 | AA799499 |
| BE108346 | AA943578 | NM_019259 | BE109900 | AA799499 |
| BE109072 | AB028934 | AI412015 | BF283091 | AA892127 |
| BE110542 | AI172177 | AI169353 | NM_019206 | AA893171 |
| NM_019299 | AW251501 | AW252811 | AA963094 | AF311055 |
| AA893811 | AW919497 | NM_012619 | AI012074 | AI169365 |
| AI178257 | BE111972 | NM_012946 | AI236754 | AI407130 |
| AI711105 | BE118440 | AA851239 | AW918097 | AW527971 |
| AW142280 | BF283418 | AA899150 | AW919037 | AW916168 |
| AW915107 | BF420144 | AI171607 | AW919937 | NM_021745 |
| BE115558 | AI232357 | AW915146 | BE349725 | AI103988 |
| AA964789 | AI412958 | BF412293 | BF282686 | BE109599 |
| AI169729 | AW251310 | AB037424 | BF549603 | BF523605 |
| AI172272 | BF417793 | BE110618 | BF407149 | AI175803 |
| AI177492 | BF419240 | NM_017326 | AA924654 | AI556502 |
| BF284775 | U19614 | AI073176 | AW144382 | AI59995 |
| BF398680 | AW525945 | AI411198 | AW915749 | AW917738 |
| BF410951 | AA801212 | BF398587 | BF281388 | BF284345 |
| AI175767 | AI639285 | AA955157 | BF282084 | M62388 |
| AI599956 | AA800191 | AI105145 | BF283385 | AA924152 |
| BE100802 | AA800535 | AI231011 | BF400719 | AI600216 |
| BF407563 | AW142925 | AI236640 | AI177621 | AW523737 |
| AA893590 | BE108810 | AI412002 | AI575104 | NM_019144 |
| AA944576 | BF399618 | BE110561 | BE112007 | Y00350 |
| AI169375 | X67654 | BE111986 | AA848795 | AA893208 |
| AW521376 | AA893532 | U15138 | AA894262 | AI703715 |
| AW918620 | AA944158 | BF397956 | AI230432 | AW916925 |
| AW918940 | AI105243 | AA799709 | AI548620 | BE099060 |
| BE110557 | AI233763 | AI070397 | AW917543 | J05405 |
| NM_012875 | AA851386 | AI102943 | BE115626 | AA799331 |
| AF095741 | AA866432 | AI231777 | AI009222 | AA944053 |
| AI231196 | AA946017 | BF551377 | BE108018 | AF184893 |
| AJ245646 | AI105117 | AB018791 | AI235192 | AI172269 |
| AW525089 | AI598410 | AI008971 | BF283084 | BE112892 |
| AW528792 | AW141364 | BE102266 | NM_012595 | BF419731 |
| BF410042 | AW532663 | BF399504 | AI178818 | D50696 |
| NM_017169 | AA800763 | AA800001 | AW525229 | AB032178 |
| AI227832 | AA998468 | AB010954 | C06787 | AI012381 |
| AI104378 | AW142276 | AF179370 | D83948 | AI180252 |
| AI170527 | AW914992 | AI171990 | Z71925 | AI228249 |
| AI230061 | BF285344 | AW915681 | AA945915 | AI230278 |
| AW921738 | BF561196 | AW918311 | BF287826 | AI408770 |
| BF419366 | AB017188 | NM_017182 | M75153 | AI409748 |
| AA892780 | AI406280 | X93352 | M83675 | AW433870 |
| AA875425 | AW915764 | AA924980 | AA858879 | BF419628 |

TABLE 3-continued

7478 genes used to derive RTI signatures

| Accession # | Accession # | Accession # | Accession # | Accession # |
|---|---|---|---|---|
| AW917015 | AA945568 | AF172640 | AI231773 | M61142 |
| BF398144 | AI176477 | AI101380 | AI232273 | NM_021849 |
| BE101784 | AI599407 | AI179992 | BE107540 | U66322 |
| AI111559 | BE113340 | AI717425 | BE113490 | AI406508 |
| AI169149 | BF549893 | AW916433 | BE120629 | AW915566 |
| AI175019 | AA892273 | BE098799 | L11004 | BE115600 |
| AI177410 | AA899959 | BF397603 | X74226 | BE116507 |
| BE107245 | AF285103 | AI102027 | AA858867 | AI171632 |
| BE118650 | AI176465 | AI104258 | AA859922 | AI007841 |
| NM_012985 | AI411365 | AI454943 | AF067728 | AI599286 |
| BF407964 | BE100986 | AI059108 | AW920774 | BE349648 |
| AI103129 | BF289928 | BE101766 | BE099950 | L11696 |
| AI234816 | BF565365 | BF282301 | BF407170 | AA800277 |
| AI175507 | AI111991 | BF415017 | AF110195 | AA819086 |
| BE119615 | BF286941 | BF420639 | AI012785 | AI172459 |
| BF408841 | AF200359 | NM_012789 | AI412143 | BF397894 |
| AI137756 | AI009363 | NM_017299 | AW253985 | AI407555 |
| AW434991 | AW915716 | AI411436 | AW914085 | AI556546 |
| NM_019238 | BF284754 | AJ303456 | BE112582 | AI577393 |
| AF069306 | BF523646 | AF044058 | BF286237 | BF281749 |
| AI599945 | AA894030 | AI410001 | BF399633 | AF144701 |
| AI137114 | AI713140 | AW525660 | AA945062 | AW141326 |
| BF557792 | NM_012960 | AI412949 | BE112384 | AI410481 |
| BF420654 | AA891821 | AI600036 | BF285023 | AB041723 |
| AI059234 | AW917596 | AW253367 | AA800665 | BF281200 |
| AI232643 | AI100850 | BE104143 | AI178806 | AA943011 |
| BE113423 | AI102689 | AA799783 | AI406906 | BE096986 |
| AA892993 | AI179136 | AI716491 | AJ225623 | AI044721 |
| X13817 | AW253642 | AW921162 | AW918039 | BE116383 |
| AW915662 | BE118414 | AF110026 | BF407819 | BE111699 |
| AB006450 | BF404027 | AI013011 | AA849757 | AI104034 |
| AI233857 | BF414266 | AI411227 | AI170714 | AI548730 |
| AW915056 | AI412024 | AI101580 | BE109614 | BE113022 |
| AI171211 | AW919474 | AI598381 | BE116918 | BE113201 |
| AW140925 | AA801308 | AW920761 | AI011510 | NM_013102 |
| AF032120 | AA818914 | BF558116 | BE115034 | AI170354 |
| AI169648 | AF120111 | AI555567 | NM_012670 | BF411424 |
| AW918604 | AI102947 | BE099224 | X96663 | J03624 |
| BF397588 | AI409731 | BE112202 | AI145851 | NM_012556 |
| NM_019213 | AW254068 | BE117946 | BF547710 | AW143082 |
| AA894297 | AW913868 | BF282388 | AW528625 | AF199322 |
| BE104415 | BF398537 | AA800521 | BE349838 | Z46957 |
| BF282678 | AW526283 | AA849788 | BF389726 | L06040 |
| NM_019334 | AI412192 | AF281304 | BF523622 | AF180350 |
| AI169328 | AI412357 | AI010455 | BE111787 | AB040802 |
| AI172092 | AI716902 | AI144663 | AI170768 | BE109138 |
| AW528057 | AW434064 | AW915194 | BE113043 | NM_021695 |
| AF026476 | BF396493 | BF544320 | BF282314 | NM_019125 |
| AF136585 | AA800576 | AA944449 | M57547 | X92495 |
| AW918068 | AI579376 | AW142350 | AA858518 | AW141928 |
| NM_019331 | BE113316 | AW531382 | AI575433 | X00469 |
| AA925303 | BF406661 | AW915412 | AA818520 | AA799329 |
| AI007987 | AI233172 | AY017337 | AA893517 | AA818947 |
| AI229046 | AF110732 | BE096311 | AF165892 | AI178768 |
| BF420055 | AI102991 | BF417071 | AI179365 | AI010317 |
| AW143287 | AA891940 | AF315374 | AI230346 | NM_013165 |
| AI105345 | BE100586 | NM_017177 | BF406604 | BF563201 |
| BF413977 | AI233751 | BF404344 | BE113454 | D10041 |
| BF398712 | AW916097 | AI555009 | AI171781 | AF097723 |
| AI408162 | BE109950 | AW919046 | AI179316 | U89744 |
| AW523409 | AI172301 | BF549833 | AI171367 | M58364 |
| BF283600 | AW520767 | AA850288 | BE109901 | BF398051 |
| U69485 | BE109512 | AI411153 | BE329347 | AW434139 |
| BE109521 | BF420279 | AW916463 | AI410096 | NM_021656 |
| AA944494 | BF393934 | BF282695 | AI411531 | AF205717 |
| BF282132 | AA800258 | AI410079 | BE110545 | L33916 |
| BF417400 | AI171764 | AI411278 | BE111677 | AW527564 |
| NM_012891 | AI706892 | M62763 | AW141664 | L27059 |
| AA946375 | BE110530 | AI412491 | AW143711 | NM_013021 |
| AA955172 | BF410389 | AW915621 | NM_019359 | AA946655 |
| AF255305 | AI412276 | BE101165 | AI411113 | U02096 |
| AI169359 | AW433846 | AI145899 | AW913987 | M31176 |
| AI408455 | AF002251 | AW917752 | BE095840 | U22830 |
| BF396218 | AI104146 | BE115557 | BF411317 | AW143269 |
| BF548597 | AI454536 | AA819400 | BE101129 | M55050 |
| BF557304 | AJ005424 | AB049151 | BE100823 | AI548036 |
| U93692 | AI233276 | AI172464 | BE101292 | M98820 |
| AI232657 | AI716471 | AW141870 | U53512 | AI007936 |
| BF414143 | AI230758 | NM_019252 | BE113035 | AW141286 |
| BF556841 | BE109711 | AI007877 | L27651 | U38938 |
| NM_013092 | NM_017170 | AF311886 | AA875041 | X06942 |
| AF176351 | AI177747 | AA859768 | AW919685 | BF404901 |
| AA943126 | AI176502 | AF168795 | D14437 | D45920 |
| AW143102 | AI105086 | BF284341 | X99338 | NM_020074 |
| X78689 | NM_012971 | BE110633 | AF016180 | AJ000555 |
| BF550800 | AW916756 | M14952 | AI500969 | AA859556 |
| NM_013023 | L29419 | AI411426 | BE105541 | U69550 |
| NM_012844 | BF410589 | BF285557 | BE108368 | AI071605 |
| NM_013191 | X65083 | U34843 | U49235 | BF557670 |
| M22926 | BE111296 | AF007789 | U66292 | AF188699 |
| AI408780 | M63991 | D10693 | AI236780 | BF284311 |
| NM_012822 | NM_017044 | D88672 | AI599365 | AB000216 |
| U53449 | U76551 | AW918103 | NM_012896 | D79981 |
| BF285022 | D00569 | AF003598 | AI176810 | AW919217 |
| M96548 | BF399655 | NM_019241 | NM_012918 | NM_012526 |
| NM_012521 | Z50144 | NM_012694 | BF415072 | AW921292 |
| AI715955 | AI170387 | AI233253 | AB020019 | NM_013078 |
| BF404304 | NM_013154 | NM_012702 | AI170357 | BF555189 |
| U21954 | AW915339 | NM_012716 | AI716535 | AI045026 |
| Z96106 | AW919159 | NM_019223 | BF405610 | U79031 |
| BF550451 | AI172174 | Y07704 | AI176718 | M60753 |
| AF135115 | U04998 | X06423 | L27112 | BE113295 |
| X92097 | AF069770 | Z18877 | U08255 | AI111803 |
| AW918419 | D12978 | AI170265 | Y11490 | AI233752 |
| AW251839 | BF288153 | U28356 | BF408271 | L07736 |
| AW915423 | AI172352 | AA945099 | D16829 | BF401764 |
| AA893251 | NM_012744 | X95096 | AA946492 | AF072835 |
| AI229720 | U57063 | J04628 | AI598346 | X63995 |
| D49494 | L26009 | NM_013100 | NM_013196 | NM_012699 |
| X67859 | BE096501 | D63834 | AA946350 | AA891949 |
| BF394161 | AW918276 | AW920575 | BE108246 | NM_019371 |
| NM_021669 | AW918684 | AF203374 | AW141135 | BF417565 |
| AI406856 | NM_012826 | BE110695 | U81037 | NM_012892 |
| BE107032 | BF420059 | M31155 | AA946467 | BE107187 |
| NM_017158 | AF324043 | BE113362 | AI412189 | BE108224 |
| NM_017081 | NM_017076 | NM_017058 | AI180349 | L01702 |
| BF549748 | AF013598 | AW920993 | X95189 | AI177168 |
| NM_017136 | AF242391 | AI176592 | BE117941 | M59967 |
| AW143169 | AI170665 | X54467 | AW916860 | X98517 |
| AF082533 | AB018049 | AF150106 | BF523660 | AJ002556 |
| Z14119 | AA801173 | AJ002745 | NM_017192 | NM_013172 |
| BE113272 | AA818949 | BE104375 | U92802 | NM_017320 |
| BE121346 | AJ132352 | D83792 | BF285568 | AA943114 |
| D14048 | AA996961 | AF082534 | BF281904 | AF401491 |
| NM_021264 | J02811 | AF000973 | BF289566 | U31203 |
| X52477 | NM_013098 | BE109616 | BF410786 | AF024622 |
| NM_013104 | BF396151 | BF419319 | AI105417 | BF405059 |
| NM_020088 | AI408380 | V01224 | BF563404 |
| AI009128 | AF035963 | J03621 | U07609 | BF400779 |
| NM_012629 | AI231805 | U02315 | AI168935 | NM_019314 |
| NM_013041 | BF282647 | AW919325 | BF281135 | BF419671 |
| J04731 | AF054586 | BF282951 | L12025 | NM_019179 |
| NM_013178 | AB037937 | NM_020080 | U10697 | BF397726 |
| BE111869 | NM_017280 | X98746 | BF564840 | NM_020301 |
| AF012891 | AI599294 | AF154914 | AF163321 | D38104 |
| NM_019157 | AW918535 | BF558524 | NM_017278 | BF405932 |
| AI409500 | NM_012587 | AI232085 | BF398182 | BF399649 |
| AF100421 | NM_013069 | AW143890 | AW915563 | NM_012707 |
| NM_019290 | AW251335 | AI175907 | AA851914 | BF398696 |
| X68400 | AW251633 | BE097102 | U56859 | M88469 |
| AF141386 | BF542467 | BE111729 | AA848534 | AI236753 |
| BF403998 | BF565649 | AI172498 | AA944398 | M83196 |
| NM_019272 | AA892824 | AW915002 | AF022247 | AF067793 |
| U12402 | BE120309 | AW140991 | AW434092 | AI173506 |
| AI598429 | BF388912 | BE107195 | BE108809 | U48592 |
| BF414004 | AW434670 | BE117687 | BF404853 | BE113616 |
| BF549324 | BE110658 | U41164 | AB021971 | X07467 |
| Z49762 | NM_012900 | BF284897 | BE113076 | BF285915 |
| Z50051 | AF062594 | AI228240 | BF414136 | BF563467 |

TABLE 3-continued 7478 genes used to derive RTI signatures

| Accession # | Accession # | Accession # | Accession # | Accession # |
|---|---|---|---|---|
| U37026 | BF420163 | BF392884 | AI145380 | D16465 |
| AI577501 | U00964 | BF546209 | AA943794 | NM_019318 |
| AI235610 | AI044845 | AW918841 | AI146056 | U90888 |
| NM_013224 | BE113165 | U25967 | AI178808 | AA899951 |
| BE108347 | BF393078 | AI137259 | BE109381 | BF556350 |
| AI137751 | BF558742 | AA944308 | M55534 | U17971 |
| AW917981 | Z19087 | AI407975 | BE329415 | NM_019196 |
| BE116152 | AF150741 | AF168362 | AB003478 | AA874975 |
| BE120545 | U57049 | AI406533 | AF157511 | AF110023 |
| AW919982 | AA800382 | AW141129 | BF408990 | AJ225654 |
| BE109277 | AW917673 | AW915546 | BF551318 | AW915004 |
| U93851 | J04811 | BF288240 | L05084 | BE097085 |
| M87053 | AW918559 | U22424 | NM_021741 | BF285071 |
| BF283410 | BE099796 | AA800389 | BF553500 | AA801331 |
| M91597 | AB046606 | AJ223599 | BF564759 | BE109744 |
| AF030378 | BE098930 | NM_019147 | AI176478 | AI713217 |
| AJ305049 | AF079864 | AI045083 | AI454928 | BF396314 |
| M22253 | BF557269 | AJ132230 | AI599484 | NM_012921 |
| AA799450 | AA851305 | NM_017020 | AW917650 | U89280 |
| BE108756 | AF201901 | BE120578 | AB001089 | AW917574 |
| AF115435 | AI411955 | NM_017010 | BE098025 | BE105864 |
| BE109242 | AW143142 | BF282689 | BE101151 | U14914 |
| AW533482 | BE109664 | D17309 | BF282700 | AI227916 |
| BE11827 | AA900180 | L36088 | M74067 | AW920324 |
| NM_017149 | AF230638 | NM_012700 | AI232138 | BF281577 |
| AI598306 | BE101140 | NM_021593 | BE110691 | AI600068 |
| BE103482 | D37979 | U48245 | BF282674 | BF282471 |
| BE104535 | NM_012608 | NM_017154 | AF015949 | BF396350 |
| AA924724 | AI711110 | U89695 | AF054870 | M91214 |
| NM_013179 | NM_017286 | AI233818 | AI009608 | X82021 |
| X13722 | NM_019137 | BE113599 | AI411793 | AF062389 |
| AI178476 | AI411375 | J03025 | NM_012600 | BE116153 |
| AA800501 | BE118055 | U59672 | BF287843 | U56241 |
| AI169399 | AF008554 | U90829 | BE095997 | U67137 |
| BF281357 | D50864 | AA858794 | BE109638 | BE108748 |
| AW918387 | AF020346 | AI317854 | L14851 | AI172248 |
| BF408867 | NM_019145 | AJ009698 | M83679 | AW526316 |
| BF420653 | NM_021766 | NM_012742 | U14647 | BE107192 |
| U61184 | BE101094 | AB019120 | BF399595 | U17253 |
| AB006614 | BE109569 | AW918468 | BE112983 | X95577 |
| AW920729 | BE117893 | J04147 | AI232716 | AA600081 |
| U86635 | L33413 | NM_017129 | BE100617 | AA819316 |
| AA819339 | AA818892 | U25055 | BE101148 | BE113655 |
| AI233213 | M30596 | BF284768 | AA943573 | Y15054 |
| AI178556 | AW142966 | BF406261 | AI412866 | AA646222 |
| BF393799 | AI228955 | D30666 | BF388797 | AI511282 |
| BF408425 | AW523755 | Y00697 | BF403842 | AW915567 |
| AW142667 | AW918188 | AB022714 | NM_012624 | BE108177 |
| BF404316 | BF522212 | AF132046 | U78090 | BE115948 |
| BF555947 | AF036335 | AI178938 | AI176298 | AW915148 |
| NM_019165 | BE120354 | M22923 | AW523419 | BE107295 |
| U92072 | AF083269 | NM_012591 | AW917114 | BF395101 |
| AF156878 | AI235493 | AF093536 | M22756 | AI146156 |
| BE114418 | AI411056 | AI406525 | U48702 | AW919410 |
| AI179460 | L27058 | AI408017 | NM_012780 | AW144095 |
| NM_020081 | AW253040 | BF284776 | AA944552 | AW915236 |
| AI102524 | AA818020 | BE113205 | AI408249 | NM_012969 |
| NM_017150 | AW141878 | M14050 | U25281 | AW253398 |
| AB022209 | AW527440 | AA892918 | NM_012889 | BF282987 |
| BF285150 | BE113660 | NM_013050 | AB009372 | AF234260 |
| AI411991 | BF389120 | U42413 | J00750 | BF416935 |
| NM_012734 | AI411270 | AB016160 | NM_012834 | BE550779 |
| AW142654 | AW918441 | AI410127 | AA848305 | BF553981 |
| NM_012610 | BE102251 | NM_019384 | AI406532 | U30831 |
| AI176548 | BE109561 | AI102061 | NM_017110 | AI172415 |
| AA850242 | NM_017003 | AA946349 | NM_021774 | M64780 |
| BF396462 | AI236928 | NM_019256 | AI103955 | AI407187 |
| NM_012913 | AA891213 | AF008114 | AA818197 | BF408452 |
| AI145761 | AI407992 | AI230591 | AW520354 | BF413245 |
| AI411297 | Y09164 | BE101290 | Z21513 | M88096 |
| NM_017060 | BF550737 | NM_021661 | BE097309 | NM_017179 |
| AF281635 | X05341 | NM_017062 | BE118454 | AF279918 |
| U42388 | AI411422 | AI408969 | BF290106 | AI007974 |
| BF409208 | AW919170 | AW918198 | M31837 | AW144302 |
| AW142170 | AI763826 | AA800744 | AA955605 | BF402472 |
| AW143820 | BF288140 | AB028461 | AW918716 | BF416877 |
| BF282574 | X96589 | AW143077 | BF288254 | AI411670 |
| AF178689 | BF406991 | BE101126 | NM_012811 | X62660 |
| BE107098 | AA817836 | BF555858 | AB010960 | NM_017323 |
| BF407134 | X15834 | BF556693 | AF081582 | X73653 |
| L39018 | BF555544 | AI717140 | BF393949 | AW251852 |
| BE097840 | AB046544 | AF240784 | AI009820 | BF281178 |
| BE107410 | L13041 | AW916911 | AI229209 | AJ002942 |
| AI227686 | AF009511 | BF284509 | NM_012907 | NM_017214 |
| AW916943 | BF567426 | BF418775 | NM_016994 | AF177430 |
| AF227741 | NM_017161 | BF568015 | AW533098 | NM_017035 |
| NM_021670 | U90312 | AA800737 | BF404778 | AF100172 |
| X52196 | AF063851 | AI146063 | AF032925 | AW142717 |
| AB025784 | BF415013 | AI407061 | AA800046 | AI409727 |
| AI236120 | AA946014 | BF282483 | AA851302 | NM_021776 |
| AW915825 | BF287827 | AA800364 | AW914045 | U03491 |
| BE113365 | BE098800 | AA945579 | BE113101 | X02610 |
| BF393902 | AI712686 | BF392911 | BF407194 | AA818377 |
| BF556880 | BF404426 | NM_019122 | D86345 | AI599232 |
| AA894099 | J02962 | AA818602 | AI703713 | AW915797 |
| BF417476 | NM_020471 | AI172262 | BE109919 | BF285528 |
| U53882 | X89383 | M85299 | BE096027 | BF566689 |
| AF153012 | U25651 | NM_012770 | AI409037 | AI574745 |
| BF288244 | AI535308 | AA955527 | AW143190 | BE112950 |
| NM_012773 | AW434998 | AF222712 | BF396115 | X65948 |
| AW252115 | AW918031 | AW251686 | AW143156 | AI102758 |
| BE097244 | BE096652 | NM_017300 | AW917977 | AI231782 |
| NM_021590 | BF551160 | M64381 | X14773 | D88190 |
| BF282395 | NM_021866 | AI104432 | AI230732 | AI555819 |
| BE116554 | AW527690 | AW919837 | AI412740 | D21158 |
| U55836 | AI180050 | NM_017238 | BF406286 | M77246 |
| X16262 | AW917831 | AI012336 | NM_020101 | AI171651 |
| BF550679 | BE109095 | AW919892 | U81160 | AI548655 |
| AI170390 | BF408792 | NM_017243 | AI113186 | AI555457 |
| AW915776 | AF221622 | AF194371 | AA893584 | BF404590 |
| BF284067 | BF388220 | AI102802 | AF161588 | BF411162 |
| NM_019376 | D00036 | AI138048 | NM_013129 | NM_016996 |
| AI072251 | AI178019 | L38644 | AI170410 | AI101373 |
| U96490 | BE111361 | NM_013124 | BE096257 | AW918990 |
| AI007768 | BE111820 | X54862 | M29294 | BE107805 |
| AW921975 | AW915041 | AI178452 | U36992 | AI177022 |
| AA925469 | AW915273 | AI578745 | X66022 | AI411391 |
| AI102804 | AI556256 | L22294 | AA848437 | AA891551 |
| AW141615 | AA817802 | AI178361 | AA850317 | BE106307 |
| BF404439 | AI176838 | AW520781 | D13518 | BF393917 |
| NM_012807 | AI412114 | BE113015 | AI008964 | BE110638 |
| BE104961 | BE109712 | BF283407 | AI639504 | M69246 |
| BF281284 | AF254800 | AI639411 | AW919920 | AI227943 |
| AW915886 | AI406670 | AW526270 | AW920557 | BF524978 |
| BE120498 | U20999 | U08257 | AI308571 | U31352 |
| AI175533 | AB006137 | AI716159 | AI230578 | AI010423 |
| NM_020308 | AW433947 | AW143164 | AW915692 | M13979 |
| AI145869 | BF400588 | AW919130 | BE099875 | AI177590 |
| AW142932 | BE097982 | BE107279 | BF282648 | AI111863 |
| AW143294 | M85183 | AI236615 | AA850576 | AI235282 |
| AW251657 | AA892987 | BF291260 | AW915782 | AW919696 |
| AW525099 | AF106325 | NM_019350 | BE102100 | BF553948 |
| AW523504 | BE117939 | AA858745 | D17711 | AA858925 |
| AW915685 | BE119991 | AI598946 | AA998252 | AF033027 |
| BE115417 | BE126380 | AJ245648 | AW531386 | J05035 |
| AA945882 | AB033418 | AW530332 | BF402375 | AI710879 |
| AI177360 | AF068861 | AA957010 | AI101189 | NM_019163 |
| NM_021586 | AI231450 | AW915165 | AI410802 | U71294 |
| AI598507 | AW918920 | BF564460 | AI599568 | AA849987 |
| AW915843 | X73292 | AA849731 | L14684 | BE101435 |
| AI172024 | AW143907 | BF543359 | AF324255 | NM_020076 |
| AI176646 | BE113277 | AA944327 | U82591 | BF283735 |
| AI409051 | BF389143 | AW918368 | X59601 | BF394563 |
| AI409861 | AI105450 | BE100015 | AF214568 | AW917562 |
| BF281872 | AW526673 | BE100965 | AI406304 | AW918237 |
| AF026505 | AA848804 | BE110621 | U57715 | NM_012827 |
| AI009427 | BE115604 | NM_012653 | AI231433 | BE103793 |
| AI233343 | BE116180 | NM_013151 | AI602613 | AI169749 |
| BE109221 | BF419010 | AI176727 | AW140397 | AI454845 |
| D78610 | BF557276 | AW143676 | BE108985 | M25073 |

TABLE 3-continued

7478 genes used to derive RTI signatures

| Accession # | Accession # | Accession # | Accession # | Accession # |
|---|---|---|---|---|
| AW917185 | NM_012761 | BE109246 | BF285313 | AW916692 |
| NM_019368 | NM_020077 | AF176072 | BF289100 | AI177083 |
| AA800815 | AA818342 | AI170289 | D10554 | AI228159 |
| AF061873 | AI230596 | U27186 | M83107 | AW434103 |
| AW918233 | AI406712 | AW530292 | AI411222 | BE108388 |
| BF542548 | AI410452 | BF387258 | BE107075 | BF282088 |
| AA851282 | AI548615 | AI175556 | AF218826 | BF420183 |
| AI409150 | NM_021757 | NM_017168 | AI070523 | AW524523 |
| AW915035 | AW916774 | AW918991 | AI177379 | BF411622 |
| BF284983 | AW915540 | BF551808 | AI406469 | BF558866 |
| AW435159 | BE096098 | U36482 | AI598307 | U57391 |
| Y00047 | AI104256 | AA997745 | L19699 | X62277 |
| AI411360 | AI179391 | AI069922 | AA901066 | AA892240 |
| X78855 | AI556315 | BE107622 | BF412565 | AW251483 |
| AW251401 | BE109108 | BF567869 | M84719 | AW525372 |
| Z49858 | BF417010 | AW919868 | BE110574 | X67156 |
| AA944079 | BF548406 | BE118251 | BE120360 | AI231309 |
| AI172266 | NM_012749 | AW915682 | BF282675 | BF420064 |
| BE107489 | BF417442 | AI136709 | AI408993 | D50695 |
| BE116220 | AI407858 | NM_019201 | U96638 | |
| AA945713 | BF282381 | AA899160 | AW144669 | NM_017283 |
| AW920687 | D29960 | AB029559 | BE110128 | AF274057 |
| BF415422 | L26267 | AI409045 | BE113321 | AI409506 |
| AI177058 | AI229821 | AF117330 | BF392443 | AI412429 |
| AW532870 | AI230362 | BF523591 | BF556332 | BE116848 |
| BE108835 | AA891733 | AI411845 | X66370 | BF551342 |
| NM_020075 | BE109055 | AI502504 | AI178214 | AI137218 |
| AI102743 | BF281852 | AW143215 | AI230884 | AI171769 |
| AI169386 | AA799700 | BF098555 | AI556402 | AI412763 |
| BE109681 | BF414012 | AI009644 | U35245 | AA818692 |
| AI599479 | BF393863 | D87950 | U40188 | AI178158 |
| BF283237 | AB018253 | AA893640 | AI169635 | AI231286 |
| NM_012797 | AI072292 | AI009197 | AI410456 | AB006914 |
| AI171794 | M34477 | AI171088 | BF288651 | AI411156 |
| U27191 | AI236691 | AW921253 | BF397951 | AW916461 |
| L27339 | AI406487 | BE113399 | AF000578 | BF403712 |
| AW916023 | BF283073 | AF016252 | AW520760 | AI102486 |
| BE098778 | AI411772 | BF420684 | BE104290 | AI137233 |
| AF136943 | AW251612 | BF557013 | BE117164 | AI175494 |
| AI178272 | AW525370 | AI103146 | BF406590 | BE109633 |
| AI231505 | BF551370 | AI501407 | AI229833 | AB000199 |
| BE096516 | BF393595 | AW528778 | AI009089 | AI009094 |
| NM_012853 | AW143323 | NM_017282 | AI012598 | NM_017166 |
| U69487 | L28801 | AA893192 | AI228598 | AI408482 |
| AA944485 | NM_017037 | AF208499 | BF399093 | Z11994 |
| U26595 | BF285026 | BE107103 | L12382 | AI178922 |
| AA818910 | AA849958 | BF415001 | AI176042 | AI236063 |
| AI232346 | BF550748 | NM_017209 | BF562819 | AW526015 |
| AB048711 | AI409857 | BE111727 | X52140 | BE109952 |
| BE121333 | BF394528 | BE116914 | AA996888 | D26180 |
| AJ225647 | AI235367 | BF398071 | AI105088 | AA851369 |
| BF283417 | BE104454 | AI007924 | AI172150 | AI227996 |
| BF558071 | AW915120 | AI233773 | BE109232 | AA858649 |
| AI411527 | BE112971 | BF097153 | U73503 | AF216807 |
| AI235294 | AI102009 | BF281969 | AI170285 | AF323174 |
| U66461 | AW915541 | AI716436 | AW914009 | AA849774 |
| AA945069 | AW921544 | BF417252 | AW914041 | AF003926 |
| AF081503 | BE100576 | AI010312 | BE109628 | BF557601 |
| AI408928 | BE113248 | BE111694 | BF555169 | NM_013027 |
| AW920454 | Z29486 | BE113210 | AI179795 | AA848530 |
| BF414412 | AI169653 | BE117891 | BE102427 | AW529231 |
| BF419792 | AI176972 | AW435036 | BE111811 | BF557674 |
| AW252109 | AI176972 | AA943752 | NM_017313 | AA800803 |
| NM_012904 | AI502952 | AA800739 | AA819318 | AW919277 |
| AW918452 | BF550572 | AW915142 | NM_021752 | AW141131 |
| BE100774 | AW253429 | AW915484 | AW915445 | BF289154 |
| BF396644 | AF223951 | AI411205 | BF284328 | BE111731 |
| AA892362 | AF277899 | AF036255 | BF285068 | BE119400 |
| AI227985 | BF557299 | AI579643 | BF288092 | BF393862 |
| BE108201 | AW915121 | AA799544 | AW918538 | AW251199 |
| AA799313 | NM_017349 | BF414146 | BF282327 | AW526089 |
| AI236027 | AI406938 | AI102643 | BE101579 | AW919172 |
| BE120602 | AI010033 | AF302085 | BE116560 | BE110609 |
| X04070 | AI407930 | AW251641 | NM_012758 | AW142642 |
| X54640 | AI599023 | AA943815 | AA996543 | AW434308 |
| AA894305 | NM_012680 | AW253646 | BF415031 | BF554891 |
| AI229183 | Y00826 | AF221952 | AI410349 | AW254375 |
| AI411790 | AW254166 | BE109709 | AF134054 | AI235510 |
| AW143855 | BF411147 | BF549441 | AW916920 | AF219904 |
| BE118562 | AI408520 | AI172472 | AI385370 | BE115570 |
| AA892772 | BF283250 | NM_013113 | BE100607 | AI234173 |
| AA892922 | AW917768 | AI228624 | AI233786 | AW525042 |
| AA800249 | BF396485 | BE112237 | AI713324 | BE104891 |
| AA858572 | BF401591 | BF281954 | BF290678 | X71429 |
| AW918182 | AI169706 | AF170253 | BF414193 | BF283351 |
| D84667 | BE109678 | AI012264 | AI406350 | BF415054 |
| U89282 | NM_017163 | BF281319 | AI411530 | BF282715 |
| AI010433 | AA799691 | D38082 | BE111849 | AI010351 |
| BE113013 | BE104865 | AA946389 | AW916376 | AI112973 |
| BF396371 | BF284093 | BF523723 | AA799532 | BF558479 |
| D13124 | AI013075 | M57728 | AI170763 | X53232 |
| AA996628 | AW433875 | AA818582 | AW141730 | AW144324 |
| AB047556 | AW433883 | BE097279 | BE111512 | NM_017257 |
| AI137161 | BF418588 | BF550623 | AI102788 | AI169374 |
| AW252891 | AA955616 | BF407480 | BF284711 | AI555565 |
| BE111879 | AF227200 | AF087431 | AI103993 | AA800637 |
| BE115051 | BE097298 | AI232979 | BF557930 | AI009796 |
| AA945898 | AW914090 | AW251107 | BF563406 | AI407449 |
| AI012613 | M61219 | AW253004 | BF288328 | BF287028 |
| AI407067 | AW406413 | BF419187 | L26288 | AI145385 |
| BE116889 | AW143981 | AA891860 | M34043 | H35156 |
| X71873 | AW919527 | AI172500 | AB046442 | BF284885 |
| AA900562 | AA893621 | AA945753 | AF239045 | AI010413 |
| AI170409 | AW141940 | AW252110 | AI639012 | NM_012500 |
| BF400995 | AI137912 | AW254010 | AA942681 | AI175064 |
| M27893 | BF406514 | AW434299 | AF276774 | BE111765 |
| BF284313 | U00926 | M23674 | BE099976 | V01222 |
| AI230697 | AI178155 | AI169176 | AI412079 | BE116947 |
| AI575056 | AI716607 | AA851241 | AW507304 | NM_012883 |
| AW914867 | BG153368 | BE116927 | M75148 | NM_017094 |
| BE117683 | BF281865 | BF420717 | BE096995 | M33648 |
| AF025424 | AI175544 | BF282933 | AI716456 | AB032243 |
| AA859141 | AW914973 | AI228642 | AA957770 | L07578 |
| BE116512 | AW916823 | AI599819 | AA945696 | NM_017210 |
| AA946032 | BE099999 | BF411461 | BF397012 | D14046 |
| AI070399 | BE110645 | AA963071 | BF550545 | X79807 |
| BE108886 | AF002705 | AI171951 | D10854 | AW530379 |
| BF551148 | AW918614 | AI410391 | AA818089 | NM_012743 |
| AA942690 | AW917503 | NM_012552 | BF284830 | X68282 |
| AW914062 | BE113989 | AI009200 | Y07744 | AF062402 |
| BF408129 | BF284855 | BF281133 | BE114123 | AW251683 |
| NM_012852 | BF396478 | BF410771 | AF013967 | AW253843 |
| U12571 | AW143086 | AI045074 | L22022 | BE109532 |
| NM_017304 | AF304429 | AI137283 | NM_017190 | AA945866 |
| NM_019175 | AF073379 | NM_017049 | AI575072 | AW919439 |
| AI013038 | U23438 | AA891922 | BE111659 | BE098855 |
| X70706 | NM_021701 | M95738 | BF283830 | AA848420 |
| AB032827 | AW534166 | AI170382 | BE109642 | AI406499 |
| BF286192 | L15619 | BF398540 | AI070732 | AI406520 |
| AA892531 | BF398602 | AI145586 | BF283754 | BF410170 |
| U52103 | X15800 | BE110674 | BF405725 | AI232332 |
| BF412297 | M81642 | BF419044 | NM_013186 | U67140 |
| AI44958 | NM_012790 | U67138 | BF420043 | AA893191 |
| AF291437 | AB030947 | BF283759 | M55250 | AA817813 |
| U73174 | L08814 | L11007 | AA799784 | BE111345 |
| AI176327 | X58828 | NM_017248 | AI013110 | AA817817 |
| U06273 | NM_017017 | AW918345 | BF412643 | AI179413 |
| AF095449 | AF035156 | AB001321 | AI170664 | AI231827 |
| AF269251 | AI715321 | AI406494 | M94043 | AI579555 |
| NM_013127 | AW528005 | BE097282 | AI406275 | U46149 |
| X97831 | X52590 | AW435315 | AF039203 | BF390970 |
| X53477 | BE102840 | D37920 | AA818364 | BF405581 |
| NM_017284 | NM_017333 | AA892864 | BF393486 | AI045035 |
| NM_013225 | AW141761 | BF400782 | BE128566 | AW141446 |
| U66566 | AF011788 | AI231089 | BF563114 | AW915616 |
| S79760 | AB032551 | BF417360 | AI231290 | BE116574 |
| AW143231 | BF549260 | NM_017173 | BF414997 | NM_019124 |
| BF564152 | U53706 | X98399 | AW921546 | BE100609 |
| AW915661 | X68191 | Y13588 | AI044124 | NM_013130 |
| NM_012957 | M14053 | BF283107 | AA848639 | M35495 |

TABLE 3-continued

7478 genes used to derive RTI signatures

| Accession # | Accession # | Accession # | Accession # | Accession # |
|---|---|---|---|---|
| BE115943 | NM_019352 | AA799358 | BF395067 | L14936 |
| AW920769 | BF403999 | BE116101 | AW918011 | AI408827 |
| BE110731 | NM_012930 | AI575254 | AI072218 | AI410818 |
| Y16641 | AW920609 | AF016387 | BF553984 | BF411842 |
| M87067 | AW918854 | AW918052 | AI235222 | AI178134 |
| AF016183 | NM_013174 | L35771 | NM_017160 | BE107324 |
| D86373 | AA964289 | AF007108 | U78875 | BE111609 |
| J05181 | AB015746 | AW142311 | BE111770 | AI411088 |
| BE110547 | U78517 | AA819501 | AA800708 | AI407320 |
| NM_021696 | AJ223355 | AW144294 | M27905 | AI233452 |
| NM_021758 | AF104034 | Y00752 | AI172075 | AA850487 |
| NM_017230 | BF396709 | NM_012651 | M55075 | BF283861 |
| NM_017127 | BF404959 | AW251942 | AA944549 | AA800291 |
| BF557572 | U93306 | BF399135 | AA800004 | BF397919 |
| U05989 | AJ010750 | BF289492 | X51707 | D50694 |
| M35270 | BF281419 | AA946518 | AI179640 | AI412931 |
| BF406646 | AI715893 | BE107610 | X74125 | NM_017355 |
| AF269283 | AI548722 | NM_012594 | AI237077 | AI406390 |
| NM_021678 | AA818954 | AW143162 | AW143513 | BF407501 |
| X68101 | BE109116 | BF566346 | AF187814 | BE109573 |
| BF567821 | AW522132 | BE101876 | U51583 | AI009156 |
| AJ238278 | AW916153 | BF551593 | BF567845 | AW917598 |
| J04487 | AJ301677 | AF087433 | AW920343 | BF289001 |
| AF008197 | BF566748 | AA943764 | BE105589 | BF281975 |
| BF396279 | NM_017139 | NM_012747 | AI233266 | D83538 |
| M59814 | BF406213 | AI179315 | AW913871 | AI177053 |
| AI230548 | D10233 | BF548006 | AI009007 | BF393285 |
| L20823 | BE111690 | AI175454 | D21132 | D82928 |
| M29293 | AI407113 | | | |
| BF291213 | BF396256 | | | |
| AF017756 | AI180187 | | | |
| BE118425 | BE109634 | | | |
| BF556755 | AA944176 | | | |
| BF282147 | BF395125 | | | |
| BE108922 | | | | |
| BF402664 | | | | |
| L22339 | | | | |
| NM_013177 | | | | |
| AF110024 | | | | |
| AW143526 | | | | |
| BF555225 | | | | |
| X71916 | | | | |
| AI070303 | | | | |
| AA965185 | | | | |
| BE109656 | | | | |
| NM_017026 | | | | |
| D89375 | | | | |
| BE100771 | | | | |
| U54807 | | | | |
| X99326 | | | | |
| NM_019234 | | | | |
| AI598719 | | | | |
| AA801133 | | | | |
| U10894 | | | | |
| AI170303 | | | | |
| NM_019281 | | | | |
| L39991 | | | | |
| AA817968 | | | | |
| BF548743 | | | | |
| AI716480 | | | | |
| AB028933 | | | | |
| AA859631 | | | | |
| D85189 | | | | |
| NM_017104 | | | | |
| AA900434 | | | | |
| AF049344 | | | | |
| AI170376 | | | | |
| AJ007704 | | | | |
| Y13380 | | | | |
| AA893164 | | | | |
| AA894306 | | | | |
| AF051943 | | | | |
| BF558780 | | | | |
| X61677 | | | | |
| BF407203 | | | | |
| AI237636 | | | | |
| AF095740 | | | | |
| AI179711 | | | | |
| AW527815 | | | | |
| AA945149 | | | | |
| AF234765 | | | | |
| BE110624 | | | | |
| BF406562 | | | | |
| D00859 | | | | |
| BE109704 | | | | |

The signature used to predict the presence or absence of future renal tubular injury was derived using a robust linear programming support vector machine (SVM) algorithm as previously described (see e.g., El Ghaoui, L., G. R. G. Lanckriet, and G. Natsoulis, 2003, "Robust classifiers with interval data" *Report # UCB/CSD*-03-1279. Computer Science Division (EECS), University of California, Berkeley, Calif.; and U.S. provisional applications U.S. Ser. No. 60/495,975, filed Aug. 13, 2003 and U.S. Ser. No. 60/495,081, filed Aug. 13, 2003, each of which is hereby incorporated by reference herein). Briefly, the SVM algorithm finds an optimal linear combination of variables (i.e., gene expression measurements) that best separate the two classes of experiments in m dimensional space, where m is equal to 7479. The general form of this linear-discriminant based classifier is defined by n variables: $x_1, x_2, \ldots x_n$ and n associated constants (i.e., weights): $a_1, a_2, \ldots a_n$, such that:

$$S = \sum_{i}^{n} a_i x_i - b$$

where S is the scalar product and b is the bias term. Evaluation of S for a test experiment across the n genes in the signature determines what side of the hyperplane in m dimensional space the test experiment lies, and thus the result of the classification. Experiments with scalar products greater than 0 are considered positive for sub-chronic nephrotoxicity.

Signature Validation

Cross-validation provides a reasonable approximation of the estimated performance on independent test samples. The signature was trained and validated using a split sample cross validation procedure. Within each partition of the data set, 80% of the positives and 20% of the negatives were randomly selected and used as a training set to derive a unique signature, which was subsequently used to classify the remaining test cases of known label. This process was repeated 40 times, and the overall performance of the signature was measured as the percent true positive and true negative rate averaged over the 40 partitions of the data set, which is equivalent to testing 392 samples. Splitting the dataset by other fractions or by leave-one-out cross validation gave similar performance estimates.

Cross validation using 40 random iterative splits (80:20 training:test) resulted in an estimated sensitivity, or true positive rate, of 83.3%, and a specificity, or true negative rate, of 94.0%. Leave-one-out cross-validation produced similar results.

To test whether the algorithm is identifying a true pattern in the training set, but not a random data set, the labels for the 64 experiments were randomly assigned and a signature was derived and subject to cross-validation as above. This process was repeated 99 times. As expected, the average test log odds closely centered about zero (−0.004±0.86), with a range of −2.3 to 2.9. By comparison, the true label set had a log odds ratio of 4.4, which was significantly greater than expected by chance (p<0.0001).

Results

Using 7478 pre-selected genes whose accession numbers are listed in Table 3, the SVM algorithm was trained to produce a gene signature for renal tubule injury comprising 35 genes, their associated weights and a bias term that perfectly classified the training set. The 35 genes and the parameters of the signature are depicted in FIG. 1. Average impact represents the contribution of each gene towards the scalar product, and is calculated as the product of the average $\log_{10}$ ratio and the weight calculated across the 15 nephrotoxicants in the positive class listed in Table 2.

As shown in FIG. 1, the genes are ranked in descending order of percent contribution, which is calculated as the fraction of the average positive impact each gene in the positive training class has relative to the sum of all positive impacts. Genes with a negative average impact are considered penalty genes. The expression $\log_{10}$ ratio of each gene was plotted in the depicted "heat map" across all 15 treatments in the training set. The sum of the impact across all 35 genes for each treatment, and the resulting scalar product are presented along the two rows below the plot. The bias term for the 35 gene signature was 0.58.

The 35 genes identified represent 35 unique Unigene clusters. This 35 gene signature identifies compound treatments that are predicted to cause future renal tubular injury in the rat based on kidney expression data from short term (<=5 days) in vivo studies.

The product of the weight and the average $\log_{10}$ ratio across the 15 positive experiments in the training set indicated that 31 of the 35 genes are considered "reward" genes, as they represent expression changes that positively contribute to the signature score (i.e., the scalar product). The reward genes assure sensitivity of the signature by rewarding expression changes consistent with nephrotoxicity. A positive scalar product indicates the experiment is predicted to be positive for future renal tubular injury, while a negative scalar product indicates the experiment is negative for future renal tubular injury. The remaining 4 genes in the signature are considered "penalty" genes as they represent expression changes that negatively contribute to a scalar product. Penalty genes assure specificity of the signature by penalizing expression changes not consistent with nephrotoxicity.

The genes and bias term in the signature are weighted such that the classification threshold (i.e., zero) is equidistant, by one unit, between the positive class and negative class experiments in the training set.

Of the 31 reward genes, 15 have an average expression $\log_{10}$ ratio greater than zero and are therefore induced on average by the nephrotoxicants, while the remaining 16 are on averaged repressed by the nephrotoxicants. Examination of the expression changes across the 15 nephrotoxicants in the training set reveals that most genes are not consistently altered in the same direction by all treatments (FIG. 1). Instead, it is the sum of the product of the weight and $\log_{10}$ ratio (i.e., impact) across all 35 signature genes, less the bias, that results in an accurate classification. For example, Cyclin-dependent kinase inhibitor 1A (U24174) or the EST AW143082 are induced and repressed to varying degrees by compounds in the positive class, thus indicating that individual genes would be poor classifiers when used individually. This highlights the limitations of using single genes for classification and also illustrates the basis for signature robustness since classification decisions are not dependent on any one gene that may be subject to experimental error.

Example 4

Stripping of Renal Tubule Injury Signatures to Produce a Necessary Set of Genes

In order to understand the biological basis of classification and provide a subset of genes useful in alternative signatures for renal tubule injury, an iterative approach was taken in order to identify all the genes that are necessary and sufficient to classify the training set.

Starting with the 7478 pre-selected genes on the Codelink RU1 microarray, a signature was generated with the SVM algorithm and cross-validated using multiple random partitions (80% training: 20% test) of the data set. The 35 genes identified previously in the first signature (i.e., "iteration 1" in Table 4) as being sufficient to classify the training set were removed and the algorithm repeated to identify additional genes. This identified an additional 37 genes (i.e., the genes in "iteration 2" in Table 4) that were able to classify the training set with a log odds of 3.80. This approach was repeated until the test LOR of the model reached zero, which occurred after 14 iterations and which consumed 622 genes. Based on the first 5 iterations, 186 genes were identified to be necessary to classify the training set with a test LOR of 1.64 (Table 4), which is approximately 2 standard deviations greater than the average LOR achieved with random label sets. Importantly though, it identifies a reasonable number of genes with a demonstrated ability to uniquely discriminate nephrotoxicants with an approximate accuracy of 76%. These genes are listed in Table 4.

TABLE 4

186 genes identified to be necessary and sufficient to classify the training set.

| Probe | Iteration | Weight | Impact | Mean Logratio Positive Class | Mean Logratio Negative Class | Unigene ID | UniGene Description |
|---|---|---|---|---|---|---|---|
| AI105417 | 1 | −0.89 | 0.261 | −0.294 | −0.172 | Rn.8180 | neuronal regeneration related protein |
| BF404557 | 1 | −1.36 | 0.213 | −0.156 | 0.077 | Rn.50972 | ESTs |
| U08257 | 1 | 0.88 | 0.149 | 0.170 | 0.029 | Rn.10049 | Glutamate receptor, ionotropic, kainate 4 |

TABLE 4-continued 186 genes identified to be necessary and sufficient to classify the training set.

| Probe | Iteration | Weight | Impact | Mean Logratio Positive Class | Mean Logratio Negative Class | Unigene ID | UniGene Description |
|---|---|---|---|---|---|---|---|
| BF285022 | 1 | 1.46 | 0.143 | 0.097 | −0.013 | Rn.24387 | ESTs |
| AF155910 | 1 | 0.55 | 0.125 | 0.226 | 0.002 | Rn.92316 | heat shock 27 kD protein family, member 7 (cardiovascular) |
| AI144646 | 1 | 0.63 | 0.108 | 0.171 | −0.075 | Rn.36522 | gap junction protein, alpha 12, 47 kDa (Hs.) (DBSS_strong) |
| AI105049 | 1 | 0.82 | 0.104 | 0.126 | −0.018 | Rn.23565 | ESTs |
| AI227912 | 1 | 0.46 | 0.074 | 0.160 | −0.026 | Rn.873 | Sorting nexin 3 (SDP3 protein) (Hs.) (DBSS_strong) |
| AW916023 | 1 | −0.64 | 0.074 | −0.116 | −0.011 | Rn.6788 | Kelch-like ECH-associated protein 1 (Cytosolic inhibitor of Nrf2) (INrf2) (Rn.) (DBSS_weak) |
| BF403410 | 1 | 0.42 | 0.068 | 0.163 | 0.020 | Rn.23087 | *Homo sapiens* clone 25048 mRNA sequence (Hs.) (DBSS) |
| Y00697 | 1 | 0.63 | 0.067 | 0.106 | 0.048 | Rn.1294 | Cathepsin L |
| AW143082 | 1 | −0.30 | 0.056 | −0.186 | 0.361 | Rn.22057 | ESTs |
| AI599126 | 1 | 0.36 | 0.044 | 0.122 | −0.061 | Rn.8452 | inner centromere protein (Mm.) (DBSS_strong) |
| AI102732 | 1 | −0.31 | 0.035 | −0.113 | 0.064 | Rn.7539 | ESTs |
| AI176933 | 1 | 0.46 | 0.035 | 0.076 | −0.048 | Rn.23658 | ajuba (Mm.) (DBSS) |
| AF208288 | 1 | −0.27 | 0.034 | −0.127 | 0.043 | Rn.48779 | G protein-coupled receptor 26 |
| AF281635 | 1 | 0.43 | 0.021 | 0.049 | 0.002 | Rn.9264 | zinc finger protein 22 (KOX 15) |
| U24174 | 1 | 0.09 | 0.021 | 0.219 | 0.133 | Rn.10089 | cyclin-dependent kinase inhibitor 1A |
| AW142947 | 1 | −0.22 | 0.019 | −0.085 | −0.030 | Rn.61563 | ESTs |
| BF396132 | 1 | −0.26 | 0.014 | −0.055 | 0.004 | Rn.76362 | echinoderm microtubule associated protein like 2 |
| NM_012610 | 1 | −0.08 | 0.014 | −0.164 | 0.054 | Rn.10980 | nerve growth factor receptor |
| U57049 | 1 | −0.17 | 0.013 | −0.080 | 0.000 | Rn.10494 | methylenetetrahydrofolate reductase |
| AW520754 | 1 | −0.08 | 0.010 | −0.124 | 0.021 | Rn.15536 | potassium channel, subfamily K, member 3 (Hs.) (DBSS) |
| AI231846 | 1 | −0.13 | 0.008 | −0.059 | 0.032 | Rn.27 | ESTs |
| BE116947 | 1 | 0.05 | 0.006 | 0.126 | −0.078 | Rn.8045 | ESTs |
| AW917933 | 1 | −0.04 | 0.005 | −0.124 | 0.039 | Rn.28424 | ESTs |
| AW144517 | 1 | −0.05 | 0.005 | −0.097 | −0.004 | Rn.13780 | ESTs |
| AW920818 | 1 | 0.03 | 0.005 | 0.177 | −0.078 | Rn.11702 | macrophage activation 2 (Mm.) (DBSS) |
| AB021980 | 1 | −0.05 | 0.003 | −0.057 | 0.054 | Rn.32872 | delta-6 fatty acid desaturase |
| AF087454 | 1 | −0.29 | 0.001 | −0.004 | 0.033 | Rn.30019 | potassium voltage-gated channel, subfamily Q, member 3 |
| BE097309 | 1 | 0.41 | 0.000 | 0.001 | 0.004 | Rn.46694 | Peregrin (Bromodomain and PHD finger-containing protein 1) (Hs.) (DBSS_strong) |
| AW919837 | 1 | −0.05 | 0.000 | 0.010 | 0.042 | Rn.23432 | adrenergic, alpha-2A-, receptor (Hs.) (DBSS) |
| NM_013197 | 1 | 0.03 | −0.007 | −0.259 | −0.286 | Rn.32517 | aminolevulinic acid synthase 2 |
| BF396955 | 1 | 0.77 | −0.050 | −0.065 | −0.228 | Rn.41236 | PC4035 cell-cycle-dependent 350 K nuclear protein (Hs.) (DBSS_weak) |
| BF281149 | 1 | 1.34 | −0.057 | −0.042 | −0.226 | Rn.3137 | Hypothetical protein KIAA0008 (Hs.) (DBSS_weak) |
| AI412011 | 2 | 3.38 | 0.279 | 0.082 | 0.005 | Rn.3738 | RIKEN cDNA 0610012G03; expressed sequence AI839730 (Mm.) (DBSS_weak) |
| BF419406 | 2 | −0.94 | 0.159 | −0.168 | −0.026 | Rn.26560 | ESTs |
| NM_021682 | 2 | −0.53 | 0.125 | −0.234 | −0.032 | Rn.42884 | kilon |
| AF136583 | 2 | 0.66 | 0.115 | 0.174 | −0.024 | Rn.12100 | serum-inducible kinase |

TABLE 4-continued 186 genes identified to be necessary and sufficient to classify the training set.

| Probe | Iteration | Weight | Impact | Mean Logratio Positive Class | Mean Logratio Negative Class | Unigene ID | UniGene Description |
|---|---|---|---|---|---|---|---|
| NM_020308 | 2 | 0.94 | 0.111 | 0.118 | −0.025 | Rn.28393 | a disintegrin and metalloproteinase domain (ADAM) 15 (metargidin) |
| BE109152 | 2 | 1.60 | 0.103 | 0.064 | 0.011 | Rn.19642 | Red protein (RER protein) (Mm.) (DBSS_strong) |
| AI176739 | 2 | 0.41 | 0.083 | 0.205 | 0.005 | Rn.22359 | KIAA1002 protein (Hs.) (DBSS_moderate) |
| AI228233 | 2 | 0.67 | 0.076 | 0.113 | −0.017 | Rn.25139 | epsin 2 (Hs.) (DBSS) |
| AF007549 | 2 | 0.55 | 0.075 | 0.136 | 0.026 | Rn.10734 | golgi SNAP receptor complex member 2 |
| AI232347 | 2 | −2.15 | 0.070 | −0.032 | 0.012 | Rn.102 | chromosome 14 open reading frame 114 (Hs.) (DBSS_moderate) |
| AW915996 | 2 | −0.48 | 0.054 | −0.114 | 0.094 | Rn.19250 | T00260 hypothetical protein KIAA0605 (Hs.) (DBSS_strong) |
| AA819832 | 2 | −0.40 | 0.054 | −0.136 | 0.141 | Rn.34433 | period homolog 1 (*Drosophila*) (Hs.) (DBSS) |
| AW524724 | 2 | −0.34 | 0.052 | −0.156 | −0.002 | Rn.95059 | ryanodine receptor type 1 (Mm.) (DBSS_strong) |
| BE103916 | 2 | −0.72 | 0.046 | −0.064 | 0.020 | Rn.26832 | ESTs |
| BF283302 | 2 | 0.56 | 0.046 | 0.081 | −0.008 | Rn.226 | ESTs |
| X68878 | 2 | −0.17 | 0.040 | −0.244 | −0.050 | Rn.11022 | synaptosomal-associated protein, 91 kDa |
| D00403 | 2 | −0.44 | 0.039 | −0.088 | 0.031 | Rn.12300 | Interleukin 1 alpha |
| AI145385 | 2 | −0.79 | 0.035 | −0.044 | −0.025 | Rn.3580 | ESTs |
| AI317854 | 2 | −0.22 | 0.032 | −0.143 | 0.012 | Rn.20362 | ESTs |
| AI231432 | 2 | 0.58 | 0.030 | 0.051 | −0.025 | Rn.6983 | hypermethylated in cancer 1 (Mm.) (DBSS_moderate) |
| AA996961 | 2 | −0.34 | 0.029 | −0.088 | 0.071 | Rn.12469 | DNA-repair protein complementing XP-A cells (Hs.) (DBSS_moderate) |
| NM_012971 | 2 | −0.26 | 0.025 | −0.098 | 0.058 | Rn.9884 | potassium voltage gated channel, shaker related subfamily, member 4 |
| BF397726 | 2 | 0.43 | 0.020 | 0.047 | −0.076 | Rn.18639 | NF-E2-related factor 2 (Rn.) (DBSS_weak) |
| AW527217 | 2 | −0.20 | 0.017 | −0.088 | −0.027 | Rn.23378 | ESTs |
| AA799789 | 2 | 0.25 | 0.016 | 0.065 | −0.026 | Rn.30163 | ESTs |
| NM_013190 | 2 | −0.59 | 0.015 | −0.026 | 0.001 | Rn.4212 | Phosphofructokinase, liver, B-type |
| AI576621 | 2 | 0.16 | 0.013 | 0.082 | 0.027 | Rn.24920 | ESTs |
| AA943149 | 2 | 0.81 | 0.010 | 0.012 | −0.002 | Rn.7346 | ALEX3 protein (Hs.) (DBSS_strong) |
| AW253895 | 2 | −0.12 | 0.006 | −0.055 | 0.011 | Rn.3382 | BRCA1 associated protein-1 (ubiquitin carboxy-terminal hydrolase) (Hs.) (DBSS_strong) |
| BF283340 | 2 | −0.09 | 0.005 | −0.057 | 0.028 | Rn.20857 | ESTs |
| AF073379 | 2 | −0.11 | 0.005 | −0.046 | 0.015 | Rn.10169 | glutamate receptor, ionotropic, N-methyl-D-aspartate 3A |
| AA799981 | 2 | −0.14 | 0.005 | −0.034 | 0.032 | Rn.6263 | ESTs |
| AF237778 | 2 | −0.18 | 0.003 | −0.017 | 0.086 | Rn.88349 | calcium/calmodulin-dependent protein kinase II alpha subunit |
| AI175375 | 2 | −0.14 | 0.003 | −0.019 | −0.025 | Rn.24087 | ESTs |
| AJ130946 | 2 | 0.13 | 0.002 | 0.014 | −0.096 | Rn.2949 | karyopherin (importin) alpha 2 |
| AI012120 | 2 | 0.25 | −0.004 | −0.016 | −0.149 | Rn.17809 | ESTs |
| AW252871 | 2 | 0.54 | −0.078 | −0.145 | −0.370 | Rn.12774 | cell proliferation antigen Ki-67 (Mm.) (DBSS_moderate) |
| J03863 | 3 | 0.70 | 0.163 | 0.233 | 0.208 | Rn.9918 | serine dehydratase |
| U19614 | 3 | 2.55 | 0.161 | 0.063 | −0.005 | Rn.11373 | lamina-associated polypeptide 1C |
| M19651 | 3 | 0.78 | 0.131 | 0.168 | 0.052 | Rn.11306 | Fos-like antigen 1 |
| AI407719 | 3 | −1.78 | 0.111 | −0.063 | 0.161 | Rn.20359 | ubiquitin specific protease 2 (Hs.) (DBSS) |
| BF396629 | 3 | 2.54 | 0.111 | 0.044 | −0.051 | Rn.16544 | patched homolog (*Drosophila*) (Hs.) (DBSS) |

TABLE 4-continued 186 genes identified to be necessary and sufficient to classify the training set.

| Probe | Iteration | Weight | Impact | Mean Logratio Positive Class | Mean Logratio Negative Class | Unigene ID | UniGene Description |
|---|---|---|---|---|---|---|---|
| BF290678 | 3 | 2.25 | 0.109 | 0.049 | −0.015 | Rn.40449 | heterogeneous nuclear ribonucleoprotein G (Mm.) (DBSS) |
| BE101099 | 3 | −1.84 | 0.109 | −0.059 | −0.008 | Rn.35019 | parathyroid hormone regulated sequence (215 bp) |
| AI070303 | 3 | −1.13 | 0.098 | −0.086 | 0.019 | Rn.21284 | pancreasin (Hs.) (DBSS_moderate) |
| AA925559 | 3 | −1.06 | 0.078 | −0.074 | 0.031 | Rn.25196 | RIKEN cDNA 2610027L16 [(Mm.) (DBSS_strong) |
| AB005549 | 3 | 0.58 | 0.056 | 0.097 | −0.026 | Rn.31803 | three-PDZ containing protein similar to C. elegans PAR3 (partitioning defect) |
| AI717140 | 3 | −0.59 | 0.043 | −0.072 | −0.001 | Rn.22400 | ESTs |
| AA858817 | 3 | −0.23 | 0.040 | −0.171 | 0.079 | Rn.22047 | T46271 hypothetical protein DKFZp564P1263.1 (Hs.) (DBSS_moderate) |
| BF284897 | 3 | 0.54 | 0.035 | 0.064 | 0.027 | Rn.18772 | hypothetical protein FLJ10579 (Hs.) (DBSS_moderate) |
| AW914881 | 3 | 0.27 | 0.034 | 0.123 | 0.036 | Rn.22383 | ESTs |
| BE106459 | 3 | −0.21 | 0.033 | −0.157 | −0.037 | Rn.20259 | ESTs |
| BF283556 | 3 | −0.14 | 0.027 | −0.188 | 0.019 | Rn.7829 | *Homo sapiens* clone 23785 mRNA sequence (Hs.) (DBSS) |
| M63282 | 3 | 0.31 | 0.016 | 0.050 | 0.084 | Rn.9664 | Activating transcription factor 3 |
| AW533663 | 3 | 0.08 | 0.014 | 0.174 | 0.124 | Rn.41672 | Proline oxidase, mitochondrial precursor (Mm.) (DBSS_strong) |
| L19656 | 3 | −0.92 | 0.013 | −0.014 | 0.048 | Rn.10552 | 5-hydroxytryptamine (serotonin) receptor 6 |
| NM_012852 | 3 | 0.11 | 0.009 | 0.083 | −0.008 | Rn.34834 | 5-Hydroxytryptamine (serotonin) receptor 1D |
| AA946230 | 3 | −0.22 | 0.008 | −0.039 | −0.023 | Rn.47222 | ESTs |
| BF405135 | 3 | −0.36 | 0.008 | −0.022 | 0.018 | Rn.51262 | ESTs |
| AA818949 | 3 | −0.14 | 0.007 | −0.052 | 0.002 | Rn.20419 | DnaJ homolog subfamily B member 12 (Hs.) (DBSS_moderate) |
| X79860 | 3 | −0.36 | 0.006 | −0.017 | 0.066 | Rn.65877 | H1SHR mRNA |
| AW253907 | 3 | −0.08 | 0.005 | −0.064 | 0.066 | Rn.98601 | ESTs |
| X89603 | 3 | 0.05 | 0.004 | 0.091 | −0.049 | Rn.11325 | metallothionein 3 |
| AA858649 | 3 | −0.50 | −0.002 | 0.004 | 0.004 | Rn.16864 | chromosome 13 open reading frame 9 (Hs.) (DBSS_strong) |
| AW529588 | 3 | 0.61 | −0.003 | −0.005 | −0.040 | Rn.28180 | ESTs |
| BF550800 | 3 | 0.16 | −0.004 | −0.023 | −0.307 | Rn.36317 | ESTs |
| BE111296 | 3 | 0.18 | −0.014 | −0.079 | −0.174 | Rn.19339 | ESTs |
| AI113104 | 3 | 1.77 | −0.086 | −0.048 | −0.262 | Rn.12343 | protein regulator of cytokinesis 1 (Hs.) (DBSS_moderate) |
| U53706 | 4 | −1.14 | 0.159 | −0.139 | −0.021 | Rn.10288 | mevalonate pyrophosphate decarboxylase |
| L36459 | 4 | 0.89 | 0.152 | 0.171 | −0.036 | Rn.10045 | Interleukin 9 receptor |
| BF410042 | 4 | 4.02 | 0.151 | 0.038 | −0.030 | Rn.31227 | cardiac lineage protein 1 (Mm.) (DBSS) |
| AW915655 | 4 | −2.26 | 0.129 | −0.057 | 0.000 | Rn.14962 | ESTs |
| AA944518 | 4 | −1.07 | 0.102 | −0.096 | 0.019 | Rn.34351 | ESTs |
| NM_012939 | 4 | −0.19 | 0.079 | −0.408 | −0.002 | Rn.1997 | Cathepsin H |
| BF408867 | 4 | −0.37 | 0.059 | −0.157 | 0.013 | Rn.35618 | mitochondrial translational release factor 1-like (Hs.) (DBSS_moderate) |
| AW915454 | 4 | −0.26 | 0.052 | −0.204 | −0.028 | Rn.14822 | ESTs |
| BE113132 | 4 | −0.37 | 0.042 | −0.112 | 0.124 | Rn.22381 | guanine nucleotide exchange factor for Rap1; M-Ras-regulated GEF (Hs.) (DBSS) |
| AW143273 | 4 | 0.72 | 0.040 | 0.056 | −0.020 | Rn.11888 | Rec8p, a meiotic recombination and sister chromatid cohesion phosphoprotein of the |

TABLE 4-continued 186 genes identified to be necessary and sufficient to classify the training set.

| Probe | Iteration | Weight | Impact | Mean Logratio Positive Class | Mean Logratio Negative Class | Unigene ID | UniGene Description |
|---|---|---|---|---|---|---|---|
| | | | | | | | rad21p family (Hs.) (DBSS) |
| AW915107 | 4 | 0.70 | 0.039 | 0.055 | −0.023 | Rn.19003 | ESTs |
| BE110577 | 4 | 0.96 | 0.038 | 0.040 | −0.008 | Rn.14584 | ESTs |
| AW141985 | 4 | 0.39 | 0.034 | 0.088 | −0.008 | Rn.13195 | ATP-binding cassette, sub-family C (CFTR/MRP), member 4 |
| AW140530 | 4 | −0.35 | 0.029 | −0.083 | 0.005 | Rn.7679 | tumor susceptibility protein 101 (tsg101) gene (Mm.) (DBSS) |
| BF420720 | 4 | −0.31 | 0.026 | −0.083 | 0.030 | Rn.23998 | ESTs |
| AW144399 | 4 | −0.78 | 0.025 | −0.032 | 0.068 | Rn.15255 | hypothetical protein FLJ10652 (Hs.) (DBSS_moderate) |
| AI411605 | 4 | −0.30 | 0.024 | −0.079 | −0.095 | Rn.20056 | ESTs |
| NM_019123 | 4 | 0.38 | 0.021 | 0.055 | −0.025 | Rn.88072 | sialyltransferase 7c |
| AW920802 | 4 | 0.50 | 0.019 | 0.037 | −0.021 | Rn.36609 | ribosomal protein L5 (Hs.) (DBSS) |
| AI228598 | 4 | −0.70 | 0.018 | −0.026 | 0.036 | Rn.11771 | ESTs |
| AI175454 | 4 | 0.18 | 0.013 | 0.072 | −0.002 | Rn.17244 | procollagen-proline, 2-oxoglutarate 4-dioxygenase (proline 4-hydroxylase), alpha polypeptide II (Hs.) (DBSS_strong) |
| AI009623 | 4 | −0.08 | 0.011 | −0.135 | −0.073 | Rn.13924 | ESTs |
| AI235282 | 4 | −0.20 | 0.011 | −0.053 | 0.004 | Rn.22436 | Low-density lipoprotein receptor-related protein 1 precursor (Hs.) (DBSS_strong) |
| NM_012564 | 4 | −0.06 | 0.009 | −0.159 | −0.100 | Rn.1437 | Group-specific component (vitamin D-binding protein) |
| BE095865 | 4 | −0.35 | 0.009 | −0.025 | 0.104 | Rn.21852 | calcium channel, voltage-dependent, alpha 1I subunit (Hs.) (DBSS) |
| AF291437 | 4 | −0.40 | 0.009 | −0.022 | −0.058 | Rn.39124 | leucine rich repeat protein 3, neuronal |
| AF176351 | 4 | −0.26 | 0.009 | −0.032 | 0.017 | Rn.54003 | nuclear receptor coactivator 6 |
| AB027155 | 4 | 0.15 | 0.008 | 0.057 | 0.027 | Rn.44869 | phosphodiesterase 10A |
| BE116569 | 4 | 0.34 | 0.008 | 0.024 | −0.009 | Rn.15835 | zinc-finger protein AY163807 (Hs.) (DBSS_strong) |
| AA894210 | 4 | 0.05 | 0.004 | 0.091 | 0.082 | Rn.85480 | ESTs |
| AJ237852 | 4 | −0.04 | 0.003 | −0.058 | 0.065 | Rn.30023 | sodium channel, voltage-gated, type11, alpha polypeptide |
| AJ305049 | 4 | −1.09 | 0.002 | −0.002 | 0.075 | Rn.64632 | interleukin 10 receptor, alpha |
| NM_017186 | 4 | −0.03 | 0.002 | −0.070 | −0.015 | Rn.30042 | glial cells missing (*Drosophila*) homolog a |
| AA800004 | 4 | 0.04 | 0.001 | 0.024 | −0.063 | Rn.6269 | Septin 4 (Peanut-like protein 2) (Brain protein H5) (Hs.) (DBSS_strong) |
| NM_012614 | 4 | 0.05 | 0.001 | 0.012 | 0.040 | Rn.9714 | Neuropeptide Y |
| BF285985 | 4 | −0.06 | −0.001 | 0.016 | 0.074 | Rn.42366 | protein tyrosine phosphatase, receptor type, f polypeptide (PTPRF), interacting protein (liprin), alpha 4 |
| AI412889 | 4 | −0.08 | −0.001 | 0.012 | 0.105 | Rn.23659 | monocyte to macrophage differentiation-associated 2 (Mm.) (DBSS) |
| AJ002556 | 4 | −0.54 | −0.003 | 0.006 | 0.050 | Rn.37490 | microtubule-associated protein 6 |
| AI179459 | 4 | 0.12 | −0.011 | −0.094 | −0.152 | Rn.31366 | Kell blood group (Mm.) (DBSS_moderate) |
| AI603128 | 4 | 0.15 | −0.019 | −0.127 | −0.330 | Rn.13094 | Cyclin A2 (Cyclin A) (Mm.) (DBSS_strong) |
| BE111688 | 4 | 1.72 | −0.082 | −0.048 | −0.343 | Rn.23351 | cyclin B2 (Hs.) (DBSS_strong) |

TABLE 4-continued 186 genes identified to be necessary and sufficient to classify the training set.

| Probe | Iteration | Weight | Impact | Mean Logratio Positive Class | Mean Logratio Negative Class | Unigene ID | UniGene Description |
|---|---|---|---|---|---|---|---|
| NM_012892 | 5 | −0.70 | 0.128 | −0.184 | −0.127 | Rn.37523 | amiloride-sensitive cation channel 1 |
| BE098463 | 5 | 2.30 | 0.101 | 0.044 | −0.100 | Rn.18203 | ESTs |
| C06844 | 5 | −0.94 | 0.095 | −0.101 | 0.075 | Rn.7159 | S49158 complement protein C1q beta chain precursor (Rn.) (DBSS_weak) |
| AI170114 | 5 | −0.42 | 0.078 | −0.183 | −0.112 | Rn.91697 | ESTs |
| AI105265 | 5 | −1.53 | 0.073 | −0.048 | 0.009 | Rn.5911 | hypothetical protein FLJ10315 (Hs.) (DBSS_strong) |
| BF394214 | 5 | −0.79 | 0.071 | −0.090 | −0.014 | Rn.58227 | ESTs |
| AA946356 | 5 | −1.08 | 0.063 | −0.058 | −0.017 | Rn.1435 | CGG triplet repeat binding protein 1 (Hs.) (DBSS) |
| AW919159 | 5 | 1.09 | 0.056 | 0.051 | −0.022 | Rn.41574 | A38135 ADP-ribosylarginine hydrolase (Rn.) (DBSS_weak) |
| AI230884 | 5 | 1.61 | 0.053 | 0.033 | −0.034 | Rn.9797 | Fibroblast growth factor receptor 1 |
| BF406522 | 5 | 0.92 | 0.052 | 0.056 | −0.019 | Rn.3537 | cerebellar degeneration-related protein 2, 62 kDa (Hs.) (DBSS) |
| NM_012848 | 5 | 0.14 | 0.048 | 0.350 | 0.110 | Rn.54447 | ferritin, heavy polypeptide 1 |
| AW914090 | 5 | −1.61 | 0.046 | −0.029 | 0.002 | Rn.973 | 60S acidic ribosomal protein P1 (Rn.) (DBSS_strong) |
| AW142828 | 5 | −0.65 | 0.044 | −0.068 | −0.034 | Rn.23877 | ESTs |
| AI705731 | 5 | −0.95 | 0.040 | −0.042 | 0.058 | Rn.24919 | transcription factor MTSG1 |
| NM_019126 | 5 | −0.33 | 0.037 | −0.112 | 0.140 | Rn.25723 | Carcinoembryonic antigen gene family (CGM3) |
| U73503 | 5 | 0.64 | 0.037 | 0.057 | −0.014 | Rn.10961 | calcium/calmodulin-dependent protein kinase (CaM kinase) II gamma |
| AF017437 | 5 | 0.55 | 0.036 | 0.066 | −0.010 | Rn.7409 | integrin-associated protein |
| NM_021869 | 5 | −0.42 | 0.035 | −0.083 | 0.057 | Rn.1993 | syntaxin 7 |
| AI144644 | 5 | −0.34 | 0.030 | −0.087 | 0.024 | Rn.12319 | ESTs |
| AA818377 | 5 | 0.79 | 0.029 | 0.037 | −0.033 | Rn.34063 | hypothetical protein FLJ22419 (Hs.) (DBSS_weak) |
| AI171994 | 5 | 0.13 | 0.027 | 0.198 | 0.008 | Rn.22380 | ESTs |
| AA925167 | 5 | −0.12 | 0.022 | −0.180 | 0.106 | Rn.8672 | ESTs |
| BF398051 | 5 | −0.38 | 0.020 | −0.053 | 0.080 | Rn.97322 | ESTs |
| AW144075 | 5 | 0.48 | 0.019 | 0.040 | −0.024 | Rn.19790 | ESTs |
| U26686 | 5 | −0.09 | 0.015 | −0.158 | −0.045 | Rn.10400 | nitric oxide synthase 2 |
| BF404426 | 5 | −0.07 | 0.009 | −0.128 | −0.032 | Rn.63325 | ESTs |
| U31866 | 5 | 0.24 | 0.007 | 0.029 | −0.037 | Rn.32307 | Nclone10 mRNA |
| AW917475 | 5 | −0.07 | 0.006 | −0.087 | 0.055 | Rn.16643 | high-affinity immunoglobulin gamma Fc receptor I |
| AI408517 | 5 | 0.44 | 0.006 | 0.013 | 0.021 | Rn.2773 | protein phosphatase 1, regulatory (inhibitor) 5 subunit 14B |
| AF207605 | 5 | −0.34 | 0.005 | −0.015 | 0.000 | Rn.42674 | tubulin tyrosine ligase |
| AI178922 | 5 | −0.41 | 0.005 | −0.012 | −0.023 | Rn.18670 | leucine zipper and CTNNBIP1 domain containing (Hs.) (DBSS_moderate) |
| BF398403 | 5 | 0.41 | 0.005 | 0.011 | −0.037 | Rn.20421 | mannosyl-oligosaccharide 1,3-1,6-alpha-mannosidase (EC 3.2.1.114) (Mm.) (DBSS_moderate) |
| M22923 | 5 | 0.05 | 0.004 | 0.091 | −0.019 | Rn.10922 | membrane-spanning 4-domains, subfamily A, member 2 |
| BE107747 | 5 | −0.05 | 0.004 | −0.077 | 0.041 | Rn.29176 | ESTs |
| BF281697 | 5 | 0.57 | 0.004 | 0.007 | −0.024 | Rn.7770 | potassium voltage-gated channel, Isk-related family, member 1-like (Hs.) (DBSS) |

TABLE 4-continued 186 genes identified to be necessary and sufficient to classify the training set.

| Probe | Iteration | Weight | Impact | Mean Logratio Positive Class | Mean Logratio Negative Class | Unigene ID | UniGene Description |
|---|---|---|---|---|---|---|---|
| AB006461 | 5 | 0.03 | 0.002 | 0.059 | −0.009 | Rn.5653 | neurochondrin |
| AF100960 | 5 | 0.03 | 0.001 | 0.051 | −0.038 | Rn.8633 | FAT tumor suppressor (*Drosophila*) homolog |
| U79031 | 5 | −0.07 | 0.000 | 0.006 | 0.048 | Rn.44299 | adrenergic receptor, alpha 2a |
| NM_017353 | 5 | −0.21 | −0.004 | 0.019 | 0.045 | Rn.32261 | tumor-associated protein 1 |
| AI231716 | 5 | 1.81 | −0.007 | −0.004 | −0.138 | Rn.24598 | ESTs |
| NM_012964 | 5 | 0.67 | −0.024 | −0.036 | −0.298 | Rn.92304 | Hyaluronan mediated motility receptor (RHAMM) |
| L06040 | 5 | 0.19 | −0.035 | −0.183 | −0.306 | Rn.11318 | arachidonate 12-lipoxygenase |

The 186 genes of the necessary set listed in Table 4 correspond to 164 reward genes, of which 72 are induced on average across the nephrotoxicants. Additional genes not necessary for classification, but nonetheless differentially regulated by the nephrotoxicants relative to the negative class, were also considered.

Example 5

Using a Necessary Set to Generate New Signatures for Renal Tubule Injury

As shown above in Examples 1-3, a predictive signature for renal tubule injury comprising 35 genes may be derived using gene expression data from a microarray in the context of a chemogenomic database. Using the signature stripping method described above, four additional high performing predictive signatures for renal tubule injury may also be derived wherein each of the signatures is non-overlapping, i.e., comprises genes not used in any of the other signatures. Together, the union of the genes in these five signatures comprises a set of 186 genes that is necessary for deriving a predictive signature for renal tubule injury capable of classifying the training set above a selected threshold level of LOR=1.64.

This example demonstrates that additional signatures for renal tubule injury may be generated based on the necessary set of 186 genes. In addition, it is shown that at least four genes must be selected from the necessary set in order to generate a signature for renal tubule injury capable of performing above a selected threshold LOR of 4.00.

As listed in Table 4, for each gene from the necessary set of 186, an impact factor was calculated, corresponding to the product of the gene's weight and the gene's expression mean logratio in the positive class (i.e., nephrotoxicants). Subsets of genes were chosen randomly from the necessary set of 186 so that the sum of the impacts of all genes in the subset accounted for 1, 2, 4, 8, 16, 32, or 64% of the total impact. Total impact was defined as the sum of the individual impacts of all 186 genes in the necessary set. This random subset selection procedure was repeated 20 times resulting in 140 gene subsets (i.e., 7 impact thresholds times 20 random choices).

Table 5 shows the average number of genes for each of these seven impact thresholds. This number increases regularly reaching an average of 116 genes for those subsets that account for 64% of the total impact. Each of these random subsets was used as input to compute a renal tubule injury signature using the SPLP algorithm as described in Example 3 above. A training LOR and a 10-fold cross-validated test LOR were calculated for each signature. Table 5 lists average LOR values for the signatures generated in each of the seven percent of total impact thresholds. Based on the results tabulated in Table 5 it may be concluded that signatures for renal tubule injury capable of performing with an average training LOR of 4.30 may be generated starting with random subsets having an average of 4.4 genes that together have only 2% of the total impact of the necessary set. Similarly signatures capable of performing with an average test LOR of 4.41 may be derived from random subsets of the necessary set having an average of 9.15 genes with only 4% of the total impact. Significantly, the average training LOR never drops below 4.00 when a random set of genes having at least 4% impact are selected. As shown in Table 5, comparably higher performing signatures are derived from the necessary set when the random subsets have a percent impact of 8% or higher.

TABLE 5

RTI signatures generated based on randomly selecting necessary set genes with minimal percentage impact

| | # input genes | | | Signature Length | | | LOR (training) | | LOR (test) | |
|---|---|---|---|---|---|---|---|---|---|---|
| percent impact* | avg | min | max | avg | min | max | avg | stdev | avg | stdev |
| 1 | 2.85 | 1 | 5 | 2.8 | 1 | 5 | 3.42 | 1.61 | 3.01 | 1.34 |
| 2 | 4.4 | 1 | 9 | 4.3 | 1 | 8 | 4.30 | 1.61 | 3.20 | 1.00 |

TABLE 5-continued

RTI signatures generated based on randomly selecting necessary set genes with minimal percentage impact

| percent impact* | # input genes | | | Signature Length | | | LOR (training) | | LOR (test) | |
|---|---|---|---|---|---|---|---|---|---|---|
| | avg | min | max | avg | min | max | avg | stdev | avg | stdev |
| 4 | 9.15 | 3 | 17 | 8.05 | 3 | 13 | 6.82 | 2.34 | 4.41 | 2.43 |
| 8 | 17.3 | 8 | 27 | 12.8 | 8 | 18 | 8.54 | 0.61 | 5.91 | 1.99 |
| 16 | 33.4 | 22 | 42 | 19.2 | 14 | 25 | 8.68 | 0.00 | 7.85 | 2.01 |
| 32 | 61.6 | 49 | 76 | 26.5 | 22 | 30 | 8.68 | 0.00 | 7.35 | 2.03 |
| 64 | 116 | 100 | 134 | 30.7 | 28 | 36 | 8.68 | 0.00 | 7.07 | 1.50 |

*average of 20 lists chosen from the necessary set

Table 6 shows the parameters for 20 signatures generated from random subsets of genes with 2% of the total impact of the 186 gene necessary set. Tables 7 (subset 8) and 8 (subset 14) illustrate two specific 5 gene signatures (including values for gene weights and bias) for predicting renal tubule injury onset that perform with a training LOR of 4.00 and 7.3, respectively.

TABLE 6

RTI signatures generated based on random selections of necessary set genes with 2% impact

| Subset # | # Input Genes | Signature Length | Training LOR | Test LOR |
|---|---|---|---|---|
| 14 | 5 | 5 | 7.3 | 5.0 |
| 9 | 7 | 7 | 6.8 | 3.4 |
| 15 | 5 | 5 | 6.2 | 4.1 |
| 7 | 6 | 6 | 6.0 | 3.2 |
| 18 | 5 | 5 | 5.8 | 3.7 |
| 3 | 4 | 4 | 5.5 | 4.0 |
| 10 | 9 | 8 | 5.0 | 2.8 |
| 2 | 4 | 3 | 4.7 | 1.7 |
| 13 | 3 | 3 | 4.5 | 3.2 |
| 19 | 6 | 6 | 4.4 | 2.6 |
| 8 | 5 | 5 | 4.0 | 2.8 |
| 11 | 5 | 5 | 3.8 | 4.5 |
| 4 | 4 | 4 | 3.8 | 4.0 |
| 12 | 4 | 4 | 3.8 | 5.1 |
| 20 | 4 | 4 | 3.2 | 2.7 |
| 5 | 3 | 3 | 2.8 | 2.6 |
| 1 | 4 | 4 | 2.6 | 2.4 |
| 17 | 3 | 3 | 2.2 | 2.4 |
| 6 | 1 | 1 | 2.1 | 1.6 |
| 16 | 1 | 1 | 1.7 | 2.3 |

TABLE 7

Subset 8

| BF283302 | 15.5 |
|---|---|
| AW920818 | 5.88 |
| AW141985 | 5.48 |
| BF403410 | 4.28 |
| AA858649 | −2.3 |
| Bias | 1.13 |

TABLE 8

Subset 14

| AI176933 | 43.1 |
|---|---|
| U08257 | 33.7 |
| BE116947 | 18.4 |
| AI408517 | 12.7 |
| AA819832 | −2.9 |
| Bias | 8.49 |

Similarly Table 9 shows the parameters for 20 signatures generated from random subsets of genes with 4% of the total impact of the 186 gene necessary set. Tables 10 (subset 18) and 11 (subset 5) illustrate specific 9 and 13 gene signatures for predicting renal tubule injury onset that perform with a test LOR of 4.1 and 10.2, respectively.

TABLE 9

| Subset # | # Input Genes | Signature Length | Training LOR | Test LOR |
|---|---|---|---|---|
| 5 | 13 | 13 | 8.7 | 10.2 |
| 2 | 14 | 11 | 8.7 | 8.9 |
| 7 | 11 | 10 | 8.7 | 8.9 |
| 9 | 17 | 11 | 8.7 | 6.2 |
| 20 | 11 | 9 | 8.7 | 5.3 |
| 10 | 14 | 12 | 8.7 | 4.7 |
| 11 | 13 | 12 | 8.7 | 4.6 |
| 14 | 7 | 6 | 8.7 | 4.5 |
| 12 | 9 | 8 | 8.7 | 4.3 |
| 18 | 9 | 9 | 8.7 | 4.1 |
| 15 | 11 | 9 | 8.7 | 3.8 |
| 3 | 6 | 6 | 6.2 | 3.3 |
| 19 | 7 | 6 | 6.2 | 3.2 |
| 13 | 6 | 6 | 4.7 | 3.1 |
| 8 | 11 | 9 | 6.8 | 2.7 |
| 4 | 5 | 5 | 4.3 | 2.7 |
| 17 | 5 | 5 | 3.7 | 2.1 |
| 1 | 7 | 7 | 3.7 | 2.1 |
| 6 | 4 | 4 | 3.4 | 2.0 |
| 16 | 3 | 3 | 1.9 | 1.5 |

TABLE 10

Subset 18

| AW143273 | 55.95 |
|---|---|
| AI599126 | 29.8 |
| AI705731 | 19.05 |
| BF406522 | 16.71 |
| AB027155 | −4.12 |
| AW253895 | −13.53 |
| AA819832 | −14.81 |
| X68878 | −17.57 |
| AW140530 | −19.85 |
| Bias | 8.96 |

TABLE 11

Subset 5

| | |
|---|---|
| AW144075 | 4.82 |
| AI113104 | 4.58 |
| AI171994 | 4.25 |
| AW920818 | 3.39 |
| BF281697 | 3.11 |
| AI012120 | 1.76 |
| BE110577 | 1.08 |
| NM 012964 | 0.87 |
| AI227912 | 0.74 |
| AW144399 | −0.2 |
| AI232347 | −2.9 |
| AA944518 | −6.4 |
| AW914090 | −6.6 |
| Bias | 0.68 |

Figure 2:
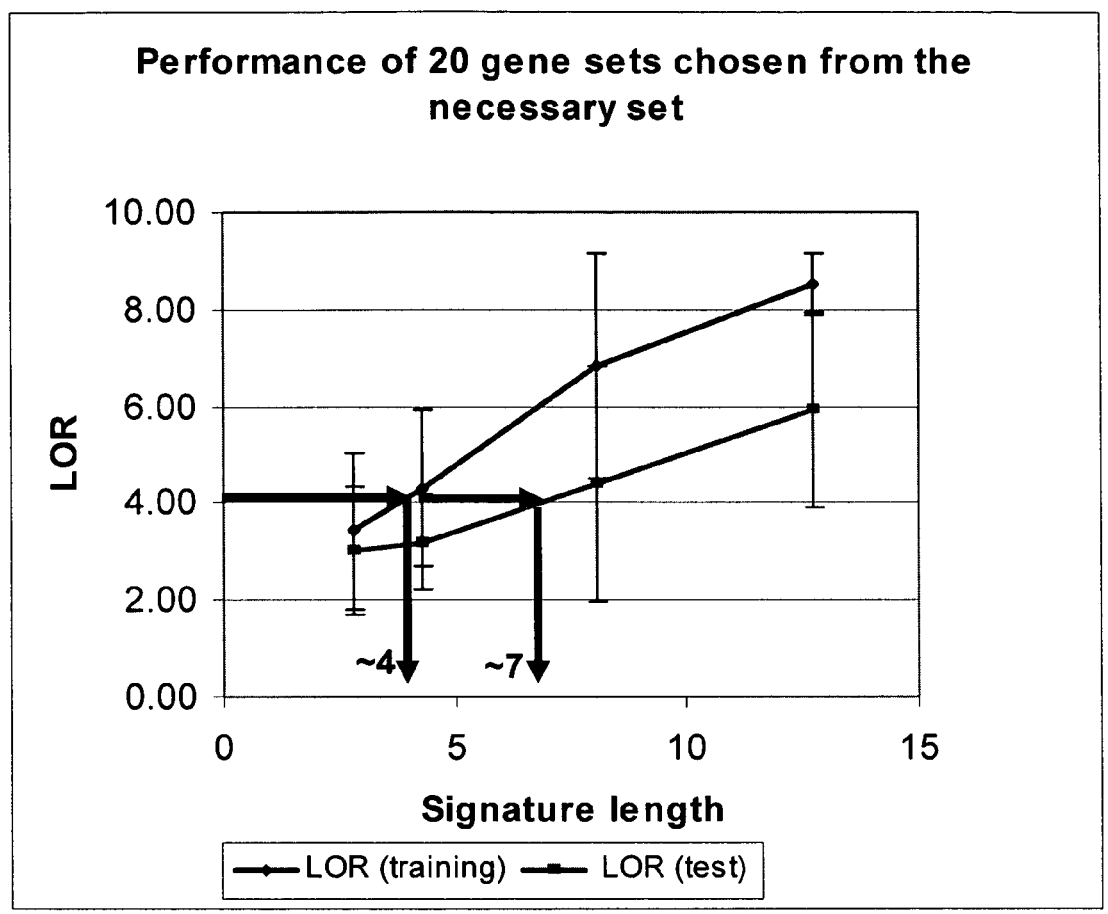
FIG. 2 depicts a plots of training and test logodds ratios for prediction of renal tubule injury for 20 subsets of genes randomly selected from the necessary set. A training or test LOR of 4.00 could be achieved by signatures of as few as 4 and 7 genes, respectively.

The results tabulated in Table 5 may also be illustrated graphically. As shown in FIG. 2, which plots training LOR and test LOR versus signature length, a signature performing with an average training LOR of 4.00 may be achieved by randomly selecting on average 4 genes from the necessary set. Similarly, an average test LOR of 4.00 may be achieved by randomly selecting on average 7 genes from the necessary set.

Example 6

Functional Characterization of the Necessary Set of Genes for Renal Tubule Injury by Random Supplementation of a Fully Depleted Set This example illustrates how the set of 186 genes necessary for classifying renal tubule injury may be functionally characterized by randomly supplementing and thereby restoring the ability of a depleted gene set to generate RTI signatures capable of performing on average above a threshold LOR. In addition to demonstrating the power of the 186 information rich genes in the RTI necessary set, this example illustrates a system for describing any necessary set of genes in terms of its performance parameters.

As described in Example 4, a necessary set of 186 genes (see Table 4) for the RTI classification question was generated via the stripping method. In the process, a corresponding fully depleted set of 7292 genes (i.e., the full dataset of 7478 genes minus 186 genes) was also generated. The fully depleted set of 7292 genes was not able to generate an RTI signature capable of performing with a LOR greater than or equal to 1.28 (based on cross-validation using 40 random 80:20 training:test splits).

A further 186 genes were randomly removed from the fully depleted set. Then a randomly selected set including 10, 20, 40 or 80% of the genes from either: (a) the necessary set; or (b) the set of 186 randomly removed from the fully depleted set; is added back to the depleted set minus 186. The resulting "supplemented" depleted set was then used to generate an RTI signature, and the performance of this signature is cross-validated using 3 random 60:40 training:test splits. This process was repeated 20 times for each of the different percentage supplementations of genes from the necessary set and the random 186 genes removed from the original depleted set. Twenty cross-validated RTI signatures were obtained for each of the various percentage supplementations of the depleted set. Average LOR values were calculated based on the 20 signatures generated for each percentage supplementation.

Results

As shown in Table 12, supplementing the fully depleted set (minus random 186) with as few as 10% of the randomly chosen genes from the necessary set results in significantly improved performance for classifying RTI. The random 10% of genes selected from the depleted 186 yielded signatures performing with an avg. LOR=1.4. In contrast, supplementing the depleted set (minus random 186) with 10% from the necessary set yields RTI signatures performing with an avg. LOR=4.5 (based on 3-fold cross-validation using random 60:40 splits).

TABLE 12

Supplementation with random genes from necessary or depleted sets

| % | Necessary Set Avg. LOR | Depleted Set Avg. LOR |
|---|---|---|
| 10 | 4.51 | 1.43 |
| 20 | 4.93 | 2.32 |
| 40 | 4.73 | 2.63 |
| 80 | 4.10 | 3.28 |

Although increasing the percentage of random "depleted" set genes used to supplement resulted in an increase in average performance, even at 80%, the average LOR remained below 4.00, while supplementation with the random 80% "necessary" set genes yielded an average LOR above 4.00.

These results demonstrate how supplementation with a percentage of randomly selected genes from the RTI necessary set of 186 "revives" the performance of a fully depleted set for generating classifiers. Thus, the RTI necessary set of genes may be functionally characterized as the set of genes for which a randomly selected 10% will supplement a set of genes fully depleted for RTI classification (i.e., not capable of producing RTI signatures with avg. LOR>~1.4), such that the resulting "revived" gene set generates RTI signatures with an average LOR greater than or equal to 4.00.

Example 7

Construction and Use of a DNA Array for Predicting Renal Tubule Injury

The necessary subset of 186 genes identified to be necessary and sufficient to classify the renal tubule injury training set listed in Table 4 may be used as the basis for a DNA array diagnostic device for predicting renal tubule injury. The device may be used in a therapeutic monitoring context, such as for monitoring the response of an individual to a compound that is suspected of possibly causing renal tubule injury (or related nephrotoxic side effects). Alternatively, smaller sufficient subsets of genes the necessary set, which may be selected according to the methods of Examples 4 and 5 described above, may be used as the basis for a DNA array.

The probe sequences used to represent the 186 (or fewer) genes on the array may be the same ones used on the Amersham CodeLink™ RU1 platform DNA array used to derive the renal tubule injury signature as described in Examples 1-3. The 186 probes are pre-synthesized in a standard oligonucleotide synthesizer and purified according to standard techniques. The pre-synthesized probes are then deposited onto treated glass slides according to standard methods for array spotting. For example, large numbers of slides, each containing the set of 186 probes, are prepared simultaneously using a robotic pen spotting device as described in U.S. Pat. No. 5,807,522. Alternatively, the 186 probes may be synthesized in situ one or more glass slides from nucleoside precursors according to standard methods well known in the art such as ink-jet deposition or photoactivated synthesis.

The DNA probe arrays made according to this method are then each hybridized with a fluorescently labeled nucleic acid sample. The nucleic acid may be derived from mRNA obtained from a biological fluid (e.g., blood) or a tissue sample from a compound treated individual. Any of the well-known methods for preparing labeled samples for DNA probe array hybridization may be used. The fluorescence intensity data from hybridization of the sample to the DNA array of 186 (or fewer) genes of the necessary set is used to calculate expression log ratios for each of the genes. Depending on the specific gene signature selected for use in predicting renal tubule injury (e.g., the genes in iteration 1 of Table 4), the scalar product for that signature is calculated (i.e., sum of the products of expression $\log_{10}$ ratio and weight for each gene less the bias). If the scalar product is greater than zero then the sample is classified as positive (i.e., onset of renal tubule injury is predicted).

All publications and patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

What is claimed:

1. A method for testing whether a compound will induce renal tubule injury in a test subject, the method comprising:
   a) administering a dose of compound to at least one test subject, wherein the test subject is a mouse or rat;
   b) after a selected time period, obtaining a biological sample from the at least one test subject;
   c) measuring the expression levels in the biological sample of at least a plurality of sequences selected from Table 4, wherein the plurality of sequences comprises AI105417, BF404557, U08257, BF285022, and AF155910 and has at least 2% of the total impact of all of the sequences in Table 4; and
   d) determining whether the sample is in the positive class for renal tubule injury using a classifier comprising at least the plurality of sequences for which the expression levels are measured.

2. The method of claim 1, wherein the test compound is administered by route of IV, PO, or IP.

3. The method of claim 1, wherein the dose administered does not cause histological or clinical evidence of renal tubule injury at about 5 days.

4. The method of claim 1, wherein the biological sample comprises kidney tissue.

5. The method of claim 1, wherein the selected period of time is about 5 days or fewer.

6. The method of claim 1, wherein said selected period of time is at least 28 days.

7. The method of claim 1, wherein the expression levels are measured as $\log_{10}$ ratios of a compound-treated biological sample to a compound-untreated biological sample.

8. The method of claim 1, wherein the classifier is a non-linear classifier.

9. The method of claim 1, wherein the classifier is a linear classifier.

10. The method of claim 9, wherein the linear classifier comprises the sequences and weights corresponding to any one of iterations 1 through 5 in Table 4.

11. The method of claim 10, wherein the linear classifier for renal tubule injury classifies the nephrotoxic versus non-nephrotoxic compounds listed in Table 2 with a training log odds ratio of greater than or equal to 4.35.

12. The method of claim 1, wherein the plurality of sequences from Table 4 includes at least 8 sequences selected having at least 4% of the total impact of all of the sequences in Table 4.

* * * * *

UNITED STATES PATENT AND TRADEMARK OFFICE
CERTIFICATE OF CORRECTION

PATENT NO. : 7,588,892 B2 Page 1 of 1
APPLICATION NO. : 11/184272
DATED : September 15, 2009
INVENTOR(S) : Natsoulis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 751 days.

Signed and Sealed this

Twenty-first Day of September, 2010

David J. Kappos
*Director of the United States Patent and Trademark Office*